(12) United States Patent
Reisner et al.

(10) Patent No.: US 8,974,779 B2
(45) Date of Patent: Mar. 10, 2015

(54) DISEASE TREATMENT VIA DEVELOPING NON-SYNGENEIC GRAFT TRANSPLANTATION

(75) Inventors: Yair Reisner, Old Jaffa (IL); Benjamin Dekel, Tel-Aviv (IL); Smadar Eventov-Friedman, Doar-Na Shimshon (IL); Helena Katchman, Givataim (IL); Elias Shezen, Rechovot (IL); Anna Aronovich, Givataim (IL); Dalit Tchorsh, Tel-Aviv (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 1752 days.

(21) Appl. No.: 11/664,530

(22) PCT Filed: Oct. 2, 2005

(86) PCT No.: PCT/IL2005/001059
§ 371 (c)(1),
(2), (4) Date: Jul. 30, 2009

(87) PCT Pub. No.: WO2006/038211
PCT Pub. Date: Apr. 13, 2006

(65) Prior Publication Data
US 2010/0021433 A1 Jan. 28, 2010
US 2015/0010512 A9 Jan. 8, 2015

Related U.S. Application Data

(63) Continuation-in-part of application No. 11/037,025, filed on Jan. 19, 2005, now Pat. No. 7,780,993, which is a continuation-in-part of application No. 10/759,033, filed on Jan. 20, 2004, now abandoned, which is a continuation-in-part of application No. 10/379,725, filed on Mar. 6, 2003, now abandoned.

(60) Provisional application No. 60/614,968, filed on Oct. 4, 2004.

(30) Foreign Application Priority Data

Nov. 28, 2004 (IL) .......................................... 165425

(51) Int. Cl.
*A61K 35/39* (2006.01)
*A61K 31/436* (2006.01)
*A61K 35/26* (2006.01)
*A61K 35/28* (2006.01)
*A61K 35/42* (2006.01)
*A61L 27/36* (2006.01)

(52) U.S. Cl.
CPC ............... *A61K 35/39* (2013.01); *A61K 31/436* (2013.01); *A61K 35/26* (2013.01); *A61K 35/28* (2013.01); *A61K 35/42* (2013.01); *A61L 27/3604* (2013.01); *A61L 27/3641* (2013.01)
USPC ....................................................... 424/93.7

(58) Field of Classification Search
None
See application file for complete search history.

(56) References Cited

U.S. PATENT DOCUMENTS

| | | | |
|---|---|---|---|
| 5,175,004 | A | 12/1992 | Matsumura |
| 5,580,558 | A | 12/1996 | Kitamura |
| 5,593,673 | A | 1/1997 | Dinsmore |
| 5,635,365 | A | 6/1997 | Ansari et al. |
| 5,658,564 | A | 8/1997 | Sykes et al. |
| 5,811,089 | A | 9/1998 | Smikodub et al. |
| 5,876,708 | A | 3/1999 | Sachs |
| 5,919,449 | A | 7/1999 | Dinsmore |
| 5,942,435 | A | 8/1999 | Wheeler |
| 5,961,972 | A | 10/1999 | Dinsmore |
| 5,976,524 | A | 11/1999 | Hammerman |
| 6,024,957 | A | 2/2000 | Lazarovits et al. |
| 6,060,049 | A | 5/2000 | Beschorner |
| 6,140,116 | A | 10/2000 | Dinsmore |
| 6,183,734 | B1 | 2/2001 | Chen et al. |
| 6,194,147 | B1 | 2/2001 | Baxter-Lowe et al. |
| 6,274,629 | B1 | 8/2001 | Cottens et al. |
| 6,610,288 | B1 | 8/2003 | Edge et al. |
| 6,660,905 | B1 | 12/2003 | Kay et al. |
| 2001/0049827 | A1 | 12/2001 | Hunter et al. |
| 2003/0032184 | A1 | 2/2003 | Lagasse et al. |
| 2003/0096016 | A1 | 5/2003 | Reisner et al. |
| 2003/0198628 | A1 | 10/2003 | Hammerman |
| 2004/0082064 | A1 | 4/2004 | Reisner et al. |

(Continued)

FOREIGN PATENT DOCUMENTS

| | | |
|---|---|---|
| AU | 2005290849 | 4/2006 |
| EP | 0853942 | 7/1998 |

(Continued)

OTHER PUBLICATIONS

Translation of Office Action Dated Oct. 30, 2011 From the Israeli Patent Office Re. Application No. 182363.

(Continued)

*Primary Examiner* — Allison Fox

(57) ABSTRACT

A method of providing a pancreatic, lymphoid/hematopietic or pulmonary organ and/or tissue function to a mammalian subject is provided. The method comprises transplanting into the subject a developing mammalian pancreatic, lymphoid/hematopietic or pulmonary organ/tissue graft, respectively, thereby generating a functional pancreatic, lymphoid/hematopietic or pulmonary organ and/or tissue, respectively, for providing the pancreatic, lymphoid/hematopietic or pulmonary organ and/or tissue function, respectively, to the subject.

7 Claims, 16 Drawing Sheets

(15 of 16 Drawing Sheet(s) Filed in Color)

(56) References Cited

U.S. PATENT DOCUMENTS

| | | |
|---|---|---|
| 2004/0136972 A1 | 7/2004 | Reisner et al. |
| 2004/0191228 A1 | 9/2004 | Reisner et al. |
| 2005/0226854 A1 | 10/2005 | Reisner et al. |
| 2006/0040386 A1 | 2/2006 | Holgersson |
| 2009/0324607 A1 | 12/2009 | Reisner et al. |
| 2010/0221270 A1 | 9/2010 | Reisner et al. |

FOREIGN PATENT DOCUMENTS

| | | |
|---|---|---|
| WO | WO 96/37602 | 11/1996 |
| WO | WO 00/39294 | 7/2000 |
| WO | WO 00/41713 | 7/2000 |
| WO | WO 02/00722 | 1/2002 |
| WO | WO 02/39294 | 5/2002 |
| WO | WO 03/022123 | 3/2003 |
| WO | WO 2004/016276 | 2/2004 |
| WO | WO 2004/078022 | 9/2004 |
| WO | WO 2006/038211 | 4/2006 |
| WO | WO 2006/077592 | 7/2006 |

OTHER PUBLICATIONS

International Search Report and the Written Opinion Dated Mar. 30, 2007 From the International Searching Authority Re.: Application No. PCT/IL05/01059.
Office Action Dated Oct. 28, 2009 From the Israel Patent Office Re.: Application No. 182363 and Its Translation Into English.
Communication Pursuant to Article 94(3) EPC Dated Dec. 18, 2009 From the European Patent Office Re.: Application No. 05796118.7.
Office Action Dated Jan. 9, 2011 From the Israel Patent Office Re.: Application No. 182363 and Its Translation Into English.
Response Dated May 8, 2011 to Office Action of Jan. 9, 2011 From the Israel Patent Office Re.: Application No. 182363.
Response Dated Apr. 18, 2010 to Communication Pursuant to Article 94(3) EPC of Dec. 18, 2009 From the European Patent Office Re.: Application No. 05796118.7.
Response Dated Feb. 28, 2010 to Office Action of Oct. 28, 2009 From the Israel Patent Office Re.: Application No. 182363.
Revised Response Dated Jun. 17, 2010 to Communication Pursuant to Article 94(3) EPC of Dec. 18, 2009 From the European Patent Office Re.: Application No. 05796118.7.
Castaing et al. "Blood Glucose Normalization Upon Transplantation of Human Embryonic Pancreas Into Beta-Cell-Deficient SCID Mice", Diabetologia, XP002235309, 44(11): 2066-2076, Nov. 1, 2001.
Tuch "Reversal of Diabetes by Human Fetal Pancreas. Optimization of Requirements in the Hyperglycemic Nude Mouse", Transplantation, XP002544045, 51(3): 557-562, Mar. 1991.
International Preliminary Report on Patentability Dated May 3, 2007 From the International Bureau of WIPO Re.: Application No. PCT/IL2005/001059.
Examiner's Report Dated Jun. 13, 2008 From the Australian Government, IP Australia Re.: Application No. 2005290849.
Examiner's Report Dated May 29, 2009 From the Australian Government, IP Australia Re.: Application No. 2005290849.
Groscurth et al. "Cytodifferentiation of Human Fetal Lung Tissue Following Transplantation Into 'Nude' Mice", Anatomy and Embryology, 165: 291-302, 1982. Abstract.
Response Dated Dec. 29, 2011 to Communication Pursuant to Article 94(3) EPC of Jun. 29, 2011 From the European Patent Office Re.: Application No. 05796118.7.
Amaratunga et al. "Porcine Pancreatic Icosapeptide as A Marker of Graft Survival and Rejection in Xenotransplantation", Xenotransplantation, 10: 622-627, 2003.
Angioi et al. "Xenografted Human Whole Embryonic and Fetal Entoblastic Organs Develop and Become Functional Adult-Like Micro-Organs", Journal of Surgical Research, 102: 85-94, 2002.
Armstrong et al. "The Potential for Circuit Reconstruction by Expanded Neural Precursor Cells Explored Thorough Porcine Xenografts in a Rat Model of Parkinson's Disease", Experimental Neurology, 175: 98-111, 2002.

Beattie et al. "Functional Beta-Cell Mass After Transplantation of Human Fetal Pancreatic Cell. Differentiation or Proliferation?", Diabetes, 46(2): 244-248, Feb. 1997.
Dekel et al. "Acute Cellular Rejection of Human Renal Tissue by Adoptive Transfer of Allogeneic Human Peripheral Blood Mononuclear Cells Into Chimeric Rats", Sequential Gene Expression of Cytokines, Chemokines and Cytolytic Effector Molecules, and Their Regulation by CTLA-4-Ig, International Immunology, 11(10): 1673-1683, 1999.
Dekel et al. "Engraftment of Human Kidney Tissue in Rat Radiation Chimera. I. A New Model of Human Kidney Allograft Rejection", Transplantation, 64(11): 1541-1550, Dec. 15, 1997.
Dekel et al. "Engraftment of Human Kidney Tissue in Rat Radiation Chimera. I. Human Fetal Kidneys Display Reduced Immunogenicity to Adoptively Transferred Human Peripheral Blood Mononuclear Cells and Exhibit Rapid Growth and Development", Transplantation, 64(11): 1550-1558, Dec. 15, 1997.
Fox et al. "High Avidity Antibodies to Fetal Pig Pancreas Endocrine Cells Transfer Rejection But Are Not Normally Generated to Fetal Pig Pancreas Xenografts", Xenotransplantation, 9: 382-392, 2002.
Gores et al. "Long-Term Survival of Intratesticular Porcine Islets in Nonimmunosuppressed Beagles", Transplantation, 75(5): 613-618, Mar. 15, 2003.
Groth et al. "Pig-to-Human Islet Transplantation", Transplantation Proceedings, 30: 3809-3810, 1998.
Groth et al. "Transplantation of Porcine Fetal Pancreas to Diabetic Patients", The Lancet, 344: 1402-1404, 1994.
Hammerman "Transplantation of Embryonic Organs—Kidney and Pancreas", American Journal of Transplantation, 4(Suppl.6): 14-24, 2004.
Hammerman "Transplantation of Renal Precursor Cells: A New Therapeutic Approach", Pediatric Nephrology, 14(6): 513-517, Jun. 2000.
Kokudo et al. "Allogeneic Hepatocyte and Fetal Liver Transplantation and Xenogeneic Hepatocyte Transplantation for Nagase's Analbuminemic Rats", Cell Transplantation, 5(5S-1): S21-S22, 1996.
Korbutt et al. "Large Scale Isolation, Growth, and Function of Porcine Neonatal Islet Cells", The Journal of Clinical Investigation, 97(9): 2119-2129, May 1996.
Korsgren et al. "Functional and Morphological Differentiation of Fetal Porcine Islet-Like Cell Clusters After Transplantation Into Nude Mice", Diabetologia, 34: 379-386, 1991.
Korsgren et al. "Transplantation of Porcine Fetal Pancreas to A Diabetic Patient", Transplantation Proceedings, 24(1): 352-353, Feb. 1992.
Larsson et al. "Induction of Operational Tolerance to Discordant Dopaminenergic Porcine Xenografts", Transplantation, 75(9): 1448-1454, May 15, 2003.
Larsson et al. "Porcine Neural Xenografts in Rats and Mice: Donor Tissue Development and Characteristics of Rejection", Experimental Neurology, 172: 100-114, 2001.
Lim et al. "Human Fetal Trachea-Scid Mouse Xenografts: Efficacy of Vesicular Stomatitis Virus-G Pseudotyped Lentiviral-Mediated Gene Transfer", Journal of Pediatric Surgery, 38(6): 834-839, Jun. 2003.
Mannucci "Diagnosis and Therapy of Hemophilia A", Practical Laboratory Hematology, Chap.16: 347-371, 1990.
Reinholt et al. "Survival of Fetal Porcine Pancreatic Islet Tissue Transplanted to A Diabetic Patient: Findings by Ultrastructural Immunocytochemistry", Xenotransplantation, 5: 222-225, 1998.
Soederlund et al. "Fetal Porcine Islet-Like Cell Clusters Transplanted to Cynomolgus Monkeys. An Immunohistochemical Study", Transplantation, 67(6): 784-791, Mar. 27, 1999.
Takebe et al. "Xenogeneic (Pig to Rat) Fetal Liver Fragment Transplantation Using Macrocapsules for Immunoisolation", Cell Transplant, 5(S5-1): S31-S33, 1996.
Usadel et al. "Transplantation of Human Fetal Pancreas. Experience in Thymusaplastic Mice and Rats and in A Diabetic Patient", Diabetes, 29(Suppl.1): 74-79, 1980.
Communication Pursuant to Rules 70(2) and 70a(2) EPC and Reference to Rule 39(1) EPC Dated Aug. 20, 2012 From the European Patent Office Re. Application No. 11193959.1.

(56) References Cited

OTHER PUBLICATIONS

Partial European Search Report Dated Mar. 28, 2012 From the European Patent Office Re. Application No. 11193959.1.
Foglia et al. "Fetal Allograft Survival in Immunocompetent Recipients is Age Dependent and Organ Specific", Annals of Surgery, XP002671526, 204(4): 402-410, 1986. Figs.4-6.
European Search Report and the European Search Opinion Dated Jul. 13, 2012 From the European Patent Office Re. Application No. 11193959.1.
Tsuji et al. "Can Fetal Xeno Whole-Organ (Heart, Lung, Kidney, and Liver) Grafts Escape From Hyperacute Rejection in Experimental Discordant Combinations as Compared With Adult Xenografts?", Transplantation Proceedings, XP002671525, 29(7): 3022-3023, Nov. 1997. & 5th International Congress of the Middle East Society for Organ Transplantation, Limassol, Cyprus, Oct. 20-24, 1996.
Communication Pursuant to Article 94(3) EPC Dated Jun. 24, 2013 From the European Patent Office Re. Application No. 05796118.7.
Communication Pursuant to Article 94(3) EPC Dated Apr. 25, 2013 From the European Patent Office Re. Application No. 11193959.1.
Office Action Dated Apr. 11, 2013 From the Israel Patent Office Re.: Application No. 182363 and Its Translation Into English.
Communication Pursuant to Article 96(2) EPC Dated Feb. 16, 2007 From the European Patent Office Re.: Application No. 02758769.0.
International Preliminary Report on Patentability Dated Aug. 2, 2007 From the International Bureau of WIPO Re.: Application No. PCT/IL2006/000085.
Official Action Dated Aug. 8, 2007 From the US Patent and Trademark Office Re.: U.S. Appl. No. 11/037,025.
Official Action Dated Feb. 8, 2007 From the US Patent and Trademark Office Re.: U.S. Appl. No. 10/759,033.
Official Action Dated Apr. 10, 2008 From the US Patent and Trademark Office Re.: U.S. Appl. No. 11/037,025.
Official Action Dated Nov. 25, 2008 From the US Patent and Trademark Office Re.: U.S. Appl. No. 11/037,025.
Supplementary Partial European Search Report Dated Feb. 28, 2006 From the European Patent Office Re.: Application No. 02758769.0.
Applicant-Initiated Interview Summary Dated Oct. 16, 2012 From the US Patent and Trademark Office Re. U.S. Appl. No. 12/777,292.
Communication Pursuant to Article 94(3) EPC Dated Mar. 6, 2012 From the European Patent Office Re. Application No. 10154555.6.
Communication Pursuant to Article 94(3) EPC Dated Jun. 10, 2014 From the European Patent Office Re. Application No. 11179593.6.
Communication Pursuant to Article 94(3) EPC Dated Nov. 18, 2011 From the European Patent Office Re. Application No. 10154555.6.
Communication Pursuant to Article 94(3) EPC Dated Nov. 24, 2009 From the European Patent Office Re.: Application No. 02758769.0.
Communication Pursuant to Article 94(3) EPC Dated Jul. 25, 2012 From the European Patent Office Re. Application No. 11179593.6.
Communication Pursuant to Article 94(3) EPC Dated Nov. 26, 2008 From the European Patent Office Re.: Application No. 06701102.3.
Communication Pursuant to Article 94(3) EPC Dated Jan. 29, 2013 From the European Patent Office Re. Application No. 11179593.6.
Communication Pursuant to Article 94(3) EPC Dated Jun. 29, 2011 From the European Patent Office Re. Application No. 10154555.6.
Communication Pursuant to Article 94(3) EPC Dated Aug. 31, 2009 From the European Patent Office Re.: Application No. 04717207.7.
Communication Relating to the Results of the Partial International Search Dated May 30, 2006 From the International Searching Authority Re.: Application No. PCT/IL2006/000085.
Decision of the Enlarged Board of Appeal Dated Nov. 25, 2009 From the European Patent Office Re.: Application No. 96903521.1.
European Search Report and the European Search Opinion Dated Dec. 1, 2011 From the European Patent Office Re. Application No. 11179593.6.
European Search Report and the European Search Opinion Dated Nov. 9, 2010 From the European Patent Office Re. Application No. 10154555.6.
Examination Report Dated Nov. 15, 2012 From the Instituto Mexicano de la Propiedad Industrial Re. Application No. PA/a/2005/009380 and Its Translation Into English.
Examination Report Dated Jun. 19, 2008 From the Instituto Mexicano de la Propriedad Industrial Re.: Application No. PA/a/2004/002160.
Examination Report Dated Apr. 23, 2013 From the Instituto Mexicano de la Propiedad Industrial Re. Application No. PA/a/2005/009380 and Its Translation Into English.
Examination Report Dated Oct. 23, 2013 From the Instituto Mexicano de la Propiedad Industrial Re. Application No. PA/a/2005/009380 and Its Translation Into English.
Examiner's Report Dated Mar. 12, 2007 From the Australian Government, IP Australia Re.: Application No. 2002324324.
Examiner's Report Dated Aug. 13, 2008 From the Australian Government, IP Australia Re.: Application No. 2004217938.
International Preliminary Examination Report Dated Aug. 17, 2007 From the International Preliminary Examining Authority Re.: Application No. PCT/IL02/00722.
International Preliminary Report on Patentability Dated Nov. 15, 2007 From International Bureau of WIPO Re.: Application No. PCT/IL2004/000217.
International Search Report and the Written Opinion Dated Oct. 16, 2007 From the International Searching Authority Re.: Application No. PCT/IL04/00217.
Office Action Dated Apr. 3, 2012 From the Israel Patent Office Re. Application No. 170622 and Its Translation Into English.
Office Action Dated Apr. 4, 2013 From the Israel Patent Office Re.: Application No. 184740 and Its Translation Into English.
Office Action Dated Jun. 6, 2010 From the Israeli Patent Office Re.: Application No. 160723 and Its Translation Into English.
Office Action Dated Oct. 6, 2011 From the Israel Patent Office Re.: Application No. 184740 and Its Translation Into English.
Office Action Dated Feb. 11, 2009 From the Israeli Patent Office Re.: Application No. 160723 and its Translation Into English.
Office Action Dated May 14, 2007 From the Israeli Patent Office Re.: Application No. 160723.
Office Action Dated Sep. 15, 2010 From the Israel Patent Office Re. Application No. 170622 and Its Translation Into English.
Office Action Dated Feb. 17, 2010 From the Israel Patent Office Re.: Application No. 184740 and Its Translation Into English.
Office Action Dated Mar. 22, 2010 From the Israeli Patent Office Re.: Application No. 160723, Its Replacement Pages Presenting Claims and Its Translation into English.
Office Action Dated Oct. 24, 2013 From the Israel Patent Office Re. Application No. 170622 and Its Translation Into English.
Official Action Dated Aug. 4, 2010 From the US Patent and Trademark Office Re. U.S. Appl. No. 11/795,480.
Official Action Dated Mar. 4, 2011 From the US Patent and Trademark Office Re. U.S. Appl. No. 12/777,292.
Official Action Dated May 4, 2011 From the US Patent and Trademark Office Re. U.S. Appl. No. 12/777,292.
Official Action Dated Apr. 9, 2007 From the US Patent and Trademark Office Re.: U.S. Appl. No. 11/037,025.
Official Action Dated Jan. 9, 2012 From the US Patent and Trademark Office Re. U.S. Appl. No. 12/777,292.
Official Action Dated Jul. 10, 2009 From the US Patent and Trademark Office Re.: U.S. Appl. No. 11/037,025.
Official Action Dated Dec. 11, 2013 From the US Patent and Trademark Office Re. U.S. Appl. No. 12/777,292.
Official Action Dated Jun. 12, 2012 From the US Patent and Trademark Office Re. U.S. Appl. No. 12/777,292.
Official Action Dated Feb. 13, 2006 From the US Patent and Trademark Office Re.: U.S. Appl. No. 10/379,725.
Official Action Dated Jun. 24, 2014 From the US Patent and Trademark Office Re. U.S. Appl. No. 12/777,292.
Partial European Search Report Dated Jul. 1, 2010 From the European Patent Office Re. Application No. 10154555.6.
Requisition by the Examiner Dated Jul. 31, 2009 From the Canadian Intellectual Property Office Re.: Application No. 2,459,560.
Supplementary European Search Report Dated Jun. 2, 2009 From the European Patent Office Re.: Application No. 04717207.7.
Supplementary European Search Report Dated May 23, 2006 From the European Patent Office Re.: Application No. 02758769.0.
Translation of Notice of Reason for Rejection Dated May 19, 2009 From the Japanese Patent Office Re.: Application No. 2003-526257.

(56) References Cited

OTHER PUBLICATIONS

Written Opinion Dated Mar. 1, 2006 From the International Preliminary Examining Authority Re.: Application No. PCT/IL02/00722.
Abrahamson et al. "Glomerular Development in Intraocular and Intrarenal Grafts of Fetal Kidneys", Laboratory Investigation, 64(5): 629-639, 1991.
Aronovich et al. "Correction of Hemophilia as a Proof of Concept for Treatment of Monogenic Diseases by Fetal Spleen Transplantation", Proc. Natl. Acad. Sci. USA, PNAS, XP055011328, 103(50): 19075-19080, Dec. 12, 2006.
Ashkar et al. "Eta-1 (Osteopontin): An Early Component of Type-1 (Cell-Mediated) Immunity", Science, 287: 860-863, 2000.
Assmus et al. "Transplantation of Progenitor Cells and Regeneration Enhancement in Acute Myocardial Infarction (TOPCARE-AMI)", Circulation, 106: 3009-3017, 2002.
Auchincloss et al. "Xenogeneic Transplantation", Annual Reviews in Immunology, 16: 433-470, 1998.
Barakat et al. "The Capacity of Fetal and Neonatal Renal Tissues to Regenerate and Differentiate in a Heterotopic Allogeneic Subcutaneous Tissue Site in the Rat", Journal of Anatomy, 110(3): 393-407, 1971.
Barry "Renal Transplantation", Current Opinion in Urology, 10(4): 121-127, 1999.
Batanov et al. "Effect of Fetal Tissue Transplantation on Reparative Processes in Experimental Liver Cirrhosis", Bulletin of Experimental Biology and Medicine, XP002605657, 130(8): 798-801, Aug. 2000.
Benhamou "Immunomodulation With CTLA4-Ig in Islet Transplantation", Transplantation, 73(1): S40-S42, 2002.
Benichou et al. "Contributions of Direct and Indirect T Cell Alloreactivity During Allograft Rejection in Mice", The Journal of Immunology, 162: 352-358, 1999.
Biancone et al. "Study of Lymphocyte Costimulatory Molecules in Renal Transplantation", Transplantation Proceedings, 30: 2384-2386, 1998.
Bjoerklund et al. "Embryonic Stem Cells Develop Into Functional Dopaminergic Neurons After Transplantation in a Parkinson Rat Model", Proc. Natl. Acad. Sci. USA (PNAS), 99(4): 2344-2349, 2002.
Boecher et al. "Induction of Strong Hepatitis B Virus (HBV) Specific T Helper Cell and Cytotoxic T Lymphocyte Responses by Therapeutic Vaccination in the Trimera Mouse Model of Chronic HBV Infection", European Journal of Immunology, 31: 2071-2079, 2001.
Boussiotis et al. "Differential Association of Protein Tyrosine Kinases With the T Cell Receptor is Linked to the Induction of Anergy and Its Prevention by B7 Family-Mediated Costimulation", Journal of Experimental Medicine, 184: 365-376, 1996.
Brandhagen "Liver Transplantation for Hereditary Hemochromatosis", Liver Transplantation, 7(8): 663-672, 2001.
Braunwald "Shattuck Lecture—Cardiovascular Medicine at the Turn of the Millennium: Triumphs, Concerns, and Opportunities", The New England Journal of Medicine, 337(19): 1360-1370, 1997.
Briscoe et al. "The Allogeneic Response to Cultured Human Skin Equivalent in the Hu-PBL-SCID Mouse Model of Skin Rejection", Transplantation, 67(12): 1590-1599, 1999.
Britten et al. "Infarct Remodeling After Intracoronary Progenitor Cell Treatment in Patients With Acute Myocardial Infarction (TOPCARE-AMI). Mechanistic Insights From Serial Contrast-Enhanced Magnetic Resonance Imaging", Circulation, 108: 2212-2218, 2003.
Cascalho et al. "The Immunological Barrier to Xenotransplantation", Immunity, 14: 437-446, 2001.
Cecka "Kidney Transplantation From Living Unrelated Donors", Annual Review of Medicine, 51:393-406, 2000.
Crippin "Motion—Patients With Primary Sclerosing Cholangitis Should Undergo Early Liver Transplantation: Arguments Against the Motion", Canadian Journal of Gastroenterology, 16: 700-702, 2002.
Crombleholme et al. "Transplantation of Fetal Cells", American Journal of Obstetrics and Gynecology, 164(1/Pt.1): 218-230, Jan. 1991.
Curtis "End-Stage Renal Disease Patients: Referral for Transplantation", Journal of the American Society of Nephrology, 9: S137-S140, 1998.
Dabeva et al. "Hepatic Stem Cells and Liver Repopulation", Seminars in Liver Disease, 23(4): 349-362, 2003.
Dantal et al. "Effect of Long-Term Immunosuppression in Kidney-Graft Recipients on Cancer Incidence: Randomised Comparison of Two Cyclosporin Regimens", Lancet, 351: 623-628, 1998.
Dekel et al. "Engraftment and Differentiation of Human Metanephroi Into Functional Mature Nephrons After Transplantation Into Mice is Accompanied by A Profile of Gene Expression Similar to Normal Human Kidney Development", Journal of the American Society of Nephrology, XP002367823, 13(4): 977-990, Apr. 1, 2002. Fig.1.
Dekel et al. "Engraftment of Human Early Kidney Precursors", Transplant Immunology, XP002378905, 12(3-4): 241-247, Apr. 1, 2004. p. 242, col. 2, § 1, Fig.2, Abstract.
Dekel et al. "In Vivo Modulation of the Allogeneic Immune Response by Human Fetal Kidneys: The Role of Cytokines, Chemokines, and Cytolytic Effector Molecules", Transplantation, XP009061859, 69(7): 1470-1478, Apr. 15, 2000. p. 1472, r-h Col.
Desgrandchamps et al. "The Prosthetic Ureter", Journal of Endourology, 14(1): 63-77, Feb. 2000.
Eisen et al. "Cluster Analysis and Display of Genome-Wide Expression Pattern", Proc. Natl. Acad. Sci. USA, 95: 14863-14868, 1998.
Eriksson "Heart Failure: A Growing Public Health Problem", Journal of Internal Medicine, 237: 135-141, 1995.
Findlay et al. "Human Embryo: A Biological Definition", Human Reproduction, XP009125896, 22(4): 905-911, 2007.
Fischer et al. "Stem Cell Transplantation for Immunodeficiency", Springer Seminars in Immunopathology, 19: 479-492, 1998.
Freed Will Embryonic Stem Cells Be A Useful Source of Dopamine Neurosis for Transplant Into Patients With Parkinson's Disease? Proc. Natl. Acad. Sci. USA (PNAS), 99(4): 1755-1757, 2002.
French et al. "Progress in Renal Transplantation", The Canadian Journal of Urology, 7(3): 1030-1037, 2000.
Friedrich "Bone Marrow Transplantation in Immunodeficiency Diseases", The Finnish Medical Society DUODECIM, Annals in Medicine, 28: 115-119, 1996.
Frilling et al. "Current Status of Liver Transplantation for Treatment of Hepatocellular Carcinoma", Digestive Diseases, 19: 333-337, 2001.
Gaweco et al. "CD40 Expression on Graft Infiltrates and Parenchymal CD154 (CD40L) Induction in Human Chronic Renal Allograft Rejection", Kidney International, 55: 1543-1552, 1999.
Gritsch et al. "The Importance of Nonimmune Factors in Reconstitution by Discordant Xenogeneic Hematopoietic Cells", Transplantation, 57(6): 906-917, 1994.
Groth et al. "Splenic Transplantation in Gaucher Disease", Birth Defects: Original Article Series, IX(2): 102-105, 1973.
Groth et al. "Xenoislet Transplantation: Experimental and Clinical Aspects", Journal of Molecular Medicine, 77: 153-154, 1999.
Gupta et al. "Permanent Engraftment and Function of Hepatocytes Delivered to the Liver: Implications for Gene Therapy and Liver Repopulation", Hepatology, 14(1): 144-149, 1991.
Habibullah et al. "Human Fetal Hepatocyte Transplantation in Patients With Fulminant Hepatic Failure", Transplantation, 58(8): 951-952, Oct. 27, 1994.
Hagihara et al. "Effects of Iso and Xeno Fetal Liver Fragments Transplantation on Acute and Chronic Liver Failure in Rats", Cell Transplantation, 3(4): 283-290, Jul.-Aug. 1994.
Hammerman "Transplantation of Embryonic Kidneys", Clinical Science, 103: 599-612, 2002.
Hammerman "Transplantation of Renal Precursor Cells: A New Therapeutic Approach", Pediatr. Nephrol., 14: 513-517, 2000.
Hammerman "Xenotransplantation of Renal Primordia", Current Opinion in Nephrology and Hypertension, 11: 11-16, 2002.
Hanto "Classification of Epstein-Barr Virus-Associated Post-transplant Lymphoproliferative Diseases: Implications for Understanding Their Pathogenesis and Developing Rational Treatment Strategies", Annu. Rev. Med., 46: 381-394, 1995.
Hecht et al. "Embryonic Pig Pancreatic Tissue for the Treatment of Diabetes in a Nonhuman Primate Model", Proc. Natl. Acad. Sci. USA, PNAS, XP009122169, 106(21): 8659-8664, May 26, 2009.

(56) References Cited

OTHER PUBLICATIONS

Higgins et al. "Prevention of Hyperacute Rejection by Removal of Antibodies to HLA Immediately Before Renal Transplantation", The Lancet, 348: 1208-1211, 1996.
Hori et al. "Growth Inhibitors Promote Differentiation of Insulin-Producing Tissue From Embryonic Stem Cells", Proc. Natl. Acad. Sci. USA, PNAS, XP002392968, 99(25): 61105-61110, Dec. 10, 2002.
Horwitz "Primary Immune Deficiencies: Presentation, Diagnosis, and Management. Stem-Cell Transplantation for Inherited Immunodeficiency Disorders", Pediatric Clinics of North America, 47(6): 1371-1387, 2000.
Howard "What is Primary Biliary Cirrhosis?", http://www.cumc.columbia.edu/dept/gi/PBC.html, p. 1-2.
Hyink et al. "Endogenous Origin of Glomerular Endothelial and Mesangial Cells in Grafts of Embryonic Kidneys", American Journal of Physiology, 270(5/Pt.2): F886-F899, May 1996.
Ishizaka et al. "Development of Hepatocytes From ES Cells After Transfection With the HNF-3Beta Gene", The FASEB Journal, 16: 1444-1446, 2002.
Itskovitz-Eldor et al. "Differentiation of Human Embryonic Stem Cells Into Embryonic Bodies Comprising the Three Embryonic Germ Layers", Molecular Medicine, 6(2): 88-95, 2000.
Jones et al. "Hepatic Differentiation of Murine Embryonic Stem Cells", Experimental Cell Research, 272: 15-22, 2002.
Kaminski et al. "Global Analysis of Gene Expression in Pulmonary Fibrosis Reveals Distinct Programs Regulating Lung Inflammation and Fibrosis", Proc. Natl. Acad. Sci. USA, 97(4): 1778-1783, 2000.
Kaminski et al. "Practical Approaches to Analyzing Results of Microarray Experiments", Am. J. Respir. Cell Mol. Biol., 27: 125-132, 2002.
Kanai et al. "Delayed Hyperacute Xenograft Rejection in Porcine to Canine Fetal Liver Transplantation", Transplant Immunology, 7: 95-99, 1999.
Kanazawa et al. "Prospects for Zenotransplantation of the Liver", Seminars in Liver Disease, 20(4): 511-522, 2000.
Kane et al. "Neonatal Bone Marrow Transplantation for Severe Combined Immunodeficiency", Archives of Disease in Childhood—Fetal and Neonatal Edition, 85: 110-113, 2001.
Katchman et al. "Embryonic Porcine Liver as a Source for Transplantation: Advantage of Intact Liver Implants Over Isolated Hepatoblasts in Overcoming Homeostatic Inhibition by the Quiescent Host Liver", Stem Cells, 26: 1347-1355, 2008.
Keeffe "Liver Transplantation at the Millenium—Past, Present, and Future", Hepatology: A Century of Progress, p. 242-255, 2000.
Keeffe "Liver Transplantation: Current Status and Novel Approaches to Liver Replacement", Gastroenterology, 120: 749-762, 2001.
Kirkpatrick et al. "Transplantation Immunology", JAMA, 268(20): 2952-2958, 1992.
Koerner et al. "Cardiac Transplantation: The Final Therapeutic Option for the Treatment of Heart Failure", Current Opinion in Cardiology, 15: 178-182, 2000.
Kokudo et al. "Allogeneic Heopatocyte and Fetal Liver Transplantation and Xenogeneic Hepatocyte Transplantation for Nagase's Analbuminemic Rats", Cell Transplantation, 5(5S-1): S21-S22, 1996.
Kreisel et al. "Non-Hematopoietic Allograft Cells Directly Activate CD8+ T Cells and Trigger Acute Rejection: An Alternative Mechanism of Allorecognition", Nature Medicine, 8(3): 233-239, 2002.
Lee et al. "Efficient Generation of Midbrain and Hindbrain Neurons From Mouse Embryonic Stem Cells", Nature Biotechnology, 18: 675-679, 2000.
Lee et al. "Specific Tolerance Across A Discordant Xenogeneic Transplantation Barrier", Proc. Natl. Acad. Sci. USA, XP002663071, 91(23): 10864-10867, Nov. 1994.
Lenschow et al. "Long-Term Survival of Xenogeneic Pancreatic Islet Grafts Induced by CTLA4Ig", Science, XP002021689, 257(5071): 789-792, Aug. 7, 1992. Fig.1.
Levite et al. "Beneficial Effects of Bone Marrow Transplantation on the Serological Manifestations and Kidney Pathology of Experimental Systemic Lupus Erythematosus", Cellular Immunology, 162: 138-145, 1995.
Li et al. "Blocking Both Signal 1 and Signal 2 of T-Cell Activation Prevents Apoptosis of Alloreactive T Cells and Induction of Peripheral Allograft Tolerance", Nature Medicine, 5(11): 1298-1302, 1999.
Linsley et al. "CTLA-4 is a Second Receptor for the B Cell Activation Antigen B7", Journal of Experimental Medicine, 174: 561-569, 1991.
Lin et al. "Transplantation of Spleen Celles in Patients With Hemophilia A. A Report of 20 Cases", Transplant International, 7(3): 201-206, 1994.
Lubin et al. "Engraftment of Human Peripheral Blood Lymphocytes in Normal Strains of Mice", Blood, 83(8): 2368-2381, 1994.
Lumelsky et al. "Differentiation of Embryonic Stem Cells to Insulin-Secreting Structures Similar to Pancreatic Islets", Science, 292: 1389-1394, 2001.
Lupp et al. "Evaluation of 2-Year-Old Intrasplenic Fetal Liver Tissue Transplants in Rats", Cell Transplantation, 12: 423-438, 2003.
Malhi et al. "Early Cell Transplantation in LEC Rats Modeling Wilson's Disease Eliminates Hepatic Copper With Reversal of Liver Disease", Gastroenterology, 122: 438-447, 2002.
Marcus et al. "Human/Mouse Radiation Chimera are Capable of Mounting A Human Primary Humoral Response, Blood, 86(1): 398-406, 1995.
Medawar "Some Immunological and Endocrinological Problems Raised by the Evolution of Viviparitiy in Vertebrates", Symposium of the Society of Experimental Biology, 7: 320-323, 1953.
Michler et al. "Treatment of Cardiac Tumors by Orthotopic Cardiac Transplantation", Seminars in Oncology, 24(5): 534-539, 1997.
Midthun et al. "Medical Management and Complications in the Lung Transplant Recipient", Mayo Clin. Proc., 72: 175-184, 1997.
Molmenti et al. "Hepatocellular Cancer in Liver Transplantation", Journal of Hepatobiliary and Pancreatic Surgery, 8: 427-434, 2001.
Moore et al. "Stem Cell Transplantation for Autoimmune Diseases", Springer Seminars in Immunopathology, 23: 193-213, 2001.
Morrison et al. "Clinical Characteristics of Post-Transplant Lymphoproliferative Disorders", The American Journal of Medicine, 97: 14-24, 1994.
Movahedi et al. "Laparoscopic Approach for Human Islet Transplantation Into A Defined Liver Segment in Type-1 Diabetic Patients", Transplant International, 16(3): 186-190, Mar. 2003.
Nagata et al. "Basic-Liver, Pancreas, and Biliary Tract. Treatment of Cirrhosis and Liver Failure in Rats by Hepatocyte Xenotransplantation", Gastroenterology, 124: 422-431, 2003.
Naveh-Many et al. "Estrogen Receptors and Biologic Response in Rat Parathyroid Tissue and C Cells", Journal of Clinical Investigation, 90: 2434-2438, 1992.
Nelson et al. "Chemokines, Chemokine Receptors, and Allograft Rejection", Immunity, 14: 377-386, 2001.
Nikolic et al. "Normal Development in Porcine Thymus Grafts and Specific Tolerance of Human T Cells to Porcine Donor MHC", The Journal of Immunology, XP002663072, 162(6): 3402-3407, Mar. 15, 1999.
Odorico et al. "Multilineage Differentiation From Human Embryonic Stem Cell Lines", Stem Cells, XP002256790, 19(3): 193-204, 2001.
Oliver et al. "Metanephric Mesenchyme Contains Embryonic Renal Stem Cells", American Journal of Physiology—Renal Physiology, 283: 799-809, 2002.
O'Regan et al. "Osteopontin (Eta-1) in Cell-Mediated Immunity. Teaching an Old Dog New Tricks", Immunology Today, 21(10): 475-478, 2000.
Otto "Lung Stem Cells", International Journal of Experimental Pathology, 78: 291-310, 1997.
Parkman "Bone Marrow Transplantation for Immunodeficiency and Metabolic Diseases", Leukemia, 7: 1100-1102, 1993.
Perin et al. "Transendocardial, Autologous Bone Marrow Cell Transplantation for Severe, Chronic Ischemic Heart Failure", Circulation, 107: 2294-2304, 2003.
Podevin et al. "Transplantation H?patique pour Maladie Alcoolique du Fois", Journal du Chirurgie, 138(3): 147-152, 2001.

(56) References Cited

OTHER PUBLICATIONS

Porter "The Graft-Versus-Tumor Potential of Allogeneic Cell Therapy: An Update on Donor Leukocyte Infusions and Nonmyeloablative Allogeneic Stem Cell Transplantation", Journal of Hematotherapy & Stem Cell Research, 10: 465-480, 2001.
Pouzet et al. "Transplantation de Myoblastes Squelettiques Autologucs Dans I'Insuffisance Cardiaque Isch?mique", Journal de la Soci?t? de Biologie, 195(1): 47-49, 2001.
Pratt et al. "Local Synthesis of Complement Component C3 Regulates Acute Renal Transplant Rejection", Nature Medicine, 8(6): 582-587, 2002.
Ramanathan et al. "Renal Transplantation", Seminars in Nephrology, 21(2): 213-219, 2001.
Reisner et al. "The Trimera Mouse: Generating Human Monoclonal Antibodies and an Animal Model for Human Diseases", Trends in Biotechnology, 16: 242-246, 1998.
Reubinoff et al. "Embryonic Stem Cell Lines From Human Blastocysts: Somatic Differentiation In Vitro", Nature Biotechnology, 18: 399-404, 2000.
Robert et al. "Evidence That Embryonic Kidney Cells Expressing Flk-1 are Intrinsic, Vasculogenic Angioblasts", The American Journal of Physiology, 271 (Renal Fluid Electrolyte Physiology 40): F744-F753, 1996.
Rogers et al. "Transplantation of Developing Metanephroi Into Adult Rats", Kidney International, 54: 27-37, 1998.
Rogers et al. "Transplantation of Metanephroi Across the Major Histocompatibility Complex in Rats", The American Journal of Physiology—Regulatory, Integrative and Comparative Physiology, 280: 132-136, 2001.
Rogers et al. "Transplantation of Metanephroi After Preservation In Vitro", The American Journal of Physiology—Regulatory, Integrative and Comparative Physiology, 281: 661-665, 2001.
Rogers et al. "Transplantation of Pig Metanephroi", ASAIO Journal, 49: 48-52, 2003.
Rogers et al. "Transplantation of Rat Metanephroi Into Mice", American Journal of Physiology: Regulatory, Integrative and Comparative Physiology, XP002259735, 280: R1865-R1869, Jun. 1, 2001.
Samuel "Hepatitis B Virus and Liver Transplantation", Acta Gastro-Enterologica Belgica, LXIII: 197-199, 2000.
Sandhu et al. "Stem Cell Properties and Repopulation of the Rat Liver by Fetal Liver Epithelial Progenitor Cells", American Journal of Pathology, XP002605655, 159(4): 1323-1334, Oct. 2001. Figs.1-7.
Sayegh et al. "The Role of T-Cell Costimulatory Activation Pathways in Transplant Rejection", The New England Journal of Medicine, 338(25): 1813-1821, 1998.
Schuldiner et al. "Effects of Eight Growth Factors on the Differentiation of Cells Derived From Human Embryonic Stem Cells", Proc. Natl. Acad. Sci. USA, 97(21): 11307-11312, 2000.
Schumacher et al. "Transplantation of Embryonic Porcine Mesencephalic Tissue in Patients With PD", Neurology, 54(5): 1042-1050, 2000.
Schwartz "Models of T Cell Anergy: Is There A Common Molecular Mechanism", The Journal of Experimental Medicine, 184: 1-8, 1996.
Seaman "Adult Living Donor Liver Transplantation: Current Status", Journal of Clinical Gastroenterology, 33(2): 97-106, 2001.
Segall et al. "Generation of Primary Antigen-Specific Human Cytotoxic T Lymphocytes in Human/Mouse Radiation Chimera", Blood, 88(2): 721-730, 1996.
Senderowicz et al. "Complete Sustained Response of A Refractory, Post-Transplantation, Large B-Cell Lymphoma to An Anti-CD22 Immunotoxin", Ann. Intern. Med., 126(11): 882-885, 1997.
Sharma et al. "Molecular Executors of Cell Death-Differential Intrarenal Expression of Fas Ligand, Fas, Granzyme B, and Perforin During Acute and/or Chronic Rejection of Human Renal Allografts", Transplantation, 62(12): 1860-1866, 1996.
Shibata et al. "SCID-Bg Mice as Xenograft Recipients", Laboratory Animals, XP009091838, 31(2): 163-168, Jan. 1, 1997. Figs.4, 5.
Sierra et al. "Liver Gene Expression and Increase in Albumin Synthesis by Fetal Hepatocytes Transplanted Into Analbuminemics Rats", Life Sciences, XP002605656, 67(20): 2417-2432, Oct. 6, 2000. Figs.1-4.
Soria et al. "Insulin-Secreting Cells Derived From Embryonic Stem Cells Normalize Glycemia in Streptozotocin-Induced Diabetic Mice", Diabetes, 49: 1-6, 2000.
Speziali et al. "Cardiac Transplantation for End-Stage Congenital Heart Defects: The Mayo Clinic Experience", Mayo Clinic Proceedings, 73(10): 923-928, 1998.
Stamm et al. "Autologous Bone-Marrow Stem-Cell Transplantation for Myocardial Regeneration", The Lancet, Research Letters, 361: 45-46, 2003.
Steurer et al. "Ex Vivo Coating of Islet Cell Allografts With Murine CTLA4/Fc Promotes Graft Tolerance", Journal of Immunology, XP002031135, 155(3): 1165-1174, Aug. 1, 1995. Fig.8.
Strauer et al. "Intrakoronare, Humane Autologe Stammzelltransplantation zur Myokardregeneration nach Herzinfarkt", Deutsche Medizinische Wochenschrift, 126: 932-938, 2001.
Strauer et al. "Repair of Infarcted Myocardium by Autologous Intracoronary Mononuclear Bone Marrow Cell Transplantation in Humans", Circulation: 106: 1913-1918, 2002.
Subramanian "Cell Transplantation for the Treatment of Parkinson's Disease", Seminars in Neurology, 21(1): 103-115, 2001.
Suthanthiran et al. "Renal Transplantation", The New England Journal of Medicine, 331(6): 365-376, 1996.
Tedder et al. "The Selectins: Vascular Adhesion Molecules", The FASEB Journal, 9: 866-873, 1995.
Thomas "The Infusion of Human Fetal Liver Cells", Stem Cells, XP002605658, 11(Suppl.1): 66-71, 1993. & Conference Celebrating the 40th Anniversary of the Institute of Hematology and Blood Transfusion, Prague, Czech Republic, Oct. 23-24, 1992.
Thomson et al. "Embryonic Stem Cell Lines Derived From Human Balstocysts", Science, 282: 1145-1147, 1998.
Toungouz et al. "Hematopoietic Stem Cells: Therapeutic Applications in Autoimmune Diseases and in Solid Organ Transplantation", Advances in Nephrology, 31(Chap.18): 257-272, 2001.
Touraine et al. "The Place of Fetal Liver Transplantation in the Treatment of Inborn Errors of Metabolism", Journal of Inherited Metabolic Disease, 14(4): 619-626, 1991.
Turner et al. "In Utero Transplantation of Human Fetal Haemotopoietic Cells in NOD/SCID Mice", British Journal of Haematology, XP002941795, 103: 326-334, Jan. 1, 1998.
Van Thiel et al. "Liver Transplantation for Fulminant Hepatic Failure", Journal of Gastroenterology, 36: 1-4, 2001.
Vermeulen et al. "Quantification of Angiogenesis in Solid human Tumours: An International Consensus on the Methodology and Criteria of Evaluation", European Journal of Cancer, 32A(14): 2474-2484, 1996.
Vincenti et al. "Inerleukin-2-Receptor Blockade With Daclizumab to Prevent Acute Rejection in Renal Transplantation", The New England Journal of Medicine, 338(3): 161-166, 1998.
Westermann et al. "Immunoarchitecture of Regenerated Splenic Transplants: Influence of Donor and Host Age on the Regeneration of Splenic Compartments", Cell and Tissue Research, XP009153789, 254(2): 403-413, Nov. 1988. Fig.6.
Woolf "The Kidney: 1. Embryology", Pediatric Nephrology, 4th Ed., Section I(Chap.1): 1-19, 1999.
Worman "What is Primary Biliary Cirrhosis (PBC)?", Columbia University Medical Center, Gastroenterology, 2 P., 2004. http://www.cumc.columbia.edu/dept/giPBC.html, 2004.
Xie et al. "Expression, Roles, Receptors, and Regulation of Osteopontin in the Kidney", Kidney International, 60: 1645-1657, 2001.
Yoon et al. "Differentiation and Expansion of Beta Cell Mass in Porcine Neonatal Pancreatic Cell Clusters Transplanted Into Nude Mice", Cell Transplantation, XP008005474, 8(6): 673-689, Nov. 1, 1999. Abstract. Fig.10.
Zuo et al. "Gene Expression Analysis Reveals Matrilysin as A Key Regulator of Pulmonary Fibrosis in Mice and Humans", Proc. Natl. Acad. Sci. USA, 99(9): 6292-6297, 2002.
Communication Pursuant to Article 94(3) EPC Dated Jun. 29, 2011 From the European Patent Office Re.: Application No. 05796118.7.

(56) References Cited

OTHER PUBLICATIONS

Dekel et al. "Human and Porcine Early Kidney Precursors as a New Source for Transplantation", Nature Medicine, 9(1): 53-60, Jan. 1, 2003.

Eventov-Friedman et al. "Embryonic Pig Liver, Pancreas, and Lung as a Source for Transplantation: Optimal Organogenesis Without Teratoma Depends on Distinct Time Windows", Proc. Natl. Acad. Sci. USA, 102(8): 2928-2933, Feb. 22, 2005.

Eventov-Friedman et al. "Embryonic Pig Pancreatic Tissue Transplantation for the Treatment of Diabetes", PLoS Medicine, 3(7/e215): 1165-1177, Jul. 2006.

Otonkoski et al. "Differentiation and Maturation of Porcine Fetal Islet Cells In Vitro and After Transplantation", Transplantation, 68(11): 1674-1683, Dec. 15, 1999.

Rogers et al. "Islet Cell Engraftment and Control of Diabetes in Rats After Transplantation of Pig Anlagen", American Journal of Physiology: Endocrinology and Metabolism, 286(4): E502-E509, Apr. 1, 2004.

Fig. 9a
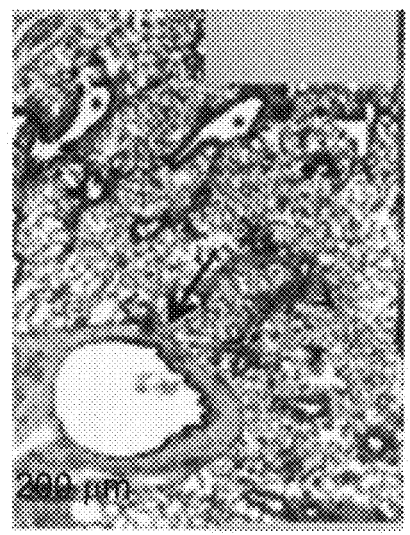
Fig. 9b
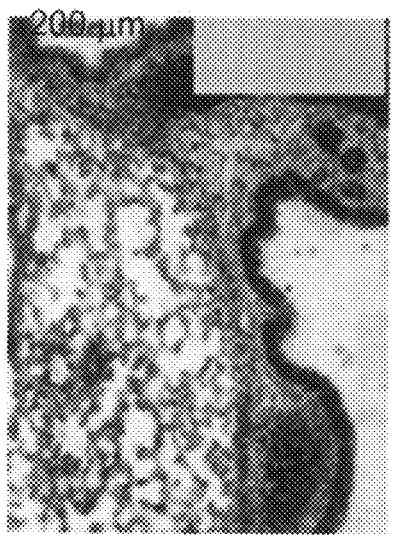
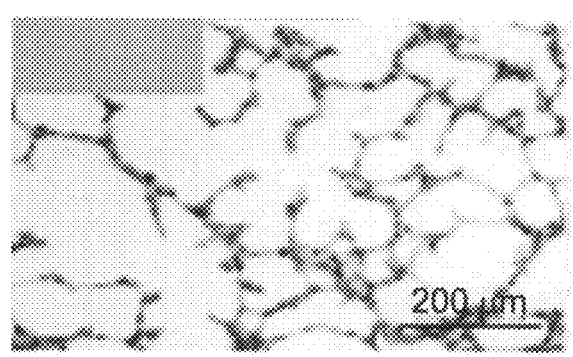
Fig. 9d
Fig. 9c
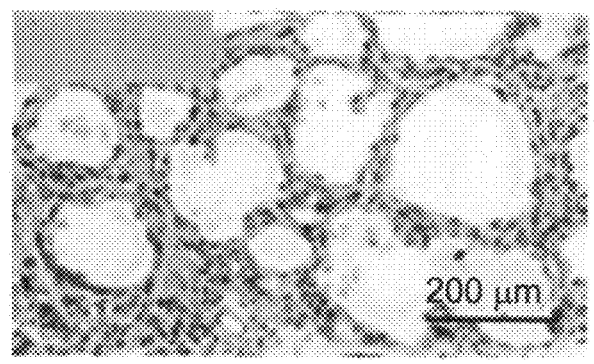
Fig. 9e

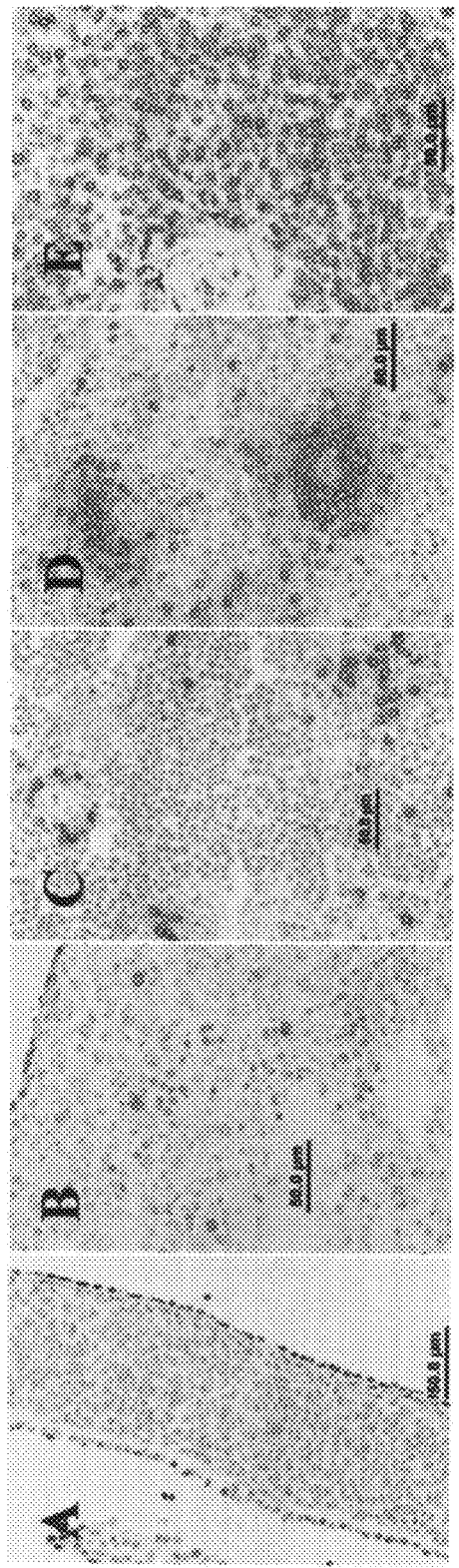

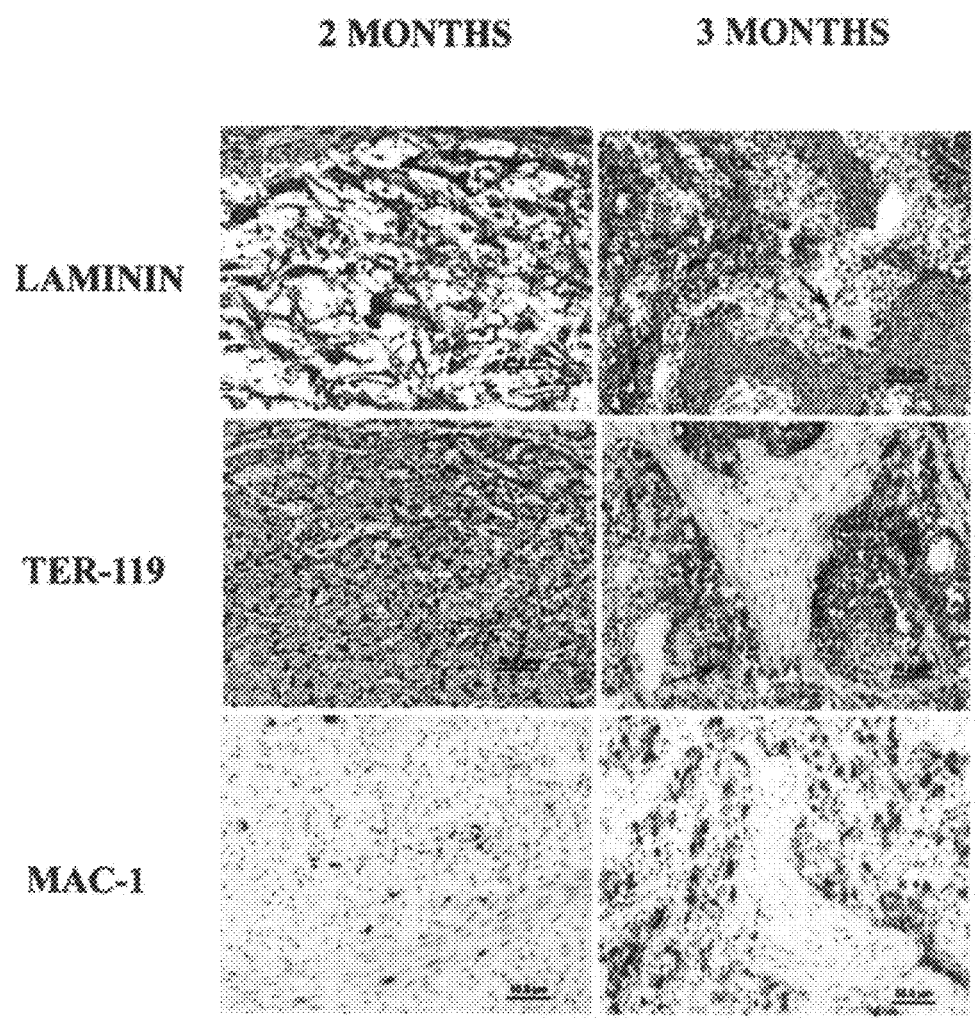

ial Filing

SEQUENCE LISTING

```
<160> NUMBER OF SEQ ID NOS: 6

<210> SEQ ID NO 1
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 1
catggacctg cttcac                                                     16

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
tgacacatga tttaatcccg                                                 20

<210> SEQ ID NO 3
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 3
tgtggcagct cagaat                                                     16

<210> SEQ ID NO 4
<211> LENGTH: 17
<212> TYPE: DNA
<213> ORGANISM: Artificial sequence
<220> FEATURE:
```

-continued

```
<223> OTHER INFORMATION: Single strand DNA oligonucleotide

<400> SEQUENCE: 4
accgatgtgg ttactcc                                                  17

<210> SEQ ID NO 5
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 5
ctgcgacttc aacagc                                                   16

<210> SEQ ID NO 6
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 6
ggtgcagcga actttat                                                  17
```

DISEASE TREATMENT VIA DEVELOPING NON-SYNGENEIC GRAFT TRANSPLANTATION

RELATED APPLICATIONS

This Application is a National Phase of PCT Patent Application No. PCT/IL2005/001059 having International Filing Date of Oct. 2, 2005, which claims the benefit of priority of Israel Patent Application No. 165425 filed on Nov. 28, 2004, now abandoned, and U.S. Provisional Patent Application No. 60/614,968 filed on Oct. 4, 2004. The contents of the above Applications are all incorporated herein by reference. This A is also a Continuation-in-Part (CIP) of U.S. patent application Ser. No. 11/037,025 filed on Jan. 19, 2005, now U.S. Pat. No. 7,780,993 issued on Aug. 24, 2010, which is a Continuation-in-Part (CIP) of U.S. patent application Ser. No. 10/759,033 filed on Jan. 20, 2004, now abandoned, which is a Continuation-in-Part (CIP) of U.S. patent application Ser. No. 10/379,725 filed on Mar. 6, 2003, now abandoned.

FIELD AND BACKGROUND OF THE INVENTION

The present invention relates to methods of providing organ/tissue-specific functions to a subject by transplantation of developing organs. More particularly, the present invention relates to methods of treating pancreatic, hematological/metabolic and pulmonary diseases in mammals by transplantation of developing xenogeneic/allogeneic porcine/human pancreatic, lymphoid/hematopietic or pulmonary organs/tissues, respectively.

Pancreatic diseases such as diabetes, hematological/metabolic diseases such as hemophilia A and Gaucher disease, and pulmonary diseases such as lung failure are diseases of great medical and economic impact for which no satisfactory/optimal treatments are available.

Diabetes is a debilitating and potentially lethal disease that develops in nearly 5 percent of the world's population. In the United States alone, an estimated 18 million people have diabetes mellitus, and each year about 1 million Americans aged 20 or older are diagnosed with the disease. It is the sixth leading cause of death in the US and is responsible for over 200,000 deaths a year. People with diabetes have a shortage of insulin or a reduced ability to use insulin, the hormone regulates blood glucose levels. In mammals the pancreas is responsible for the production and secretion of insulin. The standard therapy for diabetes, daily injections of insulin, does not satisfactorily prevent the debilitating and lethal consequences of this disease.

Pulmonary failure is a highly debilitating and potentially lethal affliction which can arise from numerous types of diseases, including cystic fibrosis, emphysema, pulmonary fibrosis or pulmonary hypertension. While lung transplantation may be employed as a last resort for treating such diseases, there is an insufficient supply of donor organs, with one quarter of the candidates dying on the waiting list and the limit for inscription being often set at 60 years of age. Postoperative mortality at two months is about 15 percent and is related to graft dysfunction, infection, bronchial complications. Five-year survival is still only about 50 percent.

The genetic defect causing hemophilia A affects about one in every 10,000 males. Due to the resultant clotting deficiency, those afflicted with the disease suffer severe bleeding episodes due to small injuries, internal bleeding, and joint hemorrhage, which leads to arthropathy, the major cause of morbidity in hemophilia. Normal levels of factor VIII average between 50 to 200 ng/ml of blood plasma (Mannucci, P. M. in Practical Laboratory Hematology, ed. Koepke, J. A., Churchill Livingstone, N.Y., pp: 347-371, 1990); however, patients suffering from mild to moderate hemophilia A typically have plasma levels well below 2-60 ng/ml, while levels below about 2 ng/mL result in severe hemophilia.

Treatment of hematological/metabolic diseases such as hemophilia A and Gaucher disease is generally effected via enzyme replacement therapy. However, enzyme replacement therapy has numerous significant disadvantages, including the need to administer the replacement enzyme via injection, a painful, inconvenient, and expensive process. The discontinuous dose administration of a replacement enzyme furthermore fails to achieve continuously adjusted physiological levels of the enzyme according to physiological need, as would be achieved by a normal enzyme producing cell population. Thus, enzyme replacement therapy of hematological/metabolic diseases fails in many cases to achieve satisfactory/optimal disease treatment.

Transplantation of fully differentiated haplotype-matched pancreatic or pulmonary grafts from postgestational stage donors is a life-saving, medical procedure of choice for replacing injured or diseased organs such as pancreas or lung. Such a treatment modality, however, suffers from considerable disadvantages. Allogeneic transplantation of differentiated pancreatic or pulmonary organs/tissues is impossible to implement in a great many cases due to the unavailability of suitable immunologically matched transplant donors. Furthermore, use of human donors to provide organs/tissues for transplantation often presents health risks and ethical dilemmas. Thus, large numbers of patients who would otherwise benefit from therapeutic transplantation succumb to diseases associated with pancreatic or pulmonary failure while awaiting matched transplant donors. Moreover, even when suitably haplotype matched transplant donors are found, permanent and harmful immunosuppressive treatments, such as daily administration of cyclosporin A, are generally required to prevent graft rejection. Use of drugs such as cyclosporin A may be undesirable but the benefit of a life saving transplant outweigh the risk of immunosuppressive treatment. Immunosuppressive therapy nevertheless is highly undesirable since these cause severe side effects such as carcinogenicity, nephrotoxicity and increased susceptibility to opportunistic infections. Immunosuppressive treatments contribute to the drawbacks of allogeneic transplantation since these are often unsuccessful in preventing rejection in the short term, and are generally incapable of preventing rejection in the long term. Acute rejection of transplanted grafts is often fatal.

An alternative to allograft transplantation involves xenograft transplantation, i.e., transplantation of animal-derived grafts, in particular porcine grafts, which are well established as a potential animal alternative to human grafts. The great advantages of using xenografts for transplantation are their availability on demand to all patients in need of transplantation, as well as avoidance of the medical and ethical burden of harvesting grafts from live or cadaveric human donors. However, to date, xenogeneic organ/tissue grafts have been ruled out for human transplantation due to their heretofore insurmountable immunological incompatibility with human recipients.

A potentially effective strategy for treating diseases resulting from or associated with abnormal activity of at least one biomolecule (e.g., monogenic, hematological, metabolic diseases) such as hemophilia A and Gaucher disease would involve non-syngeneic donor transplantation of lymphoid tissues/organs, such as spleen, which are potentially capable of generating therapeutic levels of different gene products such as factor VIII or glucocerebrosidase which are respectively deficient in such diseases. As described above, however, the state of the art of therapeutic transplantation generally remains associated with critical disadvantages.

Thus, in view of the unique potential curative benefits of transplantation therapy, there is clearly an urgent and long-standing need for non-syngeneic donor-derived pancreatic, pulmonary and lymphoid/hematopietic organs/tissues which can be obtained in sufficient quantities, and which are optimally tolerated immunologically, so as to render feasible the routine and optimally effective therapeutic transplantation of such organs/tissues.

One strategy, which has been proposed to fulfill this aim involves using gestational stage grafts for transplantation. Such an approach is promising since it has been shown that immunological tolerance to grafts derived from gestational stage tissue is better than that to grafts derived from adult stage tissues (Dekel B. et al., 1997. Transplantation 64, 1550; Dekel B. et al., 1997. Transplantation 64, 1541; Dekel B. et al., 1999. Int Immunol. 11, 1673; Hammerman M R., 2000. Pediatr Nephrol. 14, 513). Furthermore, the enhanced growth and differentiation potential of gestational stage grafts relative to differentiated grafts is highly desirable for generating optimally functional, host integrated grafts. For example, fetal pancreatic islet cells, such as insulin producing beta cells, display enhanced cell growth and differentiation relative to differentiated islet beta cells.

The potential of gestational stage porcine renal (Dekel B. et al., 2003. Nat Med 9:53-60; Hammerman M R., 2004. Am J. Transplant. 4 Suppl 6:14-24), pancreatic (Korsgren O. et al., 1991. Diabetologia 34:379-86; Beattie G M. et al., 1997. Diabetes 46:244-8; Fox A. et al., 2002. Xenotransplantation 9:382-92; Korbutt G S. et al., 1996. The Journal of Clinical Investigation 97:2119-29; Amaratunga A. et al., 2003. Xenotransplantation 10:622-7), hepatic (Kokudo N. et al., 1996. Cell Transplantation 5:S21-2; Takebe K. et al., 1996. Cell Transplant 5:S31-3), neuronal (Larsson L C. et al., 2001. Exp Neurol 172:100-14; Larsson L C. et al., 2003. Transplantation 75:1448-54; Armstrong R J. et al., 2002. Exp Neurol 175:98-111) grafts to generate functional organs/tissues following transplantation into non-syngeneic hosts has been extensively described. The potential of gestational stage human pulmonary (Angioi K. et al., 2002. The Journal of Surgical Research 102:85-94), cardiac or intestinal grafts (Angioi K. et al., 2002. The Journal of Surgical Research 102:85-94; Lim F Y. et al., 2003. Journal of Pediatric Surgery 38:834-9) to generate organs/tissues having organ-specific function following transplantation into non-syngeneic hosts has also been demonstrated.

Thus, various approaches have been described in the prior art for using developing pancreatic organ/tissue grafts for therapeutic transplantation.

For example, it has been shown that human fetal islets including the earliest insulin secreting cells, transplanted into nude mice and rats display continued growth and development, including production of the other pancreatic hormones: glucagon, somatostatin, and pancreatic polypeptide (Usadel et al., 1980. Diabetes 29 Suppl 1:74-9). Similarly, it has been shown that human embryonic pancreas-derived grafts transplanted into NOD/SCID mice, generated graft-derived insulin producing human beta-cells (Castaing M. et al., 2001. Diabetologia 44:2066). Gestational stage porcine islet transplants in mice may display a similar differentiation program, with similar timing, as the normal non-transplanted tissues.

Other examples include transplantation of gestational stage porcine islet cells in nude mice (Korsgren O. et al., 1991. Diabetologia 34:379-86; Otonkoski T. et al., 1999. Transplantation 68, 1674), of fetal pancreas in immunodeficient rodents (Fox A. et al., 2002. Xenotransplantation 9:382-92; Amaratunga A. et al., 2003. Xenotransplantation 10:622-7), of human fetal islets in nude mice and rats (Beattie G M. et al., 1997. Diabetes 46:244-8;) and of porcine fetal islet tissue into nude mice (Korbutt G S. et al., 1996. J Clin Invest. 97:2119-29). Another approach involves transplantation of fetal porcine islet-like cell clusters into cynomolgus monkeys (Soderlund J. et al., 1999. Transplantation 67:784-91). Still another approach involves intratesticular transplantation of neonatal porcine islets into non-immunosuppressed beagles (Gores P F. et al., 2003. Transplantation 75:613-8).

Additionally, attempts to transplant porcine fetal pancreatic tissues in diabetic human recipients have been made (Groth C G. et al., 1998. Transplantation Proceedings 30:3809-10; Groth C G. et al., 1999. J Mol. Med. 77, 153; Reinholt F P. et al., 1998. Xenotransplantation 5:222-5; Korsgren O. et al., 1992. Transplantation Proceedings 24:352-3; Groth C G. et al., 1994. Lancet 344:1402-4).

US 2003/0198628 to Hammerman discloses a method for pancreas transplantation comprising implanting into a host an embryonic pancreas. In one embodiment the pancreas is harvested from a porcine embryo from about day E20 to about day E38, the most preferred harvest day being about day E29.

US Patent Application Nos. 20040082064 and 20040136972 to some of the inventors of the present application suggest treating pancreatic disease in humans by transplantation of porcine pancreatic organ/tissue grafts at a developmental stage of 20-28 days of gestation, and teach that 27-28 days of gestation is the optimal gestational stage of any type of porcine organ/tissue grafts for therapeutic transplantation.

Various prior art approaches have been described in the prior art for using developing pulmonary organ/tissue grafts for therapeutic transplantation.

In one approach, human pulmonary grafts at a gestational stage of 6-10 weeks were transplanted into immunodeficient mice (Angioi K. et al., 2002. The Journal of Surgical Research 102:85-94).

In another approach, lung fragments from human fetuses at 10 to 14 weeks of gestation were transplanted into immunodeficient mice (Groscurth P, Tondury G., 1982. Anat Embryol (Berl). 165:291-302).

Regarding transplantation of lymphoid/hematopietic organ/tissue grafts, US Patent Publication No. 20040136972 to some of the inventors of the present application asserts that all types of porcine organ/tissue grafts at a developmental stage of 27-28 days, specifically including splenic organ/tissue grafts, are optimal for therapeutic transplantation.

However, all previous approaches involving transplantation of developing non-syngeneic pancreatic, pulmonary or lymphoid/hematopietic organs/tissues suffer from some or all of the following drawbacks:

(i) suboptimal tolerance by non-syngeneic host lymphocytes;

(ii) suboptimal structural and functional graft differentiation, for example with respect to insulin production by pancreatic organ/tissue grafts;

(iii) predominantly graft-derived, as opposed to host-derived, graft vascularization, thereby leading to immune rejection;

(iv) suboptimal growth;

(v) inadequate availability of transplantable organs/tissues; and/or (vi) suboptimal safety for human administration, notably with respect to avoidance of generation of graft-derived teratomas.

Previous approaches employing developing non-syngeneic grafts have been uniformly suboptimal since the optimal gestation time for implantation based on risk for teratoma, growth potential and immunogenicity, all of which might vary between different organs in fetal development, was not sufficiently characterized.

There is thus a widely recognized need for, and it would be highly advantageous to have, a method of treating human diseases amenable to therapeutic transplantation by transplantation of developing non-syngeneic pancreatic, pulmonary or lymphoid/hematopietic organs/tissues devoid of the above limitations.

SUMMARY OF THE INVENTION

The present invention discloses the use of non-syngeneic developing pancreatic, lymphoid and pulmonary grafts for disease treatment. This use can be effected in a variety of ways as further described and exemplified hereinbelow.

The present invention is based on the unexpected discovery of suitable time windows for successful transplantation of non-syngeneic developing pancreatic, pulmonary or lymphoid/hematopietic organs/tissues. It is presently disclosed for the first time that non-syngeneic pancreatic organ/tissue grafts, such as xenogeneic porcine grafts, at a developmental stage essentially corresponding to that of porcine pancreas at a gestational stage of 42 to 56 days of gestation are optimal for growth and development of insulin-producing pancreatic organs/tissues. It is further presently further disclosed for the first time that lymphoid/hematopietic organ/tissue grafts, such as xenogeneic porcine lymphoid/hematopietic organ/tissue grafts, at a developmental stage essentially corresponding to that of porcine spleen at a gestational stage of 42 to 56 days of gestation are optimal for growth and development of factor VIII-producing pancreatic organs/tissues, and can be used to treat hemophilia A in a mammal. It is yet further presently disclosed for the first time that non-syngeneic pulmonary grafts at a developmental stage essentially corresponding to that of porcine lung at a gestational stage of 56 to 80 days are optimal for growth and differentiation of pulmonary organs/tissues which comprise alveoli.

According to one aspect of the present invention there is provided a method of providing a pancreatic function to a mammalian.

According to still further features in the described preferred embodiments, the pancreatic organ/tissue graft is at a developmental stage essentially corresponding to that of a porcine pancreatic organ/tissue at a gestational stage selected from a range of about 42 to about 80 days of gestation, thereby generating a functional pancreatic organ/tissue for providing the pancreatic function to the subject.

According to further features in preferred embodiments of the invention described below, the pancreatic organ/tissue graft is at a developmental stage essentially corresponding to that of a porcine pancreatic organ/tissue at a gestational stage selected from a range of about 42 to about 56 days of gestation.

According to further features in preferred embodiments of the invention described below, the pancreatic organ/tissue graft is at a developmental stage essentially corresponding to that of a porcine pancreatic organ/tissue at a gestational stage of about 42 days of gestation.

According to still further features in the described preferred embodiments, the pancreatic organ/tissue graft is non-syngeneic with the subject.

According to still further features in the described preferred embodiments, the pancreatic organ/tissue graft is xenogeneic with the subject.

According to still further features in the described preferred embodiments, the pancreatic organ/tissue graft is of porcine origin.

According to still further features in the described preferred embodiments, the subject has an abnormal activity a biomolecule naturally produced by a mammalian pancreas.

According to still further features in the described preferred embodiments, the subject has an abnormal activity a biomolecule naturally produced by a mammalian pancreatic islet.

According to still further features in the described preferred embodiments, the biomolecule is insulin.

According to another aspect of the present invention there is provided a method of providing a pancreatic function to a mammalian subject, the method comprising transplanting into the subject a mammalian pancreatic organ/tissue graft, wherein the pancreatic organ/tissue graft is at a developmental stage essentially corresponding to that of a human pancreatic organ/tissue at a gestational stage selected from a range of about 14 to about 20 weeks of gestation, thereby generating a functional pancreatic organ/tissue for providing the pancreatic function to the subject.

According to yet another aspect of the present invention there is provided a method of generating pulmonary tissue in a mammalian subject in need thereof, the method comprising transplanting into the subject a developing mammalian pulmonary graft, wherein the pulmonary graft is at a developmental stage essentially corresponding to that of a porcine pulmonary organ/tissue at a gestational stage selected from a range of about 42 to about 80 days of gestation, thereby generating pulmonary tissue in the subject.

According to further features in preferred embodiments of the invention described below, the pulmonary graft is at a developmental stage essentially corresponding to that of a porcine pulmonary organ/tissue at a gestational stage selected from a range of about 56 to about 80 days of gestation.

According to still further features in the described preferred embodiments, the pulmonary graft is non-syngeneic with the subject.

According to still further features in the described preferred embodiments, the pulmonary graft is xenogeneic with the subject.

According to still further features in the described preferred embodiments, the pulmonary organ/tissue graft is of porcine origin.

According to still another aspect of the present invention there is provided a method of treating a hemophilia in a mammalian subject in need thereof, the method comprising transplanting into the subject a developing mammalian lymphoid/hematopietic organ/tissue graft, wherein the lymphoid/hematopietic organ/tissue graft is at a developmental stage essentially corresponding to that of a porcine lymphoid/hematopietic organ/tissue at a gestational stage selected from a range of about 42 to about 80 days of gestation, thereby generating a functional lymphoid/hematopietic organ/tissue for treating the hemophilia in the subject.

According to further features in preferred embodiments of the invention described below, the hemophilia is hemophilia A.

According to still another aspect of the present invention there is provided a method of providing a lymphoid/hematopietic organ/tissue function to a human subject, the method comprising transplanting into the subject a developing mammalian lymphoid/hematopietic organ/tissue graft, preferably the lymphoid/hematopietic organ/tissue graft is at a developmental stage essentially corresponding to that of a porcine lymphoid/hematopietic organ/tissue at a gestational stage selected from a range of about 42 to about 80 days of gestation, thereby generating a functional lymphoid/hematopietic organ/tissue for providing the lymphoid/hematopietic organ/tissue function to the subject.

According to further features in preferred embodiments of the invention described below, the lymphoid/hematopietic organ/tissue graft is at a developmental stage at which a lymphoid/hematopietic organ/tissue essentially does not comprise T-cells.

According to still further features in the described preferred embodiments, the lymphoid/hematopietic organ/tissue graft is at a developmental stage essentially corresponding to that of a porcine lymphoid/hematopietic organ/tissue at a gestational stage selected from a range of about 42 to about 56 days of gestation.

According to still further features in the described preferred embodiments, the lymphoid/hematopietic organ/tissue graft is at a developmental stage essentially corresponding to that of a porcine lymphoid/hematopietic organ/tissue at a gestational stage of about 42 days of gestation.

According to still further features in the described preferred embodiments, the lymphoid/hematopietic organ/tissue graft is non-syngeneic with the subject.

According to still further features in the described preferred embodiments, the lymphoid/hematopietic organ/tissue graft is xenogeneic with the subject.

According to still further features in the described preferred embodiments, the lymphoid/hematopietic organ/tissue graft is of porcine origin.

According to still further features in the described preferred embodiments, the subject is human.

According to still further features in the described preferred embodiments, subject has an abnormal activity of a biomolecule naturally produced by a lymphoid/hematopoietic organ/tissue thereof.

According to still further features in the described preferred embodiments, the subject has an abnormal serum concentration of a biomolecule produced by a mammalian liver or lymphoid/hematopietic organ/tissue.

According to still further features in the described preferred embodiments, the subject has an abnormal serum concentration of a clotting cascade factor produced by a mammalian lymphoid/hematopietic organ/tissue.

According to still further features in the described preferred embodiments, the lymphoid/hematopietic organ/tissue graft is derived from a developing lymphoid/hematopietic organ/tissue.

According to still further features in the described preferred embodiments, the lymphoid/hematopietic organ/tissue graft is derived from fetal spleen.

According to still further features in the described preferred embodiments, the method further comprising transiently administering to the subject at least one T-cell costimulation inhibitor and at least one CD40 ligand inhibitor.

According to still further features in the described preferred embodiments, transplanting the graft into the subject is effected by transplanting the graft under at least one renal capsule of the subject.

The present invention successfully addresses the shortcomings of the presently known configurations by providing new developing/non-syngeneic pancreatic, lymphoid/hematopietic or pulmonary organ/tissue grafts which are at stages of development enabling effective/optimal treatment in a recipient thereof of essentially any disease which is amenable to therapeutic transplantation of pancreatic, lymphoid/hematopietic or pulmonary organ/tissue grafts, respectively.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
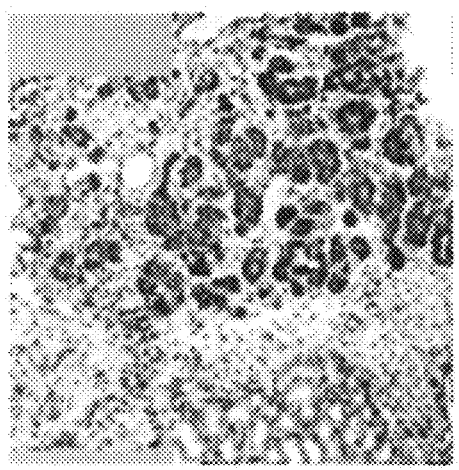
Figure 1B:
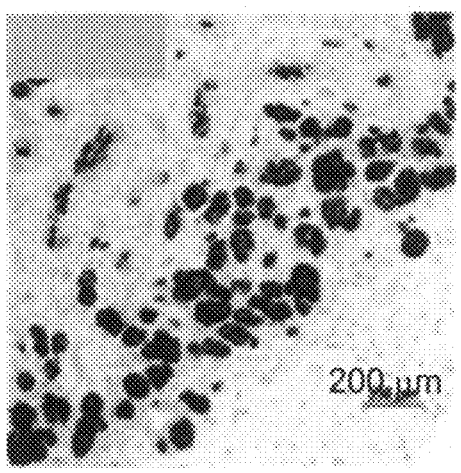
Figure 1C:
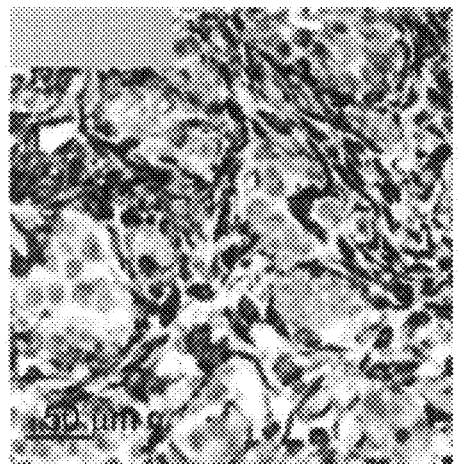
Figure 1D:
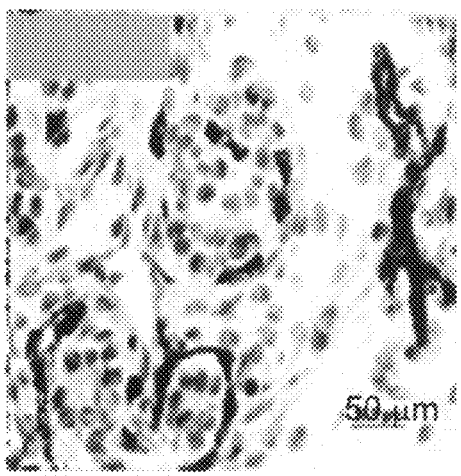
Figure 1E:
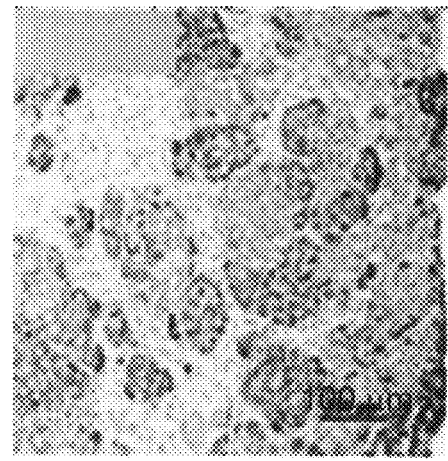
Figure 1F:
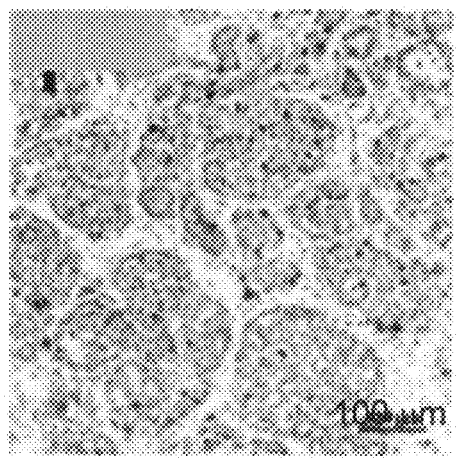

FIGS. 1a-f are photomicrographs depicting histological staining of an E42 porcine pancreas graft 6 weeks after transplantation. H&E staining (FIG. 1a), cytokeratin 20 (FIG. 1b), vimentin (v9) (FIG. 1c), anti-mouse CD31 (FIG. 1d), insulin (FIG. 1e), Ki67 (FIG. 1f).

Figure 2A:
Figure 2B:
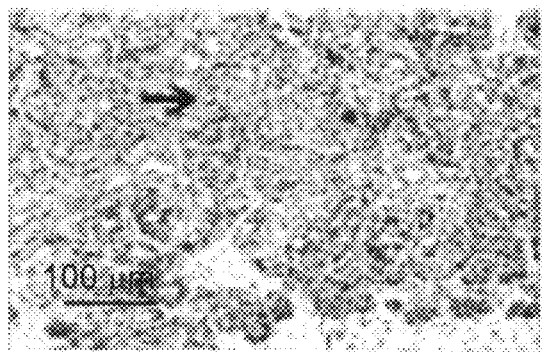
Figure 2C:
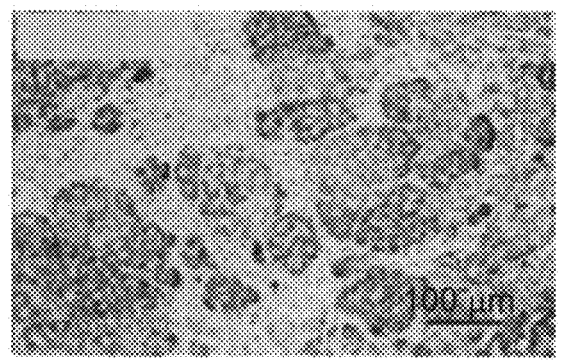
Figure 2D:
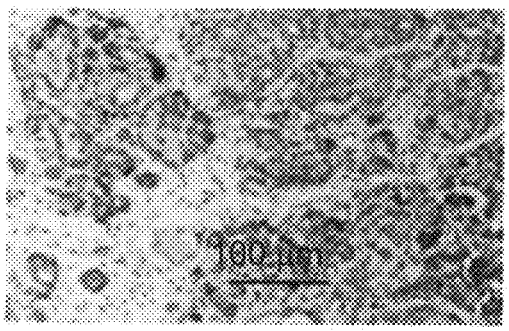
Figure 2E:
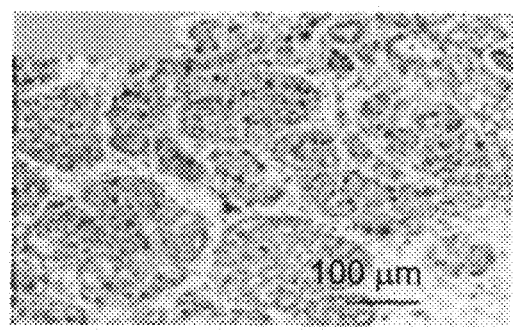

FIGS. 2a-2e are photographs depicting an E56 pancreatic organ/tissue graft 3 months posttransplantation. Shown are the graft and its vasculature (FIG. 2a), H&E staining (FIG. 2b), insulin immunohistochemical staining (FIG. 2c), pancreatic polypeptide immunohistological staining (FIG. 2d), and Ki67 immunohistological staining (FIG. 2e).

Figure 3:
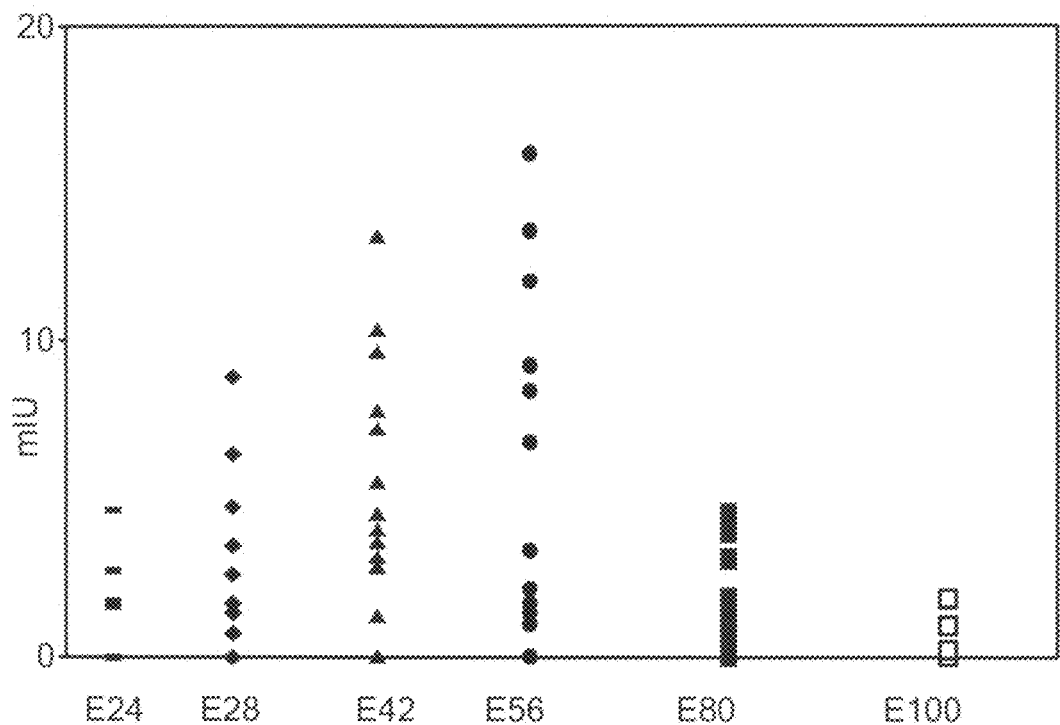
Figure 4A:
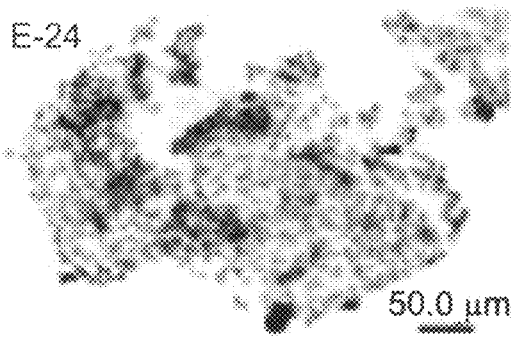
Figure 4B:
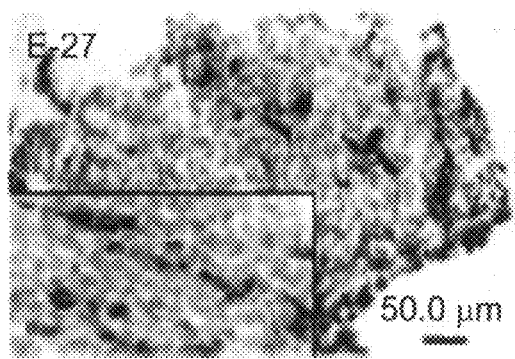
Figure 4C:
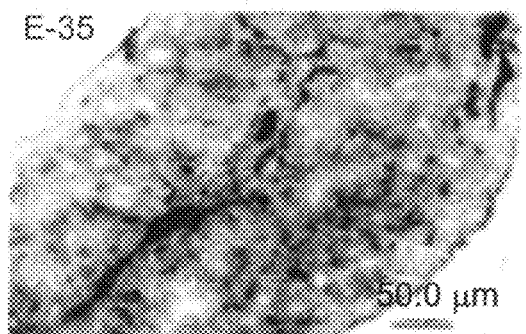
Figure 4D:
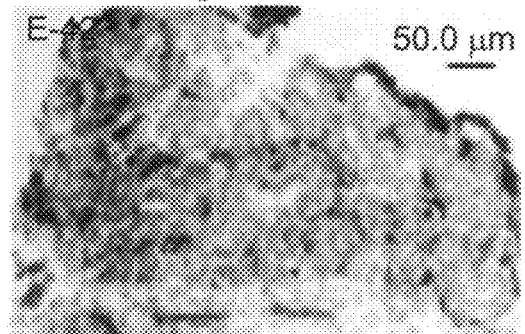
Figure 5A:
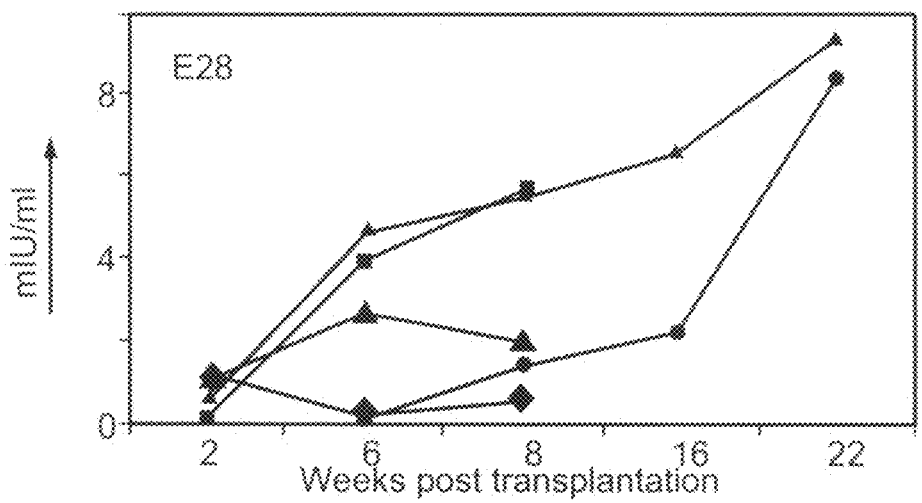
Figure 5B:
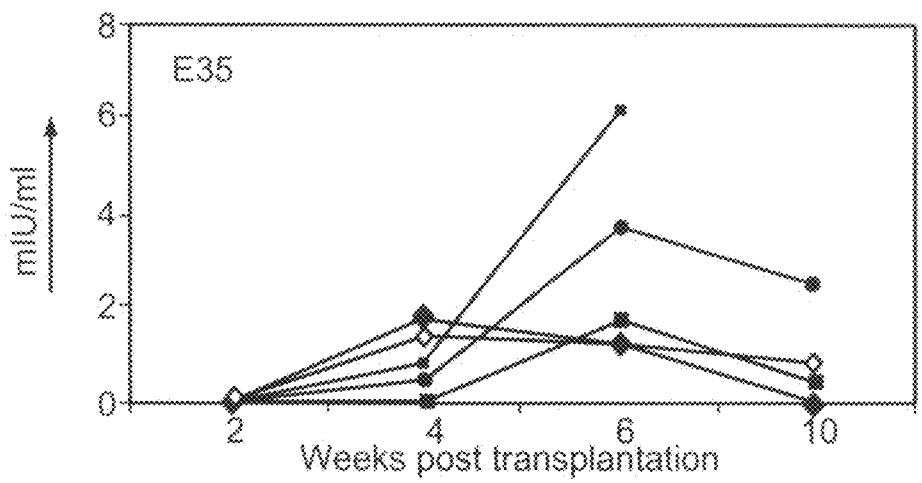
Figure 5C:
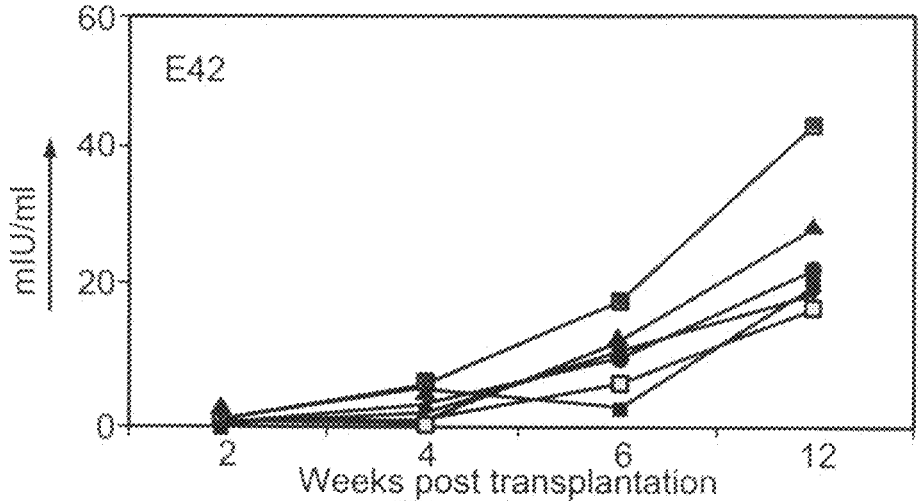
Figure 5D:
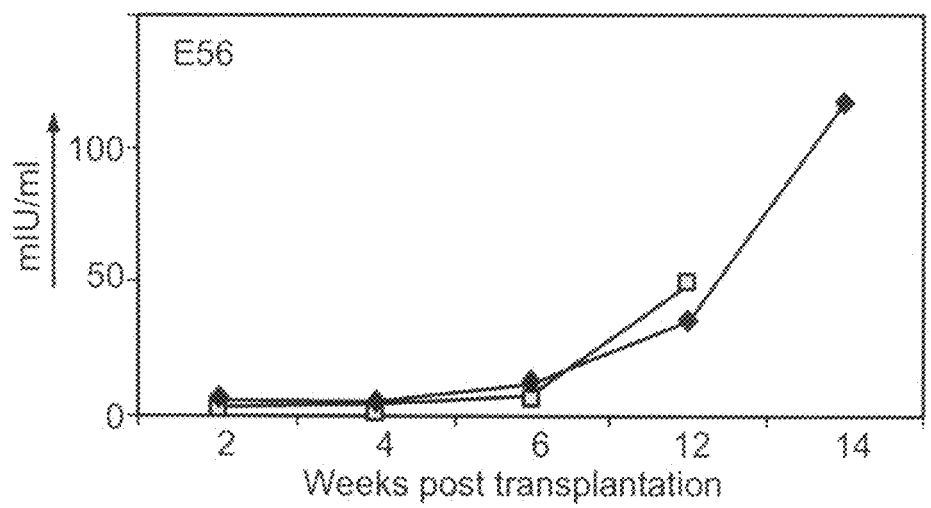

FIG. 3 is a cumulative data plot depicting porcine insulin levels in serum of SCID mice following transplantation of porcine embryonic pancreas. Donor tissue obtained at different gestational ages was implanted under the kidney capsule and serum levels were documented 6 weeks after transplantation as determined by ELISA.

FIGS. 4a-d are photomicrographs depicting immunohistological staining of porcine endothelial cells (lining along blood vessels) marked by CD-31 positive staining (darker staining) in embryonic pancreas at E24, E27, E35 and E42, respectively.

FIGS. 5a-d are graphs depicting the long-term follow-up of porcine insulin levels detected in the serum of NOD-SCID mice following fetal pancreas transplantation from donors of different gestational ages. FIGS. 5a-d respectively depict the insulin levels produced by organs generated from gestational day E28, E35, E42 and E56 porcine pancreas graft donors.

Figure 6:
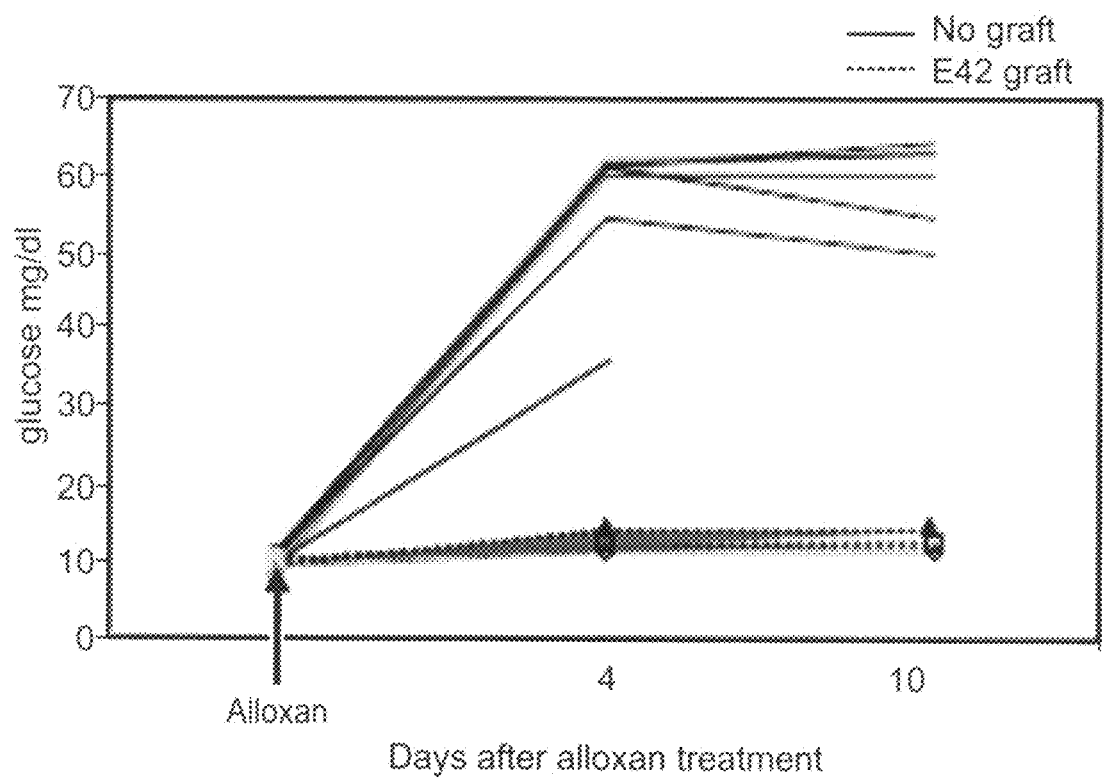

FIG. 6 is a graph depicting the glucose levels in alloxan treated NOD-SCID mice, without a graft (solid lines) and 4 and 10 days posttransplantation of an E42 fetal porcine pancreas graft.

Figure 7A:
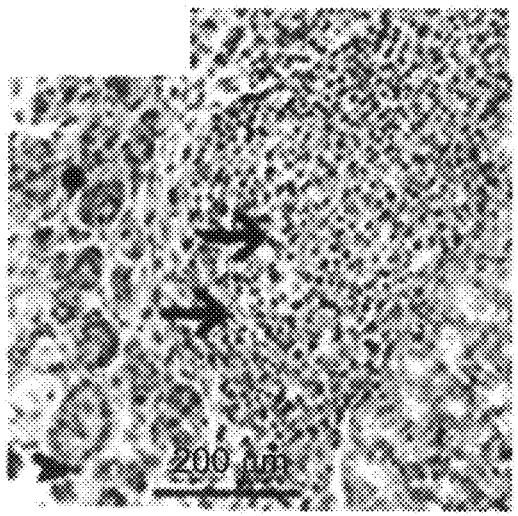
Figure 7B:
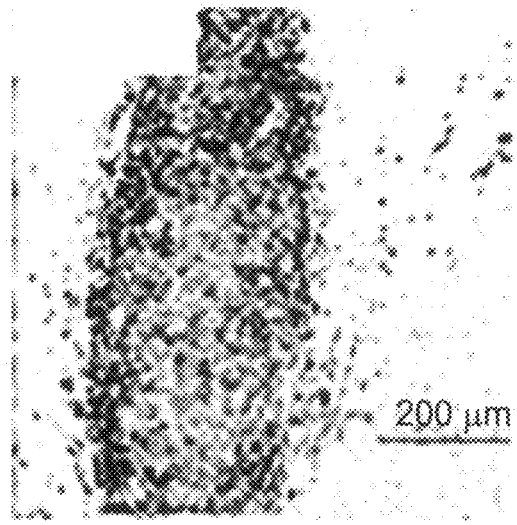
Figure 7C:
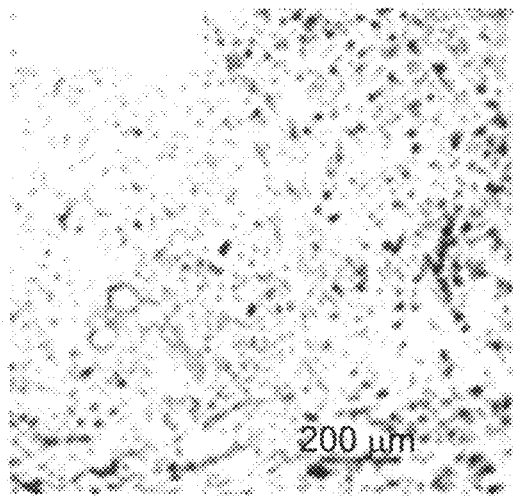
Figure 7D:
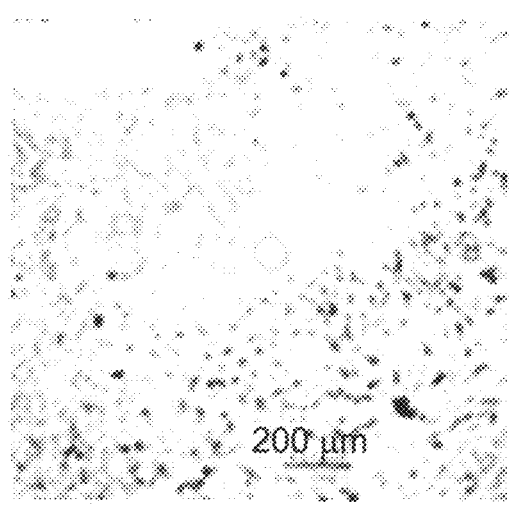

FIGS. 7a-d are histology photomicrographs depicting the level of rejection of porcine embryonic pancreatic tissues (E56 and E80) mediated by human PBMCs, 6 weeks after transplantation under the kidney capsule of NOD-SCID mice. FIG. 7a depicts H&E staining of E56 pig pancreatic tissue. FIG. 7b depicts local infiltration of human PBMCs in the E56 graft stained with anti-human CD45. FIG. 7c depicts H&E staining of E80 pancreatic organ/tissue graft. FIG. 7d depicts human PBMCs stained with anti-human CD45 antibody invading the E80 pancreatic organ/tissue graft.

Figure 8A:
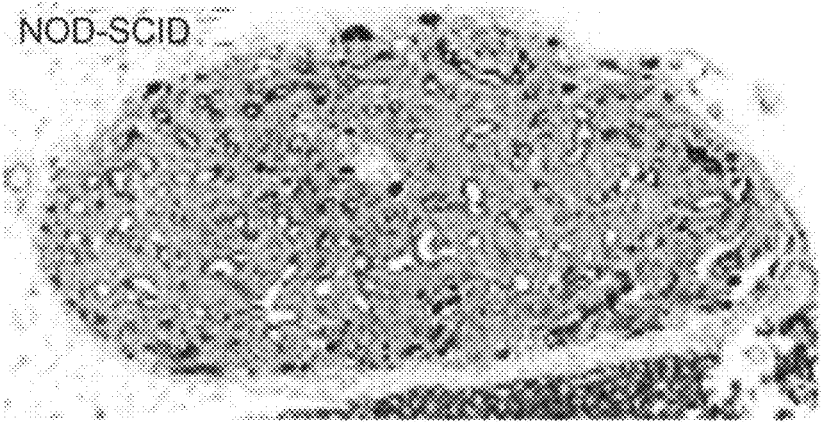
Figure 8B:
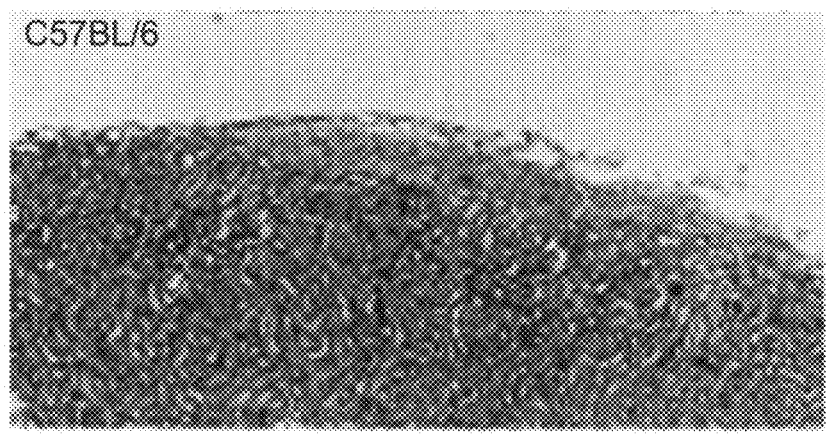
Figure 8C:
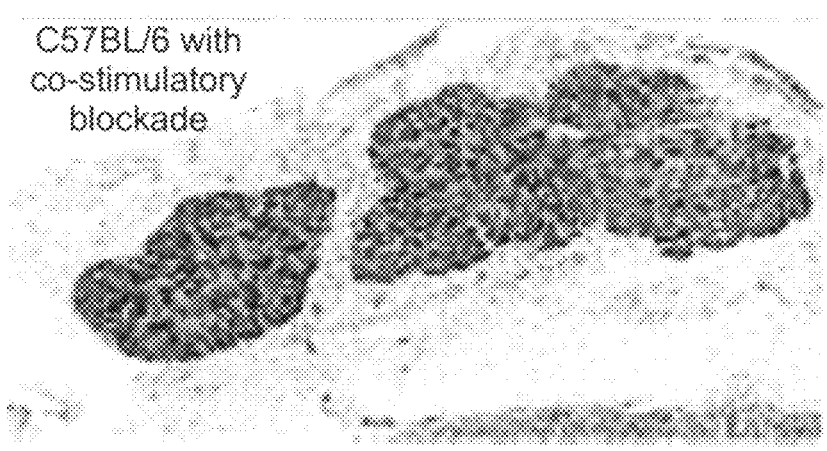

FIGS. 8a-c are photomicrographs depicting histological sections of pancreas tissue (E42) transplanted into immunodeficient and immunocompetent mice. FIG. 8a shows the tissue in a NOD-SCID mouse, FIG. 8b shows the tissue in a C57BL/6 mouse, and FIG. 8c shows the tissue is an immunosuppressed C57BL/6 mouse.

FIGS. 9a-e are photographs depicting development of E56 and E80 porcine lung 6 weeks following implantation under the kidney capsule. FIG. 9a depicting growth of transplanted tissue obtained at E56 is macroscopically illustrated. FIG. 9b depicts stained lung tissue (H&E): respiratory bronchi (arrow), bronchioles (asterisks) and alveoli (arrow heads). FIG. 9c depicts alcian-blue/PAS stained cartilage of E56 lung implants. FIGS. 9d-e depict H&E staining of alveolar wall structure and thickness of E56 and E80 implants, respectively.

Figure 10A:
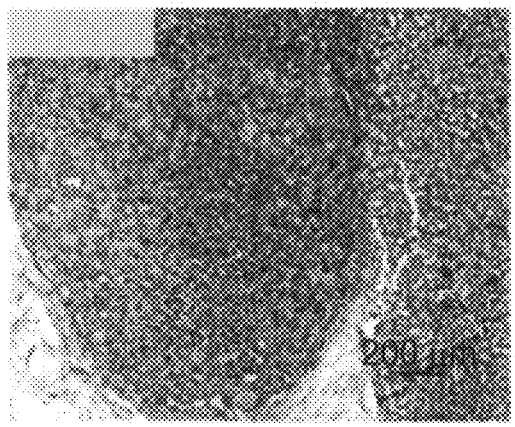
Figure 10B:

FIGS. 10a-b depict immunochemical staining with H&E and anti-vimentin (v9), respectively, of E42 transplanted porcine splenic tissue 6 weeks after transplantation.

Figure 11:
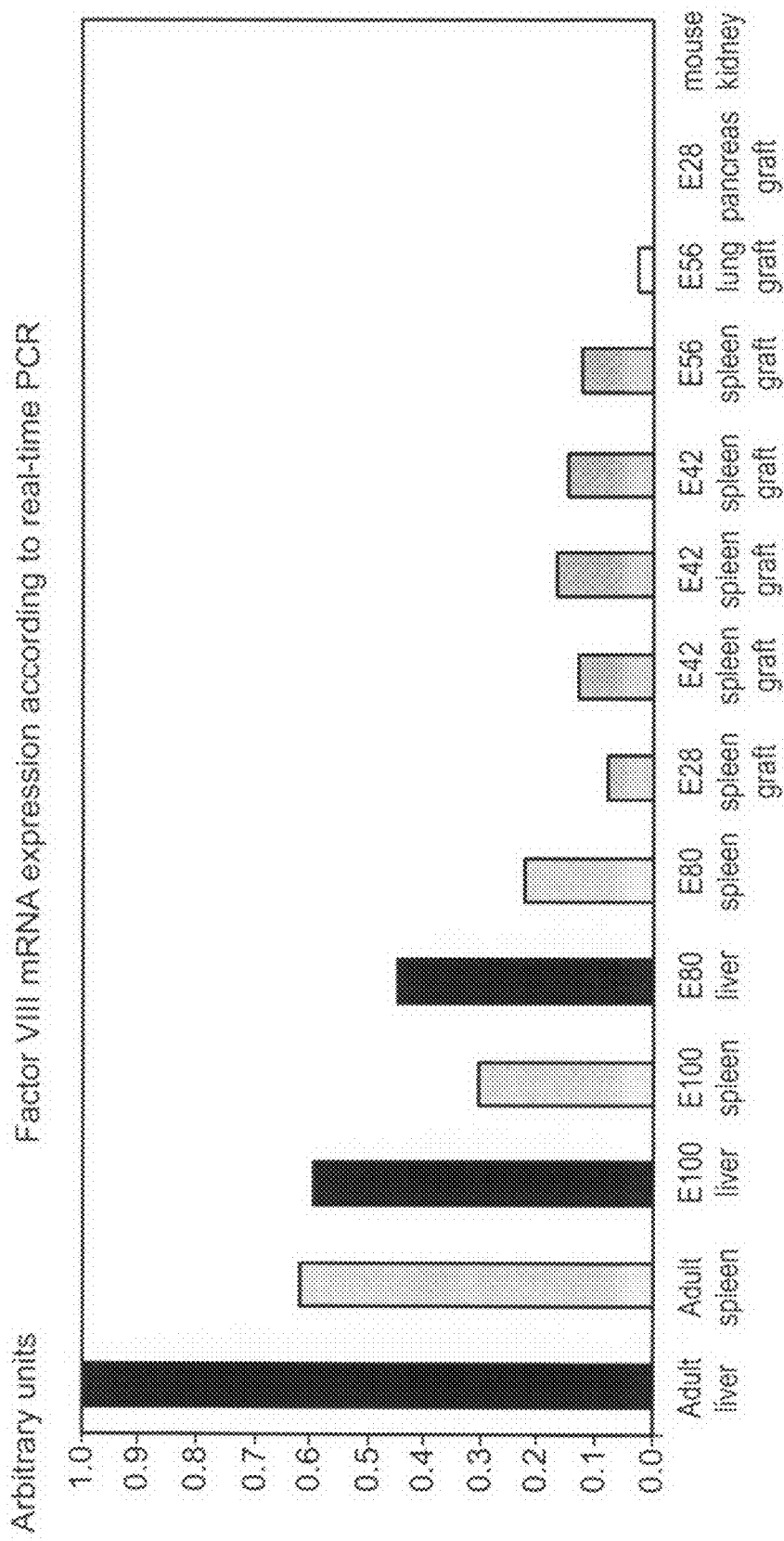

FIG. 11 shows the relative amounts of porcine factor VIII mRNA in different splenic tissues before and after transplantation. Factor VIII levels were evaluated by real-time PCR using primers specific for porcine factor VIII. The results were divided by the expression of the house-keeping gene beta-actin using primers specific for the porcine Beta-actin. Total mRNA that was purified either from adult tissue or from E80 or E100 precursor tissue from porcine liver and porcine spleen served as positive control. Total mRNA that was purified from the mouse kidney, from an area distant from the embryonic implant, served as negative control.

FIGS. 12a-e depict immunohistological staining of pig CD3+ T cells in embryonic pig precursor spleen tissue harvested at E42, E56, E80, E100 and from adult spleen, respectively.

Figure 13A:
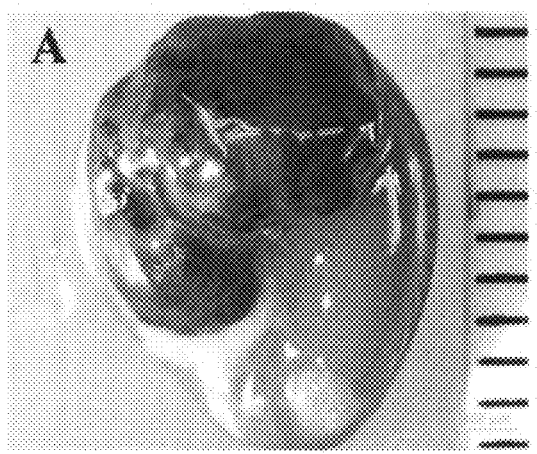
Figure 13B:
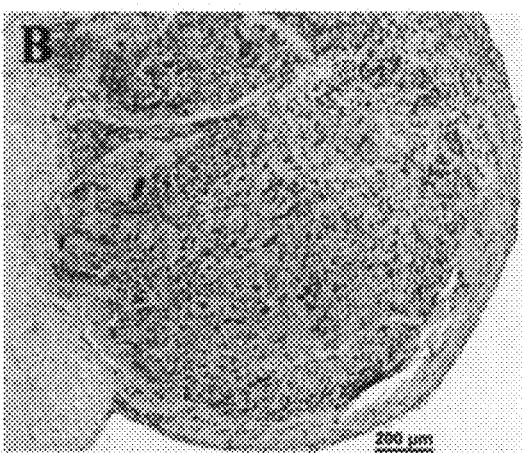
Figure 13C:
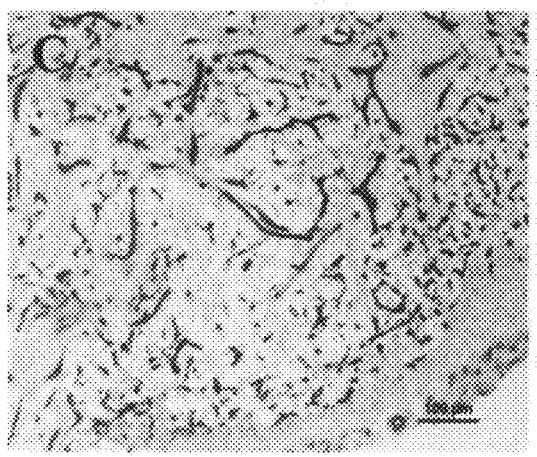

FIGS. 13a-d are photographs depicting development of E42 pig spleen following implantation under the kidney capsule of NOD-SCID mice. FIG. 13 shows E42 macro view. FIG. 13b shows pig mesenchymal components (brown) specifically stained with vimentin (V9). FIG. 13c shows porcine blood vessels, as shown by pig CD31 expression, and proliferative ability is demonstrated by ki67 staining in FIG. 13d.

FIG. 14 is a series of photomicrographs depicting development of hematopoietic nests and fibrous septae in pig E42 spleen implants. At 2 months, a sponge-like fibrous reticular network outlined by anti-laminin antibody (brown) with diffusely entrapped mouse erythroid cells stained by anti-mouse TER 119 (brown) is evident. In contrast, at 3 months posttransplant, dense laminin-positive connective tissue septa is evident, surrounding nests of mouse hematopoietic tissue, including TER-119-positive erythropoietic areas and regions with megakaryocytes (arrow) and myelopoiesis. Host myeloid cells, demonstrated by mouse MAC-1 immunostaining (brown) are rare and diffusely distributed in spleen transplants at 2 months, but become numerous within hematopoietic nests at 3 months following transplant.

Figure 15:
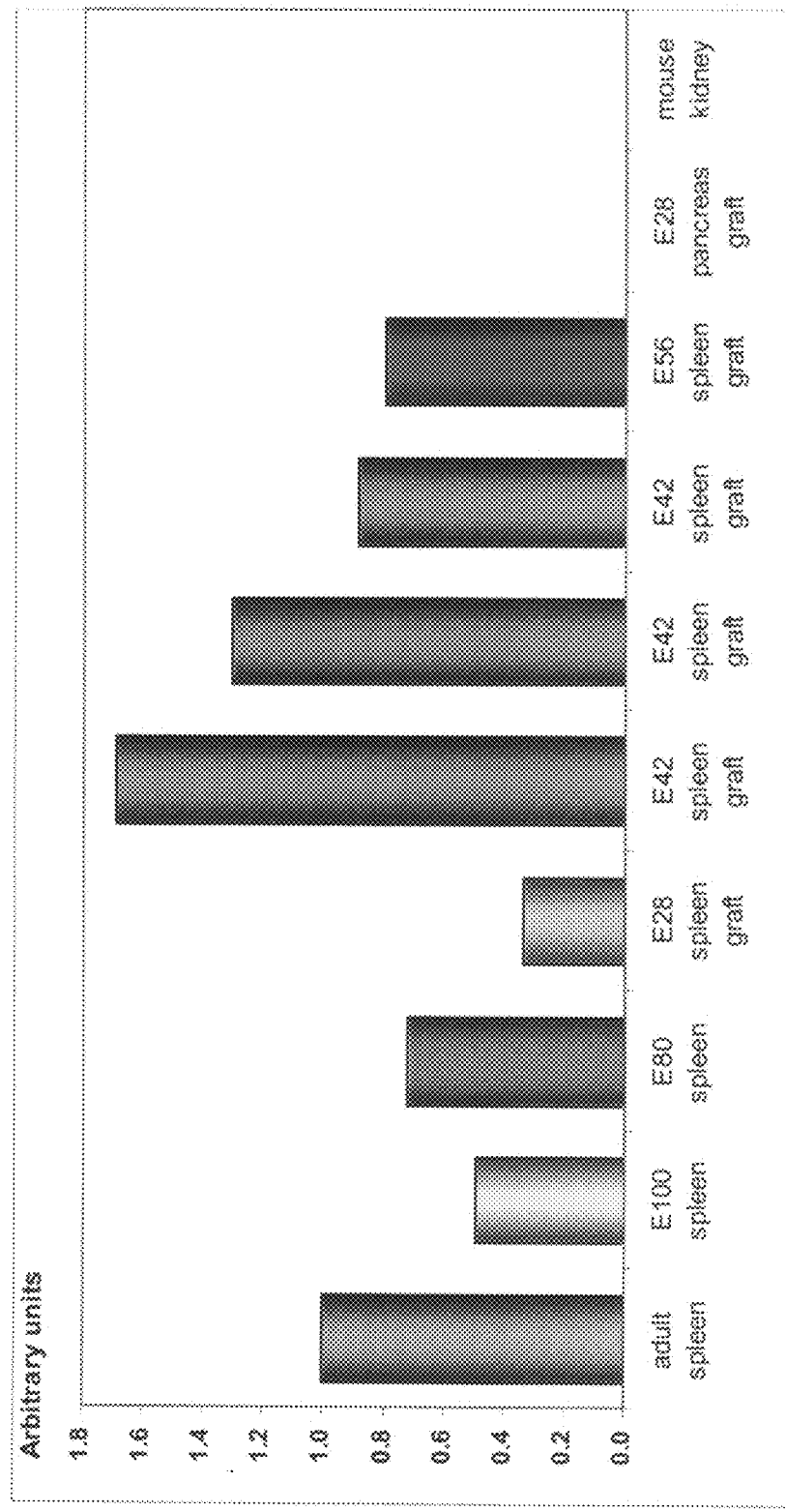

FIG. 15 is a bar-graph depicting the relative amount of pig factor VIII mRNA in different transplanted tissues, as evaluated by RT-PCR using pig factor VIII specific primers. The results were normalized to the expression of the housekeeping gene, transferrin receptor. Pig factor VIII levels in E28, E42 and E56 spleen grafts are shown by orange, green and red columns, respectively. Adult, E100, and E80 spleen precursor tissues prior to transplantation are shown by blue, yellow and purple columns. Total mRNA purified from adult pig spleen (blue column) served as positive control. Total mRNA purified form the mouse kidney, from an area distant from the embryonic implant and from an E28 pancreas graft served as negative controls.

Figure 16:
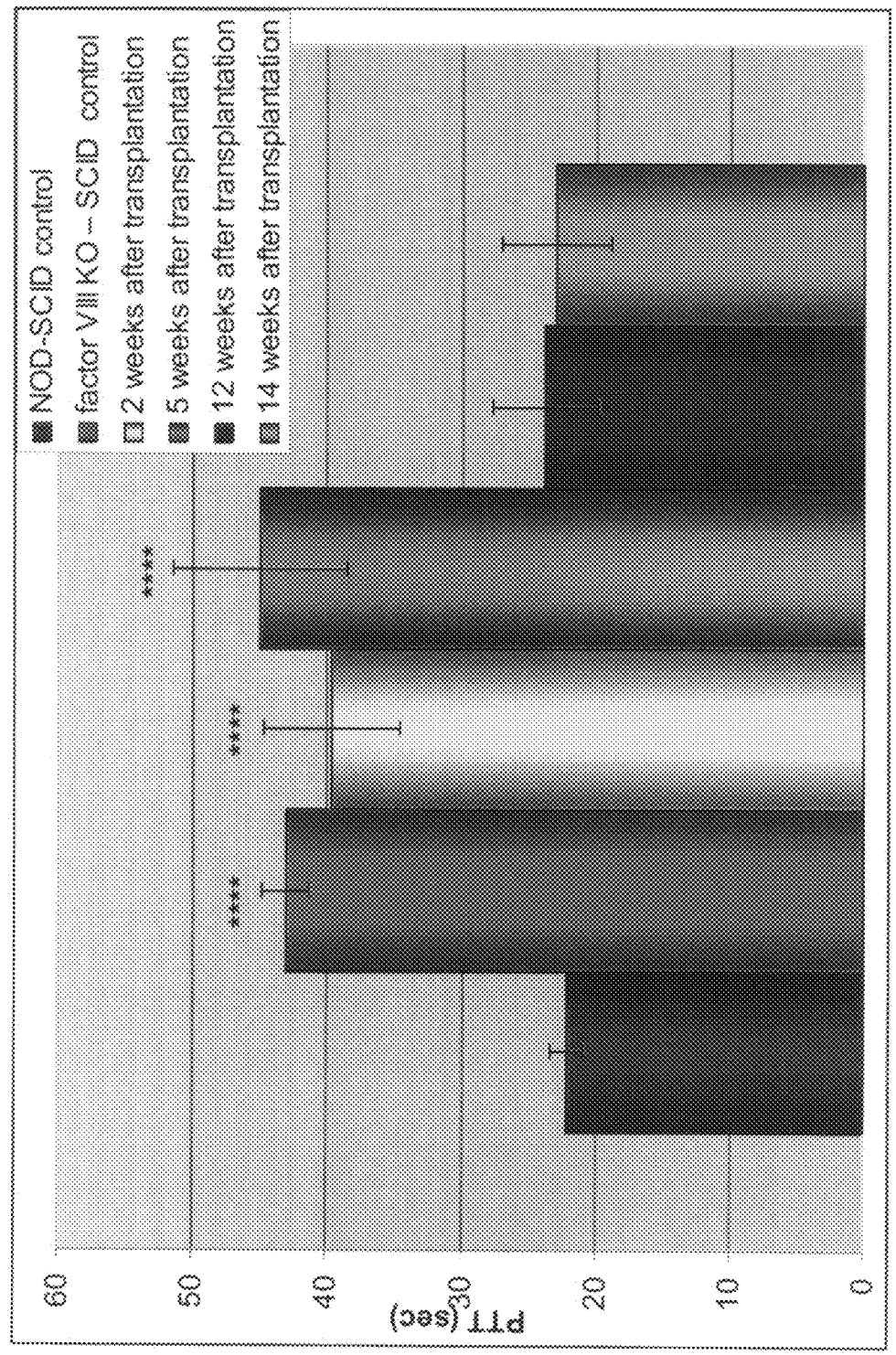

FIG. 16 is a bar-graph depicting PTT values of wild type NOD-SCID control mice, factor VIII KO-SCID control mice and factor VIII KO-SCID mice transplanted with E42 pig spleen, 2, 5, 12 and 14 weeks after transplantation. ****P value=0.0001 (compared to factor VIII KO-SCID).

Figure 17A:
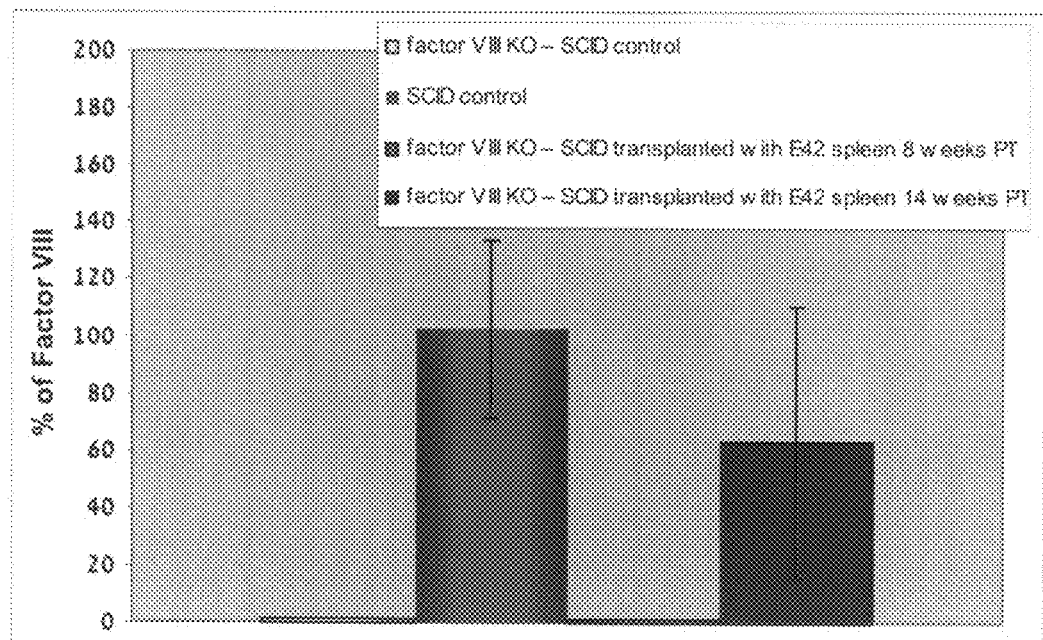
Figure 17B:
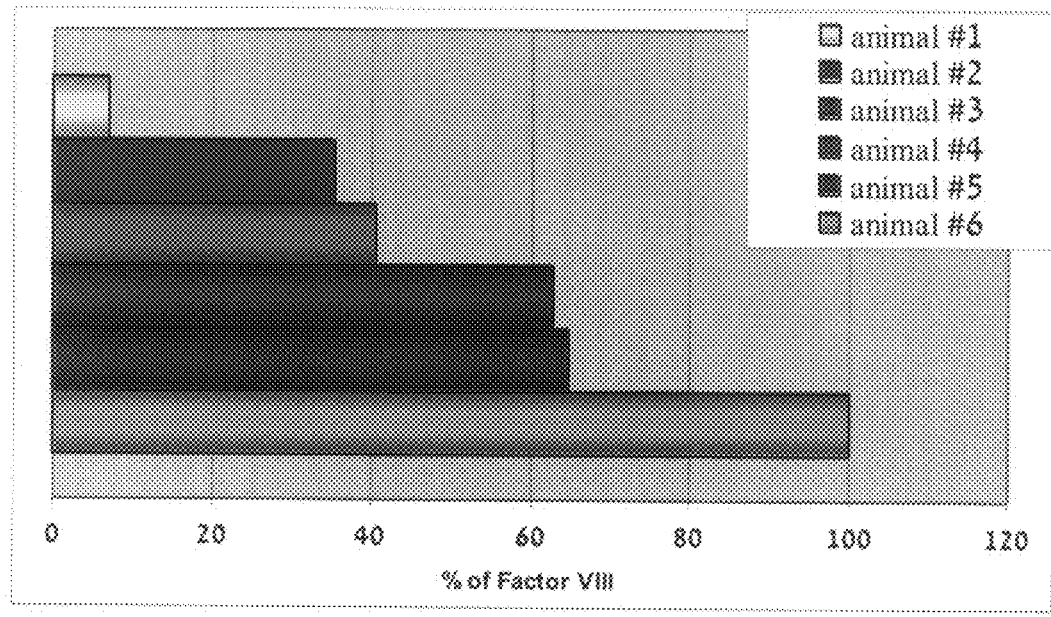

FIGS. 17a-b are bar-graphs depicting chromogenic determination of factor VIII activity in plasma of transplanted mice. FIG. 17a depicts comparison of factor VIII KO-SCID control mice (yellow), wild type NOD-SCID control mice (red) and factor VIII KO-SCID mice transplanted with E42 pig spleen 8 weeks (purple) and 14 weeks (blue) after transplantation. FIG. 17b depicts distribution of factor VIII levels determined by chromogenic assay in individual factor VIII KO-SCID mice, 14 weeks after transplantation of E42 pig spleen precursor tissue.

DESCRIPTION OF THE PREFERRED EMBODIMENTS

The present invention is of methods of providing pancreatic, lymphoid/hematopoietic or pulmonary organ and/or tissue functions to a mammalian subject by transplantation of developing organ/tissue grafts. These methods can respectively be used to effectively treat via therapeutic transplantation human patients suffering from pancreatic diseases such as type I diabetes, hematological/metabolic diseases such as hemophilia and Gaucher disease, or pulmonary failure. The present invention employs transplantation of novel organ/tissue-specific grafts which are at developmental stages at which these grafts have the capacity to generate in graft recipients organs/tissues displaying an optimal combination of structural and functional differentiation, growth, immune acceptance in the case of non-syngeneic grafts, and low risk of teratoma formation.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Organ or tissue transplantation is the optimal or sole therapy for numerous highly debilitating/lethal pancreatic, pulmonary and hematological/metabolic diseases. However, current methods of therapeutic transplantation are severely hampered by inadequate sources of immunologically and/or morphologically compatible donor organs/tissues, and by the permanent requirement for highly intensive and harmful immunosuppressive treatment of graft recipients to prevent graft rejection. Strategies suggested for overcoming these obstacles involve using developing/non-syngeneic organ/tissue grafts, such as developing pig or human grafts—such grafts being potentially available in sufficient quantities, and having been shown to be better tolerated by mismatched recipients than fully differentiated organ/tissue grafts by virtue of being derived from gestational stage donors.

However, all previous approaches involving transplantation of developing/non-syngeneic pancreatic, pulmonary or lymphoid/hematopietic organs/tissues suffer from significant disadvantages, including: suboptimal tolerance by non-syngeneic host lymphocytes; suboptimal structural and functional graft differentiation, for example with respect to insulin production by pancreatic organ/tissue grafts; predominantly graft-derived, as opposed to host-derived, graft vascularization, thereby leading to immune rejection; suboptimal growth; inadequate availability of transplantable organs/tissues; and/or suboptimal safety for human administration, notably with respect to avoidance of generation of graft-derived teratomas.

Previous approaches employing developing non-syngeneic grafts have been uniformly suboptimal since the optimal gestation time for implantation based on risk for teratoma, growth potential and immunogenicity, all of which might vary between different organs in fetal development, was not sufficiently characterized. Moreover, the prior art fails to teach any method of practicing therapeutic transplantation of developing non-syngeneic lymphoid organ/tissue grafts.

While reducing the present invention to practice, the present inventors have uncovered specific developmental stages of non-syngeneic pancreatic, pulmonary and lymphoid/hematopietic organ/tissue grafts during which these can be transplanted into a recipient so as to generate, in the absence of graft-derived teratomas, cells, organs and tissues which display optimal growth, structural and functional differentiation and requirement for minimal recipient immunosuppression.

Specifically, while reducing the present invention to practice, the following were uncovered: pancreatic xenografts derived from pigs at a developmental stage of 42 to 80 days of gestation (e.g., 42-56 days of gestation), or human pancreatic organ/tissue allografts at a developmental stage of 14-20 weeks, can be used to generate following transplantation well-developed insulin-producing pancreatic organs/tissues; pulmonary organ/tissue xenografts from pigs at a gestational stage of 42 to 80 days of gestation can generate following transplantation well developed pulmonary organs/tissues including alveolar structures; and lymphoid/hematopietic organ/tissue xenografts from pigs at a gestational stage of 42 to 80 days can generate well developed lymphoid/hematopietic organs/tissues following transplantation. In particular, lymphoid/hematopietic organ/tissue xenografts from pigs at a gestational stage of 42 days were used to generate well developed lymphoid/hematopietic organs/tissues which secrete therapeutic levels of factor VIII following transplantation into factor VIII-deficient mammals.

As shown hereinbelow and in the Examples section which follows, therapeutic grafts of the present invention are harvested at a specific developmental window which impart these grafts with functionality and endurance characteristics which are superior to the grafts provided by the prior art. Thus, as is shown in the Examples which follow, pancreatic porcine grafts harvested at E42-56 are superior to prior art porcine grafts harvested at E28 (US Patent Publication No. 20040136972) or E80 [Groth C G. et al., (1994) Lancet 344: 1402-4]. Similarly, porcine embryonic spleen harvested at E42 are superio to tissue harvested at E28 and E 80.

The present invention is based on the unexpected discovery of distinct gestational time windows optimal for therapeutic transplantation of developmental stage pancreatic, pulmonary or lymphoid/hematopietic organs/tissues. There are three major criteria for selecting developing/non-syngeneic grafts for therapeutic transplantation: (i) the graft should be at a sufficiently advanced developmental stage so as to be capable of generating a structurally and functionally differentiated, host vascularized organ/tissue in-situ; (ii) the graft should be at a sufficiently advanced developmental stage so as not to induce graft-derived teratomas; and (iii) the graft should be at a sufficiently early developmental stage so as to be optimally tolerated immunologically by non-syngeneic human lymphocytes. Often there is a tradeoff between the three criteria, with functionality of the tissue organ being the most urgent.

Thus, according to one aspect of the present invention, there is provided a method of providing a pancreatic function to a mammalian subject. The method is effected by transplanting into the subject a mammalian pancreatic organ/tissue graft, which is at a developmental stage essentially corresponding to that of a porcine pancreatic organ/tissue at a gestational stage of about 42 to about 80 days of gestation.

As used herein the term "about" refers to plus or minus 10 percent.

The method according to aspects of the present invention relating to transplantation of pancreatic organ/tissue grafts can be used for treating any disease in the subject which is amenable to treatment via transplantation of a pancreatic organ/tissue graft.

As used herein, the term "treating" includes curing, alleviating, or stabilizing the disease, or inhibiting future onset or development of the disease.

As used herein, the term "disease" refers to any disease, disorder, condition or to any pathological or undesired condition, state, or syndrome, or to any physical, morphological or physiological abnormality.

Diseases of the present invention are typically resulting or are associated with abnormal activity of at least one biomolecule naturally produced by the subject. Such an abnormal activity of the biomolecule may result from abnormal synthesis or degradation of the biomolecule. Alternatively, it may result from abnormal catalytic activity (i.e., increased or decreased as compared to an activity produced by a healthy tissue).

The subject according to various aspects of the present invention is preferably a human.

Preferably, the pancreatic organ/tissue graft which is at a developmental stage essentially corresponding to that of a porcine pancreatic organ/tissue at a gestational stage of about 28-80 of gestation, preferably of about 42 to about 56 days of gestation.

While such a graft may originate from any of various donor mammals, as described further hereinbelow, such a graft is preferably non-syngeneic with the subject and/or is derived from a pig, most preferably both of which. Alternately, such a pancreatic organ/tissue graft may be syngeneic with the subject and/or derived from a human.

As used herein, the term "non-syngeneic" graft refers to a graft which is not essentially genetically identical with the subject or essentially all lymphocytes of the subject, such as an allogeneic graft or a xenogeneic graft.

As used herein, the term "allogeneic graft" refers to a graft which is derived from a donor which is non-syngeneic with the subject or with a substantial proportion of the lymphocytes present in the subject, and which is of the same species as the subject or substantially all of the lymphocytes of the subject. Typically, non-clonal/non-twin mammals of the same species are allogeneic relative to each other.

As used herein, the term "xenogeneic graft" refers to a graft which is derived from a donor that is of a different species than the subject or of a substantial proportion of the lymphocytes present in the subject.

As used herein, the term "syngeneic graft" refers to a graft which is essentially is genetically identical with the subject or essentially all lymphocytes of the subject. Examples of syngeneic grafts include a graft derived from the subject (also referred to in the art as an "autologous graft"), from a clone of the subject, or from an identical twin of the subject.

Thus, according to another aspect of the present invention, there is provided a method of providing a pancreatic function to a mammalian subject. The method is effected by transplanting into the subject a pancreatic organ/tissue graft which is at a developmental stage essentially corresponding to that of a human pancreatic organ/tissue at a gestational stage of about 14 to about 20 weeks of gestation.

Preferably, the pancreatic organ/tissue graft which is at a developmental stage essentially corresponding to that of a human pancreatic organ/tissue at a gestational stage of about 14 to about 20 weeks of gestation.

While such a graft may originate from any of various donor mammals, as described further hereinbelow, such a graft is preferably of human fetal origin and/or is non-syngeneic with the subject. Alternately, such a pancreatic organ/tissue graft may be derived from a pig. The graft may be syngeneic with the subject.

Transplantation of a pancreatic organ/tissue graft of the present invention is preferably used to provide pancreatic function to a subject having an abnormal serum concentration of a biomolecule produced by a mammalian pancreas, more preferably where the serum concentration is abnormally low. Preferably the biomolecule is produced by mammalian pancreatic islets, and is most preferably insulin.

As is described and illustrated in Example 6 of the Examples section below, a pig pancreatic organ/tissue xenograft at a developmental stage of 42 to 56 days can be used to generate, in the absence of teratoma formation, well developed pancreatic organs/tissues producing optimal levels of insulin in a recipient thereof, and hence can be used for treatment of a pancreatic disease such as type 1 diabetes (insulin-dependent diabetes mellitus, and juvenile onset diabetes).

It will be appreciated that the present disclosure that a mammalian pancreatic organ/tissue graft which is at such a developmental stage can be used to generate well developed insulin-secreting pancreatic organs/tissues suitable for treatment of a pancreatic disease, such as type 1 diabetes, is clearly novel and unpredictable relative to the prior art.

As is further shown and illustrated in Example 5 of the Examples section below, a pancreatic organ/tissue allograft of human origin at a developmental stage of 8 weeks can be used to generate, in the absence of teratoma formation, well developed pancreatic organs/tissues producing optimal levels of insulin in a recipient thereof, and hence can be used for treatment of a pancreatic disease such as type 1 diabetes.

It will be appreciated that the present disclosure that a mammalian pancreatic organ/tissue graft which is at such a developmental stage can be used to generate well developed insulin-secreting pancreatic organs/tissues suitable for treatment of a pancreatic disease, such as type 1 diabetes, is clearly novel and unpredictable relative to the prior art.

Alternately, examples of diseases which can be treated via aspects of the present invention relating to transplantation of a pancreatic organ/tissue graft include type 2 diabetes and pancreatic cancer.

Thus, according to a further aspect of the present invention, there is provided a method of generating pulmonary tissue in a mammalian subject in need thereof. The method is effected by transplanting into the subject a developing mammalian pulmonary graft which is at a developmental stage essentially corresponding to that of a porcine pulmonary organ/tissue at a gestational stage of about 42 to about 80 days of gestation.

The method according to this aspect of the present invention can be used for treating any disease in the subject which is amenable to treatment via transplantation of a pulmonary organ/tissue graft.

Preferably, the pulmonary graft is at a developmental stage essentially corresponding to that of a porcine pulmonary organ/tissue at a gestational stage of about 56 to about 80 days of gestation.

While such a graft may originate from any of various donor mammals, as described further hereinbelow, such a graft is preferably of porcine origin and/or is non-syngeneic with the subject, most preferably both of which. Alternately, the lymphoid/hematopietic organ/tissue graft may be syngeneic with the subject and/or derived from a human.

As is described and illustrated in Example 7 of the Examples section below, a pulmonary organ/tissue xenograft of porcine origin at a developmental stage of 56 to 80 days can be used to generate, in the absence of teratoma formation, well developed pulmonary organs/tissues which comprise alveolar structures. Hence, such pulmonary organ/tissue grafts can be used for therapeutic transplantation for treatment of pulmonary failure.

It will be appreciated that the present disclosure that a mammalian pulmonary organ/tissue graft which is at such a developmental stage can provide pulmonary organs/tissues to a recipient thereof is clearly novel and unpredictable relative to the prior art.

Examples of pulmonary diseases which can be treated according to this aspect of the present invention include cystic fibrosis, emphysema, asbestosis, chronic obstructive pulmonary disease (COPD) and pulmonary fibrosis.

Thus, according to a still further aspect of the present invention, there is provided a method of providing a lymphoid/hematopietic organ/tissue function to a mammalian subject.

The method is effected by transplanting into the subject a developing mammalian lymphoid/hematopietic organ/tissue graft.

The method according to this aspect of the present invention can be used for treating any disease in the subject which is amenable to treatment via transplantation of a lymphoid/hematopietic organ/tissue graft. In particular, the method according to this aspect of the present invention can be used to treat hemophilia, in particular hemophilia A.

Preferably, the lymphoid/hematopietic organ/tissue graft is at a developmental stage at which a lymphoid/hematopietic organ/tissue essentially does not comprise T-cells.

Without being bound to a paradigm, the present inventors are of the opinion that a lymphoid/hematopietic organ/tissue graft at such a developmental stage will have minimal risk of inducing graft-versus-host disease (GVHD) in a recipient thereof by virtue of lacking T-cells.

Preferably, the lymphoid/hematopietic organ/tissue graft is at a developmental stage essentially corresponding to that of a porcine lymphoid/hematopietic organ/tissue at a gestational stage of about 42 to about 80 days of gestation, more preferably at a developmental stage essentially corresponding to that of a porcine lymphoid/hematopietic organ/tissue at a gestational stage of about 42 to about 56 days of gestation, and most preferably, at a developmental stage essentially corresponding to that of a porcine lymphoid/hematopietic organ/tissue at a gestational stage of about 42 days of gestation.

The lymphoid/hematopietic organ/tissue graft is capable of producing lymphocytes and/or hematopoietic cells. The lymphoid/hematopietic organ/tissue preferably derived from spleen. Alternately, the lymphoid/hematopietic organ/tissue graft may be derived from lymph node, Peyer's patches thymus or bone marrow.

While such a graft may originate from any of various donor mammals, as described further hereinbelow, such a graft is preferably of porcine origin and/or is non-syngeneic with the subject, most preferably both of which. Alternately, the lymphoid/hematopietic organ/tissue graft may be syngeneic with the subject and/or derived from a human.

Transplantation of a lymphoid/hematopietic organ/tissue graft of the present invention is preferably used to provide lymphoid/hematopietic organ/tissue function to a subject having an abnormal activity of a biomolecule naturally produced by a mammalian lymphoid/hematopietic organ/tissue.

Preferably, the biomolecule is a clotting cascade factor, more preferably factor VIII.

As is shown and illustrated in Example 10 of the Examples section below, a lymphoid/hematopietic organ/tissue xenograft of porcine origin at a developmental stage of 42 days of gestation can be used to generate, in the absence of teratoma formation, well developed lymphoid/hematopoietic organs/tissues producing therapeutic levels of a hematological enzyme, such as factor VIII, where the subject has a disease involving a deficiency of such an enzyme, and hence can be used for treatment of a subject having a hematological/metabolic disease such as a hemophilia, in particular hemophilia A.

It will be appreciated that the present disclosure that a mammalian lymphoid/hematopietic organ/tissue graft which is at such a developmental stage can be used to generate lymphoid/hematopietic organs/tissues capable of generating therapeutic levels of factor VIII in a factor VIII-deficient mammal is clearly novel and unpredictable relative to the prior art.

Other examples of diseases associated with clotting factor deficiency which can be treated according to this aspect of the present invention include hemophilia B/factor IX deficiency and von Willebrand's disease/von Willebrand factor deficiency. The method according to this aspect of the present invention can be used to treat any of various hematological lysosomal storage diseases, including Gaucher disease (glucocerebrosidase deficiency). It will be appreciated that the method according to this aspect of the present invention can also be used to repair splenic injury.

Depending on the transplantation context, in order to facilitate engraftment of a non-syngeneic graft of the present invention transplanting a graft of the present invention may further advantageously comprise treating a subject of the present invention with an immunosuppressive regimen prior to, concomitantly with, or following transplantation of the graft. In general it will be appreciated that engraftment of later stage grafts will require greater immunosuppression of a graft recipients than for earlier stage grafts. The disadvantages of immunosuppressive therapy may be clearly outweighed by the benefits of a fully functioning organ/tissue, as in the case of a life-saving transplantation.

Preferably, in order to facilitate engraftment of a non-syngeneic graft, the immunosuppressive regimen may advantageously comprise transiently administering to the subject at least one T-cell costimulation inhibitor and at least one CD40 ligand inhibitor, and more preferably may further comprise administering to the subject an inhibitor of T-cell proliferation.

Preferably, the T-cell costimulation inhibitor is CTLA4-Ig, the CD40 ligand inhibitor is anti-CD40 ligand antibody, and the inhibitor of T-cell proliferation is rapamycin. Alternately, the T-cell costimulation inhibitor may be an anti-CD40 antibody. Alternately, the T-cell costimulation inhibitor may be an antibody specific for B7-1, B7-2 or CD28. Such polypeptide drugs are particularly advantageous since these are, unlike commonly used immunosuppressant drugs like cyclosporin A, essentially non-toxic and/or non-carcinogenic, and by virtue of passively blocking cell surface receptor interactions, afford reversible and temporary immunosuppression of the subject.

A suitable immunosuppressive regimen for overcoming rejection of porcine xenografts, as described in Example 6 (FIG. 8c), is as follows: rapamycin administered subcutaneously at 1.5 milligrams per kilogram on a daily basis from day 0+8 milligrams per kilogram CTLA4-Ig, and 10 milligrams anti-CD40 ligand antibody per kilogram administered intraperitoneally on days 0, 2, 4, 6 after transplantation.

Examples of suitable types of immunosuppressive regimens include administration of immunosuppressive drugs, tolerance inducing cell populations, and/or immunosuppressive irradiation.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J. Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Examples of suitable immunosuppressive drugs include, but are not limited to, CTLA4-Ig, anti CD40 antibodies, anti CD40 ligand antibodies, anti B7 antibodies, anti CD3 antibodies (for example, anti human CD3 antibody OKT3), methotrexate (MTX), Copaxone, rapamycin, prednisone, methyl prednisolone, azathioprene, cyclosporin A (CsA), tacrolimus, cyclophosphamide and fludarabin, mycophenolate mofetil, daclizumab [a humanized (IgG1 Fc) anti-IL2R alpha chain (CD25) antibody], and anti T cell antibodies conjugated to toxins (for example, cholera A chain, or *Pseudomonas* toxin).

A graft according to the present invention can be transplanted into the subject in any of various ways, depending on the application and purpose, so as to provide an organ/tissue-specific function to the subject according to the teachings of the present invention. One of ordinary skill in the art, such as a transplant surgeon specialized in the disease to be treated, will possess the necessary expertise so as to apply the teachings of the present invention for transplanting a therapeutically effective graft of the present invention to a subject of the present invention. It will be appreciated that that in order to treat the disease, transplanting the graft should be effected in such a way as to therapeutically replace or repair the organ or tissue displaying pathological physiology or morphology associated with the disease.

As used herein, the term "therapeutically effective graft" refers to a graft having structural and/or functional characteristics such that transplantation thereof into the subject serves to treat the disease.

Transplanting a graft of the present invention may be effected in numerous ways, depending on various parameters, such as, for example, the type, stage or severity of the disease to be treated, the physical or physiological parameters specific to the individual subject, and/or the desired therapeutic outcome. For example, depending on the application and purpose, transplanting the graft may be effected by implanting the graft into any one of various suitable anatomical locations of the subject, using a graft consisting of a whole or partial organ or tissue, and/or by using a graft consisting of various numbers of discrete organs, tissues, and/or portions thereof.

A graft of the present invention may be derived from a donor which is of any one of various species. Suitable species origins for the graft comprise the major domesticated or livestock animals, and primates, which have been extensively characterized with respect to correlation of stage of differentiation with gestational stage may be suitable for practicing the method. Such animals include bovines (e.g., cow), equines (e.g., horse), ovines (e.g., goat, sheep), felines (e.g., *Felis domestica*), canines (e.g., *Canis domestica*), rodents (e.g., mouse, rat, rabbit, guinea pig, gerbil, hamster), and primates (e.g., chimpanzee, rhesus monkey, macaque monkey, marmoset).

Various methods may be employed to obtain a graft at a developmental stage essentially corresponding to that of a porcine or human derived graft, as presently taught. Obtaining such a graft is optimally effected by harvesting the graft from a developing graft donor embryo or fetus at such a stage of gestation. It will be understood by those of skill in the art that the gestational stage of an organism is the time period elapsed following fertilization of the oocyte generating the organism.

A graft at a desired developmental stage may be obtained by in-vitro culture of cells, organs/tissues. Such controlled in-vitro differentiation of cells, tissues or organs is routinely performed, for example, using culturing of embryonic stem cell lines to generate cultures containing cells/tissues/organs of desired lineages. For example, for generation of various lineages, including endodermal lineages such as liver; ectodermal lineages such as brain, skin and adrenal; and mesodermal lineages such as muscle, cartilage, mullerian duct, and heart, refer, for example, to: Schuldiner M. et al., 2000. Proc Natl Acad Sci USA. 97:11307-11312 and Itskovitz-Eldor J. et al., 2000. Mol Med 6:88; for pancreatic differentiation of embryonic stem cells, refer, for example, to: Lee S. H., et al., 2000. Nature Biotechnol. 18:675; Lumelsky et al., 2001. Science 292:1389-1394; Soria et al., 2000. Diabetes 49:1-6; Schuldiner M. et al., 2000. Proc Natl Acad Sci USA. 97:11307-11312). For differentiation of pulmonary lineages, refer for example, to Otto W R., 1997. Int J Exp Pathol. 78:291-310.

The following table provides examples of the gestational stages of human and porcine grafts at which these can provide grafts which are essentially at corresponding developmental stages:

| Corresponding gestational stages of pigs and humans. | |
|---|---|
| Gestational stage of porcine graft (days) | Gestational stage of human graft (days) |
| 18 | 44 |
| 20 | 49 |
| 22 | 54 |
| 23 | 56-57 |
| 25 | 61-62 |
| 26 | 63 |
| 28 | 68-69 |
| 31 | 75 |
| 38 | 92 |
| 42 | 102 |
| 46 | 112 |
| 49 | 119 |
| 56 | 136 |
| 62 | 151 |
| 72 | 175 |
| 80 | 195 |
| 88 | 214 |

The gestational stage (in days) of a graft belonging to a given species which is at a developmental stage essentially corresponding to that of a porcine graft can be calculated according to the following formula: [gestational stage of porcine graft in days]/[gestational period of pig in days] × [gestational stage of graft of given species in days]. Similarly, the gestational stage (in days) of a graft belonging to a given species which is at a developmental stage essentially corresponding to that of a human graft can be calculated according to the following formula: [gestational stage of human graft in days]/[gestational period of humans in days] × [gestational stage of graft of given species in days]. The gestational stage of pigs is about 115 days and that of humans is about 280 days.

As described hereinabove, transplanting the graft may be effected by transplantation thereof into various suitable anatomical location so as to be of therapeutic effect.

Depending on the application and purpose, the graft may be transplanted into a homotopic anatomical location (a normal anatomical location for the organ or tissue type of the graft), or into an ectopic anatomical location (an abnormal anatomical location for the organ or tissue type of the graft). Optionally, when transplanting the graft to repair or replace a damaged organ/tissue, the latter may be removed, for example, so as to enable growth and engraftment of the graft, for example in the context of organ replacement by transplantation of the graft into a homotopic anatomical location.

Depending on the application and purpose, the graft may be advantageously implanted under the renal capsule, or into the kidney, the testicular fat, the sub cutis, the omentum, the portal vein, the liver, the spleen, the heart cavity, the heart, the chest cavity, the lung, the pancreas and/or the intra abdominal space.

Transplanting a pancreatic organ/tissue graft of the present invention may be advantageously effected by transplanting the graft into the portal vein, the liver, the pancreas, the testicular fat, the sub-cutis, the omentum, an intestinal loop (the subserosa of a U loop of the small intestine) and/or the intra-abdominal space. Preferably, transplanting a pancreatic organ/tissue graft of the present invention is effected by transplanting the graft under at least one renal capsule of the subject. Preferably, for transplanting a pancreatic organ/tissue graft into the portal vein, the pancreatic organ/tissue graft is a pancreatic islet graft. For the omentum site, omentum will be recognized and omental pocket will be created by circular suture legation followed by embryonic tissue implantation into the pocket. Guidance for practicing therapeutic transplantation of pancreatic organ/tissue grafts according to the teachings of the present invention is provided in the Examples section below.

As is described and illustrated in the Examples section below, a pancreatic or lymphoid/hematopoietic organ/tissue graft can be transplanted into under a renal capsule of a mammal so as to produce significant levels of insulin or of a hematological factor such as factor VIII, respectively, in the serum of the subject.

As is further described and illustrated in the Examples section below, a pulmonary organ/tissue graft can be transplanted into under a renal capsule of a mammal so as to generate well developed pulmonary organs/tissues which comprise alveolar structures in the subject. Such pulmonary organs/tissues can be suitably re-implanted in the thorax of the subject after such development in such a way as to provide pulmonary function to the subject.

Depending on the application and purpose, transplanting the graft may be effected by transplanting a graft consisting of a whole or partial organ, and/or may be effected by transplanting a graft consisting of various numbers of discrete organs, tissues, and/or portions thereof.

For example, transplanting increasing numbers of discrete organ or tissue grafts may be advantageously employed to increase the physiological or physical therapeutic effect of the graft to desired levels. For example, where the graft is a graft of pancreatic islets, increasing the number of grafts can be used to generate sufficiently high serum levels of a pancreatic hormone, such as insulin, so as to treat a pancreatic hormone deficiency such as type 1 diabetes. Similarly, increasing the number and/or the mass of lymphoid/hematopoietic organ/tissue grafts can be used to generate sufficiently high levels of a hematopoietic factor, such as factor VIII or glucocerebrosidase, so as to enable treatment of hemophilia A or Gaucher disease, respectively.

Following transplantation, the immunological tolerance of the subject, in the case of a non-syngeneic graft, and the functional and structural growth and differentiation of the graft may be advantageously monitored.

Evaluation of serum levels in the subject of essentially any biomolecule produced by a pancreatic or lymphoid/hematopoietic organ/tissue graft, such as insulin, factor VIII, glucocerebrosidase and the like, whose deficiency is known to be associated with a disease, can easily be monitored according to standard medical diagnostic methods, including as described in the Examples section which follows. Normalization of serum glucose levels in the serum of a diabetic subject following transplantation of a pancreatic islet graft is indicative of graft functionality (i.e., physiologically regulated insulin secretion by the graft). In general histological graft development can be monitored via biopsy, and gross morphological/structural graft development can be monitored via any of various standard medical imaging and diagnostic methods.

Various methods may be employed to assess the subject's immunological tolerance to the graft. For example the tolerance may be assessed by monitoring subject-specific leukocyte or T cell specific infiltration of the graft, by monitoring the origin of the graft vasculature, and/or by monitoring the histological appearance of organ or tissue specific structures. Such monitoring may be advantageously effected using methods, such as via sample biopsy, known to those with skill in the art. Infiltration of subject leukocytes, neutrophils, natural killer cells, or T cells into the graft, or lack thereof, are typically indicative of suboptimal or optimal engraftment of a non-syngeneic graft in the subject, respectively. In cases where subject tolerance of the graft requires improvement, therapeutic adjunct immunosuppressive treatment of the subject may be advantageously performed or adjusted, as described hereinabove. It will be appreciated by the artisan that an optimally tolerated graft is a graft not rejected or not substantially infiltrated in the subject by T lymphocytes non-syngeneic with the graft. A graft may be rejected via hyperacute rejection, acute rejection, or chronic rejection. Ample guidance for ascertaining graft rejection is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J. Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al., 1998. Lancet 351, 623). Graft-derived vascularization will generally correlate with poor engraftment, and will tend to increase with the gestational stage of the graft at time of implantation.

It will be appreciated that the present invention enables identification of appropriate developmental stages of organ/tissue grafts of any of various lineages which can be used for treatment of essentially any disease associated with pathological organ or tissue physiology or morphology which is amenable to treatment via transplantation. Such diseases include renal, splenic, pancreatic, cardiac, hepatic, hematological, genetic, pulmonary, brain, gastrointestinal, muscular, endocrine, osseous, neural, hematological/metabolic, dermal, cosmetic, opthalmological, and vascular diseases.

Thus, the present invention identifies developmental stages of pancreatic, pulmonary and lymphoid/hematopoietic organ/tissue grafts, such as porcine grafts which can be obtained in essentially unlimited quantities, at which such grafts can be used to optimally treat diseases in humans, such as type 1 diabetes and hemophilia A, which are amenable to treatment via transplantation, respectively, of pancreatic, pulmonary or lymphoid/hematopoietic organs/tissues.

It is expected that during the life of this patent many relevant medical diagnostic techniques will be developed and the scope of the phrase "method of evaluating the stage of differentiation of a mammalian organ most suitable for transplantation thereof into a mammalian subject" is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Miscellaneous Materials and Methods

Transplantation of Fetal Tissue Under the Renal Capsule:
Transplantation of a graft under the renal capsule may be desired for grafts other than renal grafts. Transplantation of fetal tissue under the renal capsule of recipient mice was performed as previously described (Dekel, B. et al., 1997. Transplantation 64, 1541-1550). Whole fetal human or porcine organs or whole or 1-2 millimeter-diameter fragments of tissues at later stages of gestation were used in transplantations. For growth assays, transplantation was performed 7-10 days following reconstitution of irradiated hosts with NOD/SCID bone marrow. Alternatively, fetal tissues were transplanted into SCID recipient mice. For transplantation, fetal tissues were maintained in sterile conditions at 4 degrees centigrade for approximately two hours in either RPMI 1640 or Dulbecco's modified Eagle's medium supplemented with 10 percent fetal calf serum (FCS; Biological Industries, Beit Haemek, Israel). Transplantation of tissues was performed under general anesthesia induced by intraperitoneal injection of 2.5 percent Avertin in phosphate buffer saline solution (10 milliliters per kilogram body weight). Both host kidneys were exposed via a bilateral incision, a 1.5 millimeter incision was made at the caudal end of the renal capsule, and an approximately one cubic millimeter fragment of renal tissue was implanted under each renal capsule. Tissues were also transplanted intra-abdominally to control for renal sub-capsular space specific immune privilege. Transplanted mice were treated post-operatively with ciprofloxacin in their drinking water for 7 days.

Analysis of Graft Vascularization:
Five micrometer thick paraffin sections were immunostained with antibodies specific for blood vessels, including PECAM-1 and CD-31, according to the manufacturer's instructions. Blood vessel counts were performed in similar regions within the grafts per high-power field (5 consecutive fields per transplant in 5 transplants per group).

Example 2

Transplantation of 12-16 Week Fetal Human and Animal Pancreatic Organ/Tissue Grafts into a Host Fetal human or porcine organs/tissues transplanted into a host are capable of generating structurally and functionally differentiated, host-integrated organs/tissues optimally tolerated by alloreactive/xenoreactive human lymphocytes. Thus, while conceiving the present invention, it was hypothesized that transplanting fetal human or animal pancreatic organs/tissues harvested at a defined time window into a host will generate pancreatic organs/tissues displaying significant development, as follows.

Materials and Methods:
Donor Pancreatic Tissues:
Human 12- to 16-week gestational stage pancreatic tissues were obtained following curettage, with warm ischemia time of less than 30 minutes. Following dissection, the pancreatic tissues were kept at 4 degrees centigrade in UW solution for less than 45 minutes in sterile conditions. The study protocol was approved by the hospital (Kaplan Medical Center, Rehovot, Israel) Helsinki committee.

Animal pancreatic tissues at 12- to 14-day gestational stage were microdissected from mouse embryos under the light microscope. Tissues were kept at 4 degrees centigrade in RPMI 1640 medium solution prior to transplantation.

Transplantation Procedure:
Transplantation of human and animal pancreatic organs/tissues at early stages of gestational development was performed as described in Example 1 of the Examples section above with modifications. For transplantation under the renal capsule, host kidney is exposed through a left lateral incision, a 1.5 millimeter incision is made at the caudal end of the renal capsule, and donor pancreatic tissues are grafted under the renal capsule in [1-2]×[1-2] millimeter fragments.

Experimental Results:
Four 12- to 16-week gestational stage human pancreatic organ/tissue-derived grafts were transplanted under the renal capsule in 4 SCID and 4 normal mice. Each fragment size at transplantation was 1-2 millimeters in diameter. In all immunocompetent mice rejection was detected beginning at 5 days posttransplantation as determined via histological analysis indicating graft necrosis and tissue destruction. In all immunodeficient mice, graft acceptance was observed, as determined by growth of the graft and the absence of signs of rejection upon histological and macroscopic examination. In a 12-week gestational stage human pancreatic tissue-derived graft harvested at 8 weeks posttransplantation, graft size had increased 10-fold (2×2 millimeters pre-transplantation to 8×5 millimeters at harvesting).

Mouse 14-, 13-, and 12-day gestational stage pancreatic organs/tissues were transplanted under the renal capsule in immunodeficient syngeneic (Balb/c) mice. In a 12-day gestational stage tissue-derived graft harvested 2 weeks posttransplantation, graft size had increased 10 fold (1×1 millimeter pretransplantation to 5×3 millimeters posttransplantation).

Conclusion:

Later gestational stage human or animal pancreatic organs/tissues transplanted into hosts generate pancreatic organs/tissues displaying significant development. These results thus anticipate the use of 14-20 week gestational stage human pancreatic grafts for treating diseases which may benefit from transplantation of such (e.g., diabetes).

Example 3

Generation of Diabetic Mice

Materials and Methods:

Diabetes is induced in mouse hosts by streptozotocin treatment, as previously described (Soria et al., 2000. Diabetes 49, 1-6) or by alloxan (reviewed in T. Szkudelski, 2001, Physiol. Res. 50: 536-546).

Briefly, diabetes is induced in mouse hosts via a single intraperitoneal injection of 200 milligram streptozotocin (Sigma) freshly dissolved in citrate buffer (pH 4.5) per kilogram body weight. Onset of diabetes is then confirmed and monitored by the presence of weight loss, polyuria, and blood glucose levels of less than 500 milligrams/dl. Blood for glucose tests is obtained by tail snipping and measured between 9 and 11 A.M. under non-fasting conditions and analyzed with a portable glucose meter. Two weeks following injection of streptozotocin, diabetic recipients are engrafted with donor pancreatic tissues, and glucose levels are monitored as described above in order to ascertain restoration of glycemic control.

Alloxan Protocol:

To determine the capacity of the graft to regulate hyperglycemia of the mouse, grafted and non-grafted (E42 embryonic pancreas 4 months after transplant) NOD-SCID mice were injected intravenously with Alloxan (Sigma-Aldrich 90 milligrams per kilogram), which is known to destroy rodent, but not human or porcine beta cells (Eizirik D, et al. 1994, Proc Natl Acad Sci USA 91: 9253). Alloxan was prepared by dissolving 30 milligrams alloxan-monohydrate 90 percent in 1 milliliter of 1 millimolar HCL solution of NaCl 0.9 percent. The dose for IV injection is 90 milligrams per kilogram. Glucose concentrations were measured by tail tipping before alloxan treatment, 4 days and 10 days after alloxan administration and then once weekly.

Example 4

Treatment of Diabetes by Transplantation of Early Gestational Stage Human or Porcine Pancreatic Tissue into Diabetic Human Recipients without or with Minimal Immunosuppression of Recipients Diabetes is a disease of tremendous medical and economic impact, however treatment of this disease by daily injection of insulin, the standard therapy, does not satisfactorily prevent or alleviate its debilitating or lethal consequences. An attempt to overcome this limitation has been treatment of diabetes by transplantation of adult cadaveric donor pancreatic islets. However, this strategy cannot be routinely practiced due to the insufficient numbers of immunologically matching allogeneic donor pancreases from which to isolate the sufficient numbers of islets required.

As taught in U.S. 20030096016, 7- to 8-week gestational stage human renal organ/tissue-derived grafts, or 20- to 28-day gestational stage porcine organ/tissue-derived grafts transplanted into hosts generate structurally and functionally differentiated, renal organs/tissues of graft type optimally tolerated by alloreactive/xenoreactive human lymphocytes.

Examples 5 and 6 herein are incorporated as comparative examples. The success of those studies was judged on the basis of morphological, histological and immunochemical data. The present invention now shows for the first time functional data that supports transplantation of fetal pancreatic, splenic and pulmonary tissue at a later gestational stage than that previously described.

Example 5

Transplantation of 8 Week Human Pancreatic Organ/Tissue Grafts

Transplantation of 8-week gestational stage human, or 27- to 28-day gestational stage porcine, pancreatic organ/tissue grafts generates, in the absence of graft-derived teratomas, insulin-producing pancreatic organs/tissues which will be optimally tolerated by alloreactive/xenoreactive human lymphocytes. This example is provided as a comparative example.

Allogeneic donor pancreatic organ/tissue transplantation remains the optimal therapeutic option in case of pancreatic failure. However, therapeutic transplantation of pancreatic organ/tissue grafts derived from an allogeneic donor is often impossible to implement due to haplotype-matching barriers. Moreover, even when a matched donor is found, in order to prevent graft rejection such transplantation requires permanent graft recipient immunosuppression, usually via administration of toxic immunosuppressant drugs such as cyclosporin A. Such immunosuppressive treatments contribute to the drawbacks of allogeneic transplantation, since these are often unsuccessful at preventing graft rejection in the short term, and are usually incapable of indefinitely preventing graft rejection. An alternative to allograft transplantation involves transplantation of xenografts, in particular porcine grafts, which are considered the optimal animal alternative to human grafts. However, xenografts generally cannot be used for transplantation due to highly suboptimal tolerance of such grafts by human lymphocytes. Thus, pancreatic organs/tissues suitable for therapeutic transplantation in humans and tolerated by non-syngeneic human lymphocytes, and adequate sources of such organs/tissues, are highly desired.

One potent strategy for providing pancreatic organs/tissues for transplantation involves using fetal grafts of such organs/tissues, since it has been demonstrated that the earlier the developmental stage of an organ/tissue, the better it is tolerated when transplanted into a non-syngeneic host. However, to date, generation of pancreatic organ/tissue graft-derived tissues/organs displaying satisfactory growth and differentiation in the absence of graft-derived teratomas, and satisfactory immunological tolerance by alloreactive/xenoreactive human lymphocytes, without or with minimal immunosuppression, has not been achieved.

It was hypothesized that there exists a fetal developmental stage during which pancreatic organs/tissues are sufficiently differentiated to be committed to pancreas specific development in the absence of graft-derived teratomas while being sufficiently undifferentiated so as to be optimally tolerated when transplanted into a non-syngeneic host. While reducing the present invention to practice, the existence of specific gestational stages during which human or porcine pancreatic organs/tissues can be transplanted into a host so as to generate, in the absence of graft-derived teratomas, structurally and functionally differentiated insulin-producing organs/tissues which will be optimally tolerated by alloreactive/xenoreactive human lymphocytes were unexpectedly uncovered, as described below.

Materials and Methods:

Harvesting of Human Gestational Stage Pancreatic Organs/Tissues:

Human gestational stage pancreatic organs/tissues for transplantation were obtained by extraction of organ/tissue fragments following voluntary abortions performed mechanically by aspiration at a gestational stage of 8 weeks, after obtaining informed consent. The warm ischemia time of the harvested samples was kept at less than 30 minutes, and following dissection, the organ precursors were kept at 40 degrees centigrade in UW solution or PBS for less than 45 minutes under sterile conditions. The study protocol was approved by the hospital (Kaplan Medical Center, Rehovot, Israel) Helsinki committee.

Harvesting of Porcine Gestational Stage Pancreatic Organs/Tissues:

Porcine gestational stage pancreatic organs/tissues for transplantation were obtained with the assistance of the Lahav Institute for animal research, Kibbutz Lahav. Developing tissues were harvested at a gestational stage of 27-28 days from pregnant sows operated on under general anesthesia. The study protocol was approved by the local institute's Ethics Committee. Tissues for transplantation were extracted under a light microscope and were kept in sterile conditions at 40 degrees centigrade for about two hours in RPMI 1640 (Biological Industries, Bet HaEmek, Israel) prior to transplantation.

Transplantation Procedure:

Transplantations were performed in Balb/cxNOD/SCID chimeras or NOD/SCID mice under general anesthesia induced by intraperitoneal injection of 2.5 percent Avertin in PBS (10 milliliters per kilogram). For transplantation under the renal capsule, the host kidney was exposed through a left lateral incision. A 1.5-mm incision was made at the caudal end of the renal capsule, and 1-2 millimeter-diameter fragments of gestational stage pancreatic tissue were implanted under the renal capsule.

Histological Analysis:

Anti cytokeratin antibody clone MNF 116 (non-cross-reactive with mouse tissues) was used for immunostaining porcine epithelium; and anti insulin antibody and anti human vimentin antibody clone V9 (non-cross-reactive with mouse tissues; used for staining human mesenchymal cells) were obtained from DAKO. Tissues were fixed by overnight incubation in 4 percent paraformaldehyde in PBS, the fixed tissues were processed through graded alcohols, through xylenes, and paraffin-embedded. Four micron-thick sections of embedded tissues were cut and mounted on positively charged glass slides. The slide-mounted tissue sections were deparaffinized in xylenes following rehydration in graded alcohols. Endogenous peroxidase was quenched in 0.6 percent hydrogen peroxide in 70 percent methanol for 20 minutes. Antigen retrieval by microwave boiling or protease pretreatment was applied when needed. For immunostaining, slides were incubated in a humidified chamber for 60 minutes with primary antibody, following application of DAKO Envision TM+ system, horseradish peroxidase (HRP). Diaminobenzidine (DAB) or aminoethylcarbasole (AEC) reagents were used as chromogens. The slides were hematoxylin counterstained and mounted.

Experimental Results:

Transplantation of Porcine 27- to 28-Day Gestational Stage Pancreatic Xenografts Engraft and Display Functional and Structural Pancreatic Differentiation:

Grafts derived from 27- to 28-day gestational stage porcine pancreas transplanted under the renal capsule of NOD/SCID mice clearly displayed pancreas specific structural and functional differentiation, 6 weeks posttransplantation. Grafts derived from 28-day gestational stage porcine liver transplanted into spleens of such mice which were examined 5 weeks posttransplantation displayed significant pancreatic growth. Pancreatic structural differentiation was clearly evident 6 weeks posttransplantation by a graft derived from 27-day gestational stage porcine pancreatic tissue as determined via H&E-stained graft tissue sections which showed differentiation of pancreatic lobular structures with ductal and acinar pancreatic structures. Pancreatic functional differentiation was also evident at 6 weeks posttransplantation in tissue sections of a graft derived from 27-day gestational stage tissue in the form of insulin and pancreatic peptide synthesis Immunostaining of a graft derived from 28-day gestational stage porcine pancreatic tissue with anti cytokeratin antibody clearly showed differentiation of graft derived pancreatic ductal epithelia.

Human 8-Week Gestational Stage Pancreatic Allografts Engraft and Display Functional and Structural Pancreatic Differentiation:

Grafts derived from 8-week gestational stage human pancreatic tissue transplanted under the renal capsule of NOD/SCID mice bearing alloreactive human lymphocytes clearly displayed pancreas specific structural and functional differentiation, 6 weeks posttransplantation. Pancreatic functionality of the graft was convincingly demonstrated by differentiation of insulin-positive beta-cells within pancreatic islets. Furthermore, grafts derived from 8-week gestational stage human pancreatic tissue transplanted under the renal capsule of Balb/cxNOD/SCID chimeras bearing alloreactive human PBMCs also clearly displayed pancreas specific structural and functional differentiation, as shown via differentiation of vimentin positive human mesenchymal cells.

Conclusion:

The above-described results demonstrate that 8-week gestational stage human, or 27- to 28-day gestational stage porcine, pancreatic tissue-derived grafts are capable of generating, in the absence of graft-derived teratomas, structurally and functionally differentiated insulin-producing pancreatic organs/tissues which will be optimally tolerated by alloreactive/xenoreactive human lymphocytes. However, as is evident from the above-results, fetal pancreatic organ/tissue graft harvested from a porcine donor at a later stage, i.e. over E35, and preferably about E42 to about E56, provide superior grafts which are features by functional and enduring characteristics as compared to grafts harvested at E28.

Example 6

Identification of Gestational Stages of functional Porcine Pancreatic Organ/Tissue Grafts Capable of Significant Organ-Specific Development with No/Minimal Risk of Teratoma Formation There is an urgent need for sources of grafts suitable for therapeutic transplantation for treatment of diseases involving failure of organs/tissues such as liver, heart, pancreas or lung. Optimally, such grafts should have the capacity to display adequate development into such organ/tissue types while having minimal potential for immunogenicity resulting in graft rejection following transplantation into a host. Furthermore, the grafted tissue should perform the functions necessary for the particular tissue. One approach which has been advocated for more than two decades involves the use of porcine fetal grafts at gestational stages sufficiently advanced so as to enable suitable/optimal organ-specific development, and sufficiently early so as to avoid/minimize risk of teratoma formation, such as described above and in the literature (Dekel B. et al., 2003. Nat Med 9:53-60) with respect to porcine gestational stage renal grafts. It will be appreciated, however, that different organ/tissue types differentiate overall at different gestational stages, that organs/tissues at increasing gestational stages will generally have decreasing capacity to induce teratoma formation by virtue of generally comprising decreasing numbers of pluripotential cells. It will be further appreciated that specific organ/tissue types may be composed of distinct combinations of tissue sub-types, for example including stromal tissues, which may be at different stages of differentiation with respect to each other within the same organ/tissue type. Therefore, it will be appreciated that gestational stages during which different organ/tissue types are sufficiently advanced so as to have the capacity to display suitable/optimal organ-specific development, and gestational stages during which such organ/tissue types are sufficiently differentiated so as to avoid/minimize risk of teratoma formation and exhibit reduced immunoreactivity will independently and unpredictably vary between different organ/tissue types. Thus, a primary and major drawback to prior art approaches is that these cannot predict whether there even exists, for fetal organs/tissues gestational stages which are sufficiently advanced for grafts thereof to have the capacity to display adequate/optimal organ-specific development with no or minimal risk of teratoma formation following transplantation thereof into a host. Moreover, even if such gestational stages of such organs/tissues do in fact exist, a further drawback of the prior art is that it is unknown what the timing of such gestational stages might be.

While reducing the present invention to practice, as described below, the present inventors have performed trial and error experiments which for the first time unexpectedly prove that there indeed exist, and for the first time provide data serving to define, the timing of gestational stages during which pancreatic, splenic and pulmonary organ/tissue grafts specifically have the capacity to differentiate into adequately/optimally developed organs/tissues of such types with no/minimal risk of teratoma formation following transplantation, while eliciting minimal host immune response. As such, the experimental data provided below enables therapeutic transplantation methods, which overwhelmingly overcome the critical limitations of the art.

Materials and Methods:

Animals:

Animals were maintained under conditions approved by the Institutional Animal Care and Use Committee at the Weizmann Institute. Immune deficient NOD/SCID mice at the age of 8-10 weeks (Weizmann Institute Animal Breeding Center, Rehovot, Israel) were used as hosts for the transplantation studies. All mice were kept in small cages (up to 5 animals in each cage) and fed sterile food and acid water containing ciprofloxacin (20 milligrams per milliliter).

Porcine Fetal Tissues:

Porcine pancreas, spleen and lung precursors, were obtained from the Lahav Institute. Pregnant sows were operated at precise stages of the pregnancy (E 21, E24, E28, E42, E56, E80 and E100) under general anesthesia. The sows were fertilized by artificial insemination. Time of gestation is defined as the time elapsed from fertilization. The day of insemination is designated as E0. E1 begins at the end of E0. The study protocol was approved by both ethic committees at Kibbutz Lahav and the Weizmann Institute. Warm ischemia time was less than 10 minutes and the embryos were transferred in cold PBS. Tissues for transplantation were extracted under the stereoscope and were maintained under sterile conditions at 40 degrees centigrade in RPMI 1640 (Biological Industries, Beit HaEmek, Israel) prior to transplantation. Cold ischemia time prior to transplantation was approximately 2 hours.

Kidney Sub-Capsular Transplantation:

Transplantation of porcine and mouse, embryonic tissue precursors were performed under general anaesthesia (2.5 percent Avertin in PBS, 10 milligrams per kilogram intraperitoneally). Host kidney was exposed through a left lateral incision. A 1.5-mm incision was made at the caudal end of the kidney capsule and donor precursors were grafted under the kidney capsule in fragments 1-2 millimeter in diameter.

Transplant Growth Analysis:

The animals receiving implants were sacrificed at 6-8 weeks following transplantation. Organs bearing the transplanted grafts were then removed and either fixed in 10 percent paraformaldehyde or kept frozen. Fixed grafts in paraformaldehyde were dehydrated, embedded in paraffin and sequentially sectioned and mounted on slides coated with poly-L-lysine and sections were stained by hematoxylin-eosin (H+E).

The long (L) and short (W) axes of the grafts were measured and the post/pretransplant size ratio was calculated by multiplying L×W, both for the original (pretransplant) and the graft at the time of sacrifice.

Transplant Differentiation Analysis:

Immunohistochemical staining for porcine pancreatic markers included insulin, glucagons, pancreatic polypeptide, chromogranin, specific pancreatic cytokeratin (CK116) and vimentin (V9). Lung grafts were stained with porcine cytokeratin and vimentin. Spleen grafts were stained with porcine Factor VIII.

Functional Response Analysis:

Serial bleedings at 2, 4, 6, and 8 weeks posttransplantation were performed from the retro-orbital plexus. Serum was separated and kept frozen for porcine albumin and insulin ELISAs.

Immunosuppression Protocols:

Gestation age E42 fetal porcine pancreas was transplanted into NOD-SCID or immunocompetent C57BL/6 mice with different immunosuppression regimens. The successful regimens were:

1. Rapamycin at 1.5 milligrams per kilogram administered subcutaneously on a daily basis from day 0+CTLA4-Ig 200 micrograms per mouse given IP on days 0, 2, 4, 6 after transplantation.

2. Rapamycin at 2.5 milligrams per kilogram on days 0-4 and then 1.5 milligrams per kilogram on a daily basis, administered subcutaneously+CTLA4-Ig 200 micrograms per mouse administered intraperitoneally on days 0, 2, 4, 6 after transplantation.

3. Rapamycin at 1.5 milligrams per kilogram administered subcutaneously on a daily basis from day 0+CTLA4-Ig 200 micrograms per mouse and anti-CD40 ligand 250 micrograms per mouse administered intraperitoneally on days 0, 2, 4, 6 after transplantation.

4. Rapamycin at 1.5 milligrams per kilogram administered subcutaneously on a daily basis starting on day 0 for 2 weeks+CTLA4-Ig 200 micrograms per mouse and anti-CD40 ligand 250 micrograms per mouse administered intraperitoneally on days 0, 2, 4, 6 after transplantation.

5. Rapamycin at 1.5 milligrams per kilogram administered subcutaneously on a daily basis from day 0+CTLA4-Ig 200 micrograms per mouse administered intraperitoneally on days 0, 2, 4, 6 after transplantation+COP1 0.2 milligrams per mouse administered subcutaneously on a daily basis from day -7.

Experimental Results:

Identification of Gestational Stages of Porcine Pancreatic, Splenic and Pulmonary Grafts Capable of Optimal Organ-Specific Differentiation:

The potential to induce teratomas, as opposed to fully committed tissue development, was defined in different tissue precursors at different time points of the porcine embryonic development, by implantation into SCID mice.

Implantation of lung precursor tissue, similar to implantation of 24-day gestational stage pancreas, was not associated with teratomas. However, this outcome likely reflects entirely different causes as can be deduced from the growth potential of the two tissues. Whereas pancreatic tissue grafts are associated as early as day 24 of gestation with marked growth and development in the absence of teratoma formation, implantation of lung embryonic tissue does not exhibit appreciable growth potential prior to or at day 42 of gestation. At this relatively late gestation time the presence of pluripotential embryonic stem cells might be diminished in most of the embryonic tissues. Surprisingly though, fully functional organs were generated.

Identification of Gestational Stages of Porcine Pancreatic, Pulmonary and Splenic Grafts Enabling Optimal Organ-Specific Development with No/Minimal Risk of Teratoma Formation Following Transplantation:

Following the establishment of the earliest gestational time points at which grafts present no or minimal teratoma risk, transplantation experiments were performed to identify gestational stages of gestational stage porcine pancreatic, pulmonary and splenic grafts optimal for development of such organs/tissues.

Pancreatic Organ/Tissue Grafts:

Table 1 shows the development of pancreatic organ/tissue grafts, based on histological analysis of transplanted tissue. The embryonic pancreas precursor tissues, obtained at different gestational ages, were implanted under the kidney capsule. Tissue growth and development were evaluated 6 weeks after implantation.

Gestational stages of porcine pancreas organ/tissue grafts capable of generating growing, structurally and functionally differentiated, insulin-secreting, pancreatic tissues in the absence of teratoma formation following transplantation were identified. None of the implanted mice exhibited teratoma growth. Histological analysis of growing embryonic porcine pancreatic precursor tissue revealed that pancreas development following implantation of all stages is free of teratoma risk and displays marked growth and development, as exemplified by the presence of fully developed exocrine and endocrine components of the pancreas. At E42 pancreatic components are positively stained to cytokeratin 20, characterizing the pancreas epithelium, and the donor origin of the pancreatic epithelium is demonstrated by selective staining for cytokeratin MNF116, which is not cross-reactive with mouse epithelial cells. FIGS. 1a-f show immunohistological staining of an E42 porcine pancreas graft 6 weeks after transplantation. H&E staining (FIG. 1a), cytokeratin 20 (FIG. 1b), vimentin (v9) (FIG. 1c), anti-mouse CD31 (FIG. 1d), insulin (FIG. 1e), Ki67 (FIG. 1f).

TABLE 1

Development of teratoma versus specific organ growth following transplantation of fetal porcine pancreas.

| Porcine pancreas precursors | Histological findings | | |
|---|---|---|---|
| gestational age | Ducts and acini | Islets | Teratoma-like structures |
| E-24 | 6/10 | 4/10 | 0/10 |
| E-28 | 7/12 | 6/12 | 0/12 |
| E-42 | 14/15 | 12/15 | 0/15 |
| E-56 | 9/13 | 11/13 | 0/13 |
| E-80 | 8/10 | 7/10 | 0/10 |
| E-100 | 2/7 | 2/7 | 0/7 |

The transplanted fetal porcine graft, harvested at about E42 to about E56 remains functional for extended periods of time, as seen in FIGS. 2a-e. An E56 fetal pancreatic organ/tissue graft is shown three months posttransplantation. The graft is vascularized (FIG. 2a), stains positively for H&E (FIG. 2b) and remains positive for insulin (FIG. 2c), pancreatic polypeptide (FIG. 2d) and Ki67 (FIG. 2e). Functionality of the islets is documented by positive staining for porcine insulin, glucagon and pancreatic polypeptide. Similarly to mature islet organization, most of the cells within the grafts' islets secrete insulin, while glucagon secretion is detected only in the islets' periphery. The neuroendocrine origin of the islet cells is supported by positive staining for chromogranin.

Surprisingly, when functionality assays were carried out, the later stage fetal grafts performed much better.

Table 2 shows the graft size and serum levels of porcine insulin after transplantation of porcine embryonic pancreas of different gestational ages, 6 weeks posttransplantation.

Analysis of pancreatic precursor tissue obtained at different gestation time points revealed that insulin secretion is optimal upon transplantation of 28- to 56-day gestational stage pancreatic embryonic precursors relative to tissues obtained at day 80 of gestation which exhibited a markedly reduced ability to secrete insulin.

TABLE 2

Optimal growth and functional differentiation (insulin secretion) of pancreatic organs derived from E28-E56 porcine pancreatic xenografts

| | Gestational stage of grafts* | | | | | |
|---|---|---|---|---|---|---|
| | E24 (n = 6) | E28 (n = 7) | E42 (n = 14) | E56 (n = 14) | E80 (n = 10) | E100 (n = 5) |
| Graft size (mm$^2$ ± SD) | 11.3 ± 8.6 | 15.7 ± 11.2 | 33.7 ± 15.5 | 29.3 ± 13.2 | 7.8 ± 8.8 | 0.2 ± 0.07 |
| Porcine insulin (mIU/ml ± SD) | 2 ± 1.5 | 4.2 ± 3.3 | 5.1 ± 4 | 5.9 ± 7.1 | 1.2 ± 1.4 | 0.6 ± 0.7 |

To evaluate in-vivo the functionality of pancreatic organ/tissue grafts, porcine insulin secretion in the serum of transplanted mice was monitored via ELISA. Physiological levels of porcine insulin secretion were detected following implantation of pancreatic organ/tissue grafts implanted at different gestational stages.
*number of engraftments shown in parentheses The ability of the grafts to secrete insulin into the serum of NOD-SCID recipient mice was followed by specific ELISA, in which the primary porcine anti-insulin antibody does not cross-react with mouse insulin. A summary of the porcine insulin levels 6 weeks after transplantation detected in mice with porcine pancreatic organ/tissue grafts obtained at different gestational ages is shown in FIG. 3. Additionally, prior to implantation these embryonic tissue precursors were found to be substantially vascularized as indicated by staining with anti-CD31 antibody. FIGS. 4a-d show that porcine endothelial cells (lining along blood vessels) marked by CD-31 positive staining (dark, and arrow) are demonstrated in embryonic pancreas of various gestational ages. FIGS. 4a-d represent gestational stages E24, E27, E35 and E42, respectively.

The above results demonstrate that a fetal porcine graft at greater than E28 but less than E80, preferably E42 to about E56, generates a functional, host-vascularized pancreas. Both the graft size and insulin secretion levels are greater in the grafts from the E42-E56 embryos than from the E24-E28 embryos.

Table 3 shows the results of a glucose challenge test in NOD-SCID mice transplanted with fetal pancreas tissue. T-zero (T0) refers to the transplantation day while T30 refers to 30 days posttransplantation. Gestational age refers to the age at which the fetal porcine graft was harvested.

FIG. 5 shows the long term follow-up of porcine insulin levels detected in the serum of NOD-SCID mice. FIGS. 5a-d represent porcine insulin levels secreted from pancreatic E28, E35, E42 and E56 gestational stage tissues.

FIG. 6 shows the normalization of glucose levels in NOD-SCID mice transplanted with E42 fetal porcine pancreas grafts, following alloxan treatment (see Example 3 hereinabove). Alloxan selectively kills the mouse pancreas and leaves the transplanted porcine pancreas intact. This experiment unequivocally shows the survival and functionality of the transplanted pancreatic tissue.

TABLE 3

Glucose and insulin levels in mice transplanted with porcine fetal pancreas

| | T0 | | T30 | |
|---|---|---|---|---|
| Gestational age | Glucose mg/dl (average ± sd) | Insulin mIU/ml (average ± sd) | Glucose mg/dl (average ± sd) | Insulin mIU/ml (average ± sd) |
| E24 | 72 ± 7 | 0.85 ± 0.7 | 537 ± 47 | 2.1 ± 2.9 |
| E42 | 61 ± 10 | 2.8 ± 2.9 | 429 ± 148 | 9 ± 5.9* |
| E56 | 67 ± 25 | 1.7 ± 3.4 | 442 ± 112 | 12.6 ± 8.7** |
| E80 | 57 ± 11 | 0.9 ± 3.5 | 478 ± 75 | 1.9 ± 3.4*** |
| E100 | 53 ± 7 | 0.09 ± 0.02 | 387 ± 53 | 0.02 ± 0.05 |

*p < 0.002
**p < 0.0001
***p < 0.02

Isolation and transfer of human PBMCs. Human PBMC were generated from buffy coats obtained from normal volunteers, layered onto Ficoll-Paque solution and spun at 2000 rpm for 20 min. The interface layer was collected, washed twice, counted, and resuspended to the desired cell concentration. 80 human cells were injected intraperitoneally, 1-3 days after transplantation of the human or pig pancreatic precursors into NOD-SCID mice. Control mice did not receive human PBMC.

The immunogenic response of porcine fetal grafts was determined from mice transplanted with fetal porcine pancreas grafts harvested from different gestational ages. Table 4 shows the histological results that characterize the pancreas transplants following infusion of human peripheral blood mononuclear cells (PBMCs) into the host immunodeficient SCID mice.

This semi-quantitative grade reveals increasing cellular infiltration and fibrosis with decreasing amounts of pancreatic components as the grafts' gestational age increases (E56 to E100), reaching statistical difference when comparing cellular infiltration in the E42 vs. E80 and E100 grafts (p<0.03). In addition, 6 weeks after transplantation, complete destruction and fibrosis appear in grafts obtained at E80 or E100 compared with earlier transplanted pancreatic precursors. However, in E42 and E56 grafts pancreatic tissue is still detected, despite the presence of human-PBMCs (stained for anti-human-CD45).

TABLE 4

Histological findings characterizing pig pancreatic transplants following infusion of human PBMCs into NOD-SCID mice.*

| Gestational stage | Without Human PBMCs | | | | With Human PBMCs | | | |
|---|---|---|---|---|---|---|---|---|
| | Islets | Ducts/ acini | Cellular infiltrate | Fibrosis | Islets | Ducts/ acini | Cellular infiltrate | Fibrosis |
| E24 | 0.75 ± 0.5 | 0.75 ± 0.5 | 0.5 ± 0.6 | 0.5 ± 0.5 | 0.3 ± 0.5 | 0.6 ± 0.6 | 1.3 ± 0.6 | 1.3 ± 0.6 |
| E28 | 1.6 ± 0.6 | 1.6 ± 0.6 | 0.7 ± 0.6 | 1 ± 1 | 0.3 ± 0.6 | 1.3 ± 0.6 | 1.3 ± 0.6 | 1.7 ± 0.6 |
| E42 | 2.8 ± 0.4 | 2.6 ± 0.5 | 0.8 ± 0.8 | 1.2 ± 0.4 | 1.8 ± 0.8 | 1.8 ± 0.8 | 2 ± 0.7 | 1.6 ± 0.5 |
| E56 | 2.75 ± 0.5 | 2.75 ± 0.5 | 0.25 ± 0.5 | 0.75 ± 0.5 | 1.4 ± 0.5 | 1.75 ± 0.5 | 2.5 ± 0.4 | 2.12 ± 0.2 |
| E80 | 1.3 ± 0.6 | 1.7 ± 0.6 | 0.7 ± 0.6 | 1.7 ± 0.6 | 0.7 ± 0.6 | 1.5 ± 0.5 | 3 ± 0 | 2.3 ± 0.3 |
| E100 | 0.8 ± 0.5 | 0.3 ± 0.6 | 0.3 ± 0.5 | 3 ± 0 | 0.3 ± 0.6 | 0.3 ± 0.6 | 3 ± 0 | 2.3 ± 0.6 |

*Semi-quantitative grade to various histological components:
Islets- 1+, 1 islet; 2+, 2-4; 3+, >4 islets per HPF.
Ducts and acini- 1+, 1-2; 2+, 2-5; 3+, >5 ducts/acini per HPF.
Cellular infiltration (human CD45-positive cells)- 0-1+, sapres infiltrate; 2+, focal dense infiltrate; 3+, diffuse dense infiltrate.
Fibrosis grading: 1+, loose connective tissue; 2+, focal distribution of dense fibrosis; 3+, dense distributed fibrosis.

FIGS. 7a-d show the level of tissue rejection of porcine embryonic pancreatic tissues (E56 and E80) mediated by human PBMCs, 6 weeks after transplantation under the kidney capsule in NOD-SCID mice. FIG. 7a shows H&E staining of E56 pig pancreatic tissue. The tissue is focally infiltrated by human PBMCs (arrows), while other components of the pancreas such as acini (arrowhead) or islets (asterisk) can be detected. FIG. 7b shows focal infiltration of human PBMCs in the E56 graft as stained for anti-human CD45. FIG. 7c shows H&E staining of an E80 pancreatic organ/tissue graft. The graft undergoes tissue destruction, fibrosis, and focal hemorrhages with minimal residues of the pancreatic tissue. FIG. 7d shows human PBMCs stained with anti-human CD45 antibody invading the E80 pancreatic organ/tissue graft.

FIGS. 8a-c shows the pancreatic tissue harvested from a fetal porcine donor gestational age E42. FIG. 8a shows the tissue in a NOD-SCID mouse, while FIG. 8b shows the tissue in an immunocompetent C57BL/6 mouse. FIG. 8c shows the tissue in a mouse treated with the following immunosuppressive regimen: rapamycin administered subcutaneously at 1.5 milligrams per kilogram on a daily basis from day 0+200 micrograms CTLA4-Ig per mouse (i.e. 8 milligrams per kilogram), and 250 micrograms anti-CD40 ligand antibody per mouse (i.e. 10 milligrams per kilogram) administered intraperitoneally on days 0, 2, 4, 6 after transplantation. The immunosuppressive regimen allows survival of the porcine tissue and overcomes any problems of immune rejection. This protocol corresponds to immunosuppression regimen number 3 described under the Materials and Methods section, above.

Example 7

Identification of Gestational Stages of Functional Porcine Pulmonary Grafts Capable of Significant Organ-Specific Development with No/Minimal Risk of Teratoma Formation For details of Material and Methods, see Example 6, supra. Identification of gestational stages during which porcine pulmonary grafts are capable of generating, with no/minimal risk of teratoma formation, growing, normally differentiated alveolar pulmonary tissues following transplantation into xenogeneic recipients: In contrast to kidney, liver, pancreas or heart embryonic tissue implantation, implantation of porcine lung tissue grafts at 24, 28 or even 42 days of gestation, did not lead to significant growth. Pulmonary tissue growth and differentiation was only detected following implantation of precursor tissue at the relatively late gestational stage of 56 days. Following subcapsular implantation of lung tissue at a gestational stage of 24, 28 or 42 days no teratoma formation was detected and only some epithelial and fibrous cells were found 6 weeks posttransplantation. However, as can be seen in FIGS. 9a-d, 56-day gestational stage lung precursor grafts displayed impressive growth (FIG. 9a), and developed into mature lung tissue containing all respiratory system elements including respiratory bronchi, bronchioles and alveoli (FIG. 9b, arrow, asterisks, arrow heads, respectively), and cartilage (intense blue staining by alcian-blue FIG. 9c). Appropriate types of epithelial cells for lung tissue were detected lining the different lung structures. Importantly, as can be seen in FIG. 9d, the alveoli generated from the 56-day gestational stage grafts exhibited thin inter-alveolar septa comprising capillary plexuses within, supported by minimal amounts of fine connective tissue, fulfilling the fine perfusion-ventilation balance requirement for enabling extra-uterine gas exchange. Although 80-day gestational stage porcine lung grafts also developed into lung tissue, the developed tissues were significantly smaller than those derived from 56-day gestational stage grafts ($p<0.001$). In addition to the suboptimal growth potential, abnormal microscopic findings including alveolar wall thickening and epithelial dysplasia, were evident. The differences in alveolar wall structure and thickness of lung tissues generated by 56- and 80-day gestational stage implants can readily be seen in FIGS. 4d-e, respectively, following H&E staining.

Discussion:

Thus, it is hard to know if engraftment failure of fetal porcine tissues reported in large animal studies or in humans, is only mediated by rejection or could also be attributed to a choice of embryonic tissue with weak growth potential collected at sub-optimal gestation time. This issue is clearly illustrated by the present data which shows that the optimal gestational stage for pancreatic organ/tissue graft implantation is between days 28 to 56 of gestation, while the growth potential and insulin secretion capacity is significantly reduced upon implantation of tissue obtained beyond day 80 of gestation, at which time most of the transplants in humans were carried out (Reinholt F P. et al., 1998. Xenotransplantation 5:222-5; Groth C G. et al., 1998. Transplantation Proceedings 30:3809-10).

While establishment of the upper gestational stage threshold above which teratomas are unlikely to develop following graft transplantation was achievable for all of the tested organ/tissue types, defining the lower gestational stage threshold below which potential growth is suboptimal represented a more difficult challenge for organ types, such as lung, whose functional performance cannot be established by secretion of a protein into the blood, as is the case with pancreas or spleen.

Contrary to the gestational stage time window identified for pancreatic grafts, early gestational stages were not favorable for development of gestational stage pulmonary grafts. Thus, development of E28- to E42 gestational stage pulmonary grafts was not observed, while rapidly growing and differentiated lungs containing essentially all components of the adult respiratory tree, including mature alveoli, were formed following implantation of E56- or E80 gestational stage pulmonary grafts. At a gestational stage of 80 days, however, gestational stage pulmonary grafts were unexpectedly found to be suboptimal since these exhibited both decreased growth potential and suboptimal pulmonary tissue development characterized by alveolar wall thickening and epithelial dysplasia.

Conclusion:

The presently described data unexpectedly demonstrate for the first time that there exist for each of porcine gestational stage pancreatic or pulmonary organs/tissues, gestational stages during which grafts of such organs/tissues have the capacity to generate, with no/minimal risk of teratoma formation and minimal host immune response, growing, structurally and functionally differentiated organ-specific tissues following transplantation. The presently disclosed data further unexpectedly demonstrates for the first time that such gestational stage porcine organs/tissues each have distinct gestational stages during which these have the capacity to generate, with no/minimal risk of teratoma formation, growing, structurally and functionally differentiated organ-specific tissues following transplantation. Thus, the presently disclosed data unexpectedly succeeded in characterizing for the first time, for each of such organs/tissues, the gestational stages of grafts during which these have the capacity to generate, with no/minimal risk of teratoma formation, growing, structurally and functionally differentiated organ-specific tissues following transplantation. In particular, the presently disclosed data unexpectedly demonstrate for the first time that porcine pancreatic organ/tissue grafts at gestational stages ranging from about day 24 to about day 80 have the capacity to generate, with no/minimal risk of teratoma formation, growing, structurally and functionally differentiated, insulin-secreting pancreatic tissues following transplantation, with those at gestational stages ranging from about day 28 to about day 56 having the capacity to generate optimally growing and structurally and functionally differentiated, insulin-secreting pancreatic tissues.

Moreover, the presently disclosed data unexpectedly demonstrate for the first time that porcine splenic grafts at gestational stages ranging from about day 24 to about day 80 with those at gestational stages ranging from about day 42 to about day 56 having the capacity to generate, with no/minimal risk of teratoma formation, optimal growing, structurally and functionally differentiated spleen tissue.

Additionally, the presently disclosed data unexpectedly demonstrate for the first time that the optimal gestational stage for transplantation of porcine pulmonary grafts is at about day 42 and less than about day 80 of gestation, with 56-day gestational stage grafts having the capacity to generate, with no/minimal risk of teratoma formation, optimally growing and structurally and functionally differentiated pulmonary tissues.

As such, the presently described methods of transplanting porcine gestational stage pancreatic, and pulmonary grafts are overwhelmingly superior to known methods, and are therefore optimal for treating diseases associated with failure of organs of such types.

Example 8

Identification of Gestational Stages During which Mouse Splenic Grafts are Capable of Generating Growing Splenic Organs Background:

Numerous highly debilitating/lethal diseases caused by abnormal activity or expression of a biomolecule for which there are no optimal treatment methods are associated with a deficiency in a substance which is produced by hematopoietic/stromal cells which may be found in lymphoid/hematopietic organs/tissues such as spleen. Such diseases include, for example, hemophilia A or Gaucher disease which are respectively associated with factor VIII or glucocerebrosidase deficiency.

The present invention provides a method to treat such diseases comprising transplantation of fetal allogeneic lymphoid/hematopietic organs/tissues which would have the great advantage of obviating the requirement for enzyme replacement therapy, the state-of-the-art treatment method for such diseases. However, to date, it is unknown whether and how it may be possible to optimally achieve such therapeutic transplantation in the absence of teratoma formation. While conceiving the present invention, the present inventors hypothesized that lymphoid/hematopietic organ/tissue grafts at the appropriate gestational stage would have the capacity to generate growing, normally differentiated splenic organs with no/minimal risk of teratoma formation following transplantation and minimal host immune response into a syngeneic/allogeneic host. Thus, while reducing the present invention to practice, the present inventors have successfully validated this hypothesis, as described below, thereby overcoming critical limitations of the art.

Materials and Methods:

For details see Example 6, supra. Transplantation of gestational stage splenic grafts into syngeneic/allogeneic mouse recipients: The earliest gestational stage during which spleen is distinguishable from other organs and separable from the pancreas in mice is at about day 13 of gestation, therefore 13-, 14-15-, 16- or 17-day gestational stage mouse splenic grafts were transplanted under the kidney capsule of host syngeneic or allogeneic mice, and their growth and development was analyzed.

Experimental Results:

Syngeneic/Mouse Transplantation Model:

Identification of optimal gestational stages of splenic grafts for generation of normally differentiated splenic organs with no/minimal risk of teratoma/fibrosis formation following implantation in syngeneic hosts: Mouse splenic grafts at days 13, 14, 15, 16 or 17 of gestation were transplanted into syngeneic recipients, and their development was analyzed histologically 6 weeks posttransplantation.

As can be seen from the results which are summarized in Table 5, grafts at days 13 or 14 of gestation formed disorganized mesenchymal tissues, however with evidence of diffuse lymphoid cell infiltration, and formation of lymphoid areas with lacunae and enlarged sinuses with red and white pulp components. In sharp contrast, tissues derived from 15- or 16-day gestational stage splenic grafts generated tissues exhibiting good organization of both stroma and lymphoid tissue with more mature trabeculae and follicle structures, white and red like pulp areas appearing more clearly than in tissues generated by earlier stage grafts, and occurrence of encapsulation. Occasionally, empty mesenchymal stroma structures with minimal colonization by lymphoid cells were noted. Implantation of grafts at day 17 of gestation led to tissues exhibiting well defined white and red pulps. In the white pulp, formation of T- and B-cell compartments was clearly demonstrated via double-immunostaining.

As indicated in Table 5, cystic teratoma-like structures were found in one out of seven mice implanted with a splenic graft at day 13 of gestation. Surprisingly and in sharp contrast, 14-day gestational stage splenic grafts generated splenic organs lacking teratoma formation, exhibiting splenic differentiation with lymphoid areas corresponding to the white pulp in adult spleen, and exhibiting trabeculae, sinus-like structures and central arteries.

TABLE 5

Identification of optimal gestational stage of gestational stage splenic grafts for generation of normally differentiated splenic organs with no/minimal risk of teratoma/fibrosis formation

| | | Incidence of splenic development | | | |
|---|---|---|---|---|---|
| Gestational stage of graft (days) | Incidence of non-splenic development | Mesenchymal organization | Incidence of lymphoid follicle formation | Incidence of red pulp formation | Incidence of diffuse lymphocytes and small clusters |
| 13 | 1\7-teratoma 2\7-fibrosis | ++ | 2\7 | 2\7 | 2\7 |
| 14 | 2\14 fibrosis | +\++ | 2\14 | 8\14 | 9\14 |
| 15 | 3\10 fibrosis | ++\+++ | 4\10 | 7\10 | 3\10 |
| 16 | | ++\+++ | 1\4 | 3\4 | 3\4 |
| 17 | | ++\+++ | 3\4 | 3\4 | 1\4 |

The data shown summarizes results of 11 unrelated experiments in which grafts between days 13 to 17 of gestation were transplanted into syngeneic C57BL/6 or Balb/c mice. (+), chaotic stroma; (++), some organization with few sinuses and trabeculae; (+++), normal spleen-like organization.

Allogeneic/Mouse Transplantation Model:

Transplantation of splenic grafts at all gestational stages into allogeneic recipient mice resulted in graft rejection with generation of major fibrosis at the graft area. No signs of graft survival were seen 6 weeks post-transplantation.

Characterization of splenocyte lineage population profiles during mouse spleen development: The lymphoid, myeloid or mesenchymal origin of single-cell suspensions of spleens from neonates, 4 week-old mice and 8 week-old mice were phenotyped by FACS analysis. Antibodies used included antibodies against CD3, CD4, CD8, CD11b, CD11c, CD29, CD44, CD49e, B220, Sca, Gr-1 and H2B. The relative levels of the different phenotypes during spleen development is shown in Table 6.

TABLE 6

Characterization of hematopoietic lineage profiles during mouse spleen maturation.

| Marker analyzed in graft-derived tissues | Developmental stage | | | | | | | |
|---|---|---|---|---|---|---|---|---|
| | 14-days of gestation | 15-days of gestation | 17-days of gestation | 18-days of gestation | Neonatal | 1 week old | 4 weeks old | 8 weeks old |
| CD3 | + | + | | + | ++ | − | ++ | + |
| CD4 | | − | − | − | − | − | + | + |
| CD8 | | − | − | − | − | − | ++ | ++ |
| B220 | | + | + | − | ++ | + | +++++ | +++++ |
| CD11b | | ++ | +++ | +++ | | + | + | + |
| CD11c | | | − | | | − | +++ | +++ |
| Gr-1 | | ++ | + | + | | + | + | + |

TABLE 6-continued

Characterization of hematopoietic lineage profiles during mouse spleen maturation.

| Marker analyzed in graft-derived tissues | 14-days of gestation | 15-days of gestation | 17-days of gestation | 18-days of gestation | Neonatal | 1 week old | 4 weeks old | 8 weeks old |
|---|---|---|---|---|---|---|---|---|
| H2-K$^b$ | | | +++ | +++ | +++++ | ++++ | +++++ | +++++ |
| integrin-beta1 (CD29) | + | | | +++ | +++++ | +++++ | ++++ | +++ |
| Pgp-1 (CD44) | | | | +++ | +++++ | +++++ | +++++ | |
| integrin-alpha5 (CD49e) | | | | ++ | +++ | +++++ | ++ | |
| Sca-1 (Ly6A/E) | − | | | | − | + | + | +++++ | +++++ |

Key index: percent of total splenocytes. (−), 0-10 percent; (+), 10-20 percent; (++), 20 30 percent; (+++), 30-40 percent; (++++), 40-50 percent; (+++++), 50-100 percent.

Analysis of levels of splenocytes displaying the lymphoid-specific markers CD4, CD8 and B220 indicate that splenic T- and B-cell populations are present at basal levels until one week after birth and begin to increase afterwards according to spleen maturation. Surprisingly, the CD3 phenotype did not correlate with the CD4 and CD8 phenotypes and occurred earlier. The CD3+ CD4-CD8—could represent NK T cells or other non-T cells.

Levels of splenocytes displaying the macrophage-specific marker CD11b, or the dendritic cell-specific marker CD11c were analyzed during splenic maturation. Macrophages were found to be present in spleen throughout post-gestational development, however the levels of such cells were surprisingly found to decline during the course of spleen maturation. In significant contrast, levels of dendritic cells were found to increase during the course of spleen maturation.

Gestational stage splenic grafts have the capacity to generate splenic organs harboring host-derived lymphoid and myeloid cells following transplantation into allogeneic hosts: In order to distinguish hematopoietic cells of host and donor origin within tissues generated by gestational stage splenic grafts, 14-day gestational stage grafts from wild type C57BL/6 mice, which express the CD45 isotype Ly5.2 in hematopoietic lineage cells, were transplanted into B6SJL mouse recipients which express the CD45 isotype Ly5.1 instead. FACS analysis of tissues generated by the grafts unexpectedly showed that the growing tissue contained lymphoid cells of host origin. Therefore, it was concluded that such grafts give rise to splenic stromal/mesenchymal tissue capable of accommodating colonization by allogeneic host lymphocytes. Relatively high levels of CD4+ and CD8+ lymphocytes, as well as of B220+ B-cells, were documented in the growing graft-derived splenic organs. This data suggests that after 6 weeks of development the lymphoid cell constitution of the graft-derived spleen resembles that of a normal spleen at 3-4 weeks after birth. The graft-derived tissues were also found to harbor macrophages of host origin. In tissues generated by 15-day gestational stage allogeneic splenic grafts, the cell composition of the growing organ was similar to that generated by the 14-day gestational stage grafts, however higher levels of macrophages were documented.

Irradiation induces enhanced splenic maturation and hematopoiesis in splenic organs derived from gestational stage splenic grafts transplanted into allogeneic recipients: In mice, hematopoiesis occurs in the spleen and is markedly enhanced following irradiation. While conceiving the present invention, the present inventors theorized at it might be possible to employ irradiation to enhance hematopoiesis in the presently described context of tissues generated by gestational stage splenic grafts following transplantation in allogeneic recipients. However, it was unknown whether irradiation could indeed result in enhanced hematopoiesis in this novel context, and which irradiation modality could be used to achieve such enhancement. Thus, in order to attempt to elucidate these issues, recipient mice of allogeneic 15-day gestational stage splenic grafts were subjected to varying sub-lethal/lethal doses of total body irradiation (TBI), and the effect of such irradiation on hematopoiesis within the grafts was analyzed. 300, 600 or 1000 rad total body irradiation (TBI) of graft recipient mice induced in the grafts adult-type stromal and follicular white pulp organization, and formation of trabecules, sinuses, and hematopoietic areas with megakaryocytes and granulocyte maturation. In sharp contrast, no such mature splenic structures were detected in control non-irradiated recipients. In addition, the size of the grafted organs was found to be larger in the irradiated as compared to the non-irradiated hosts.

Upon 1000 rad irradiation and radioprotection with syngeneic or NOD-SCID bone marrow, 3 out of 12 14-day gestational stage splenic grafts transplanted into allogeneic recipients generated teratoma like structures accompanied by spleen growth.

Summary:

Transplantation of mouse 13-day gestational stage splenic grafts into allogeneic/syngeneic hosts is capable of generating graft-derived teratomas, whereas normal splenic development without teratoma formation was achieved by transplantation of splenic grafts at a developmental stage at least as advanced as 14 days of gestation. In general, in 13- to 17-day gestational stage grafts, the capacity of such grafts to exhibit splenic differentiation was found to increase with increasing gestational stage. Total body irradiation of recipients with 300 rad or higher was found to lead to accelerated maturation and growth of gestational stage splenic grafts. Results from experiments in the allogeneic model revealed that the hematopoietic compartment in the growing spleen is of host origin unlike the mesenchyme which is of donor origin.

Conclusion:

The above-described results demonstrate for the first time that gestational stage lymphoid/hematopietic organ/tissue grafts, such as splenic grafts, have the capacity to generate growing, normally differentiated mesenchymal stroma in which host lymphopoiesis can take place lymphoid/hematopietic organs/tissue in the absence of teratoma formation following transplantation into syngeneic, or immunodeficient allogeneic recipients. The above-described results furthermore identify for the first time gestational stages during which such grafts optimally have such capacity. As such, since spleen and other lymphoid/hematopietic organs/tissues have the capacity to produce substances whose deficiency is associated with a disease, such as factor VIII or glucocerebrosidase deficiency in hemophilia A or Gaucher disease, respectively, the above-described transplantation methods can be used for optimally treating such a disease in a subject relative to known methods.

Example 9

Porcine Spleen Transplantation

The following experiments were performed in order to identify gestational stages during which porcine splenic grafts following transplantation into xenogeneic recipients are capable of generating growing, normally differentiated splenic organs with no/minimal risk of teratoma formation and minimal immunosuppression.

Background:

Numerous highly debilitating/lethal monogenic diseases for which there are no optimal treatment methods are associated with a deficiency in a substance which is produced by hematopoietic/mesenchymal cells which may be found in lymphoid/hematopietic organs/tissues such as spleen. Such diseases include, for example, hemophilia A or Gaucher disease which are respectively associated with factor VIII and glucocerebrosidase deficiency. One strategy which has been proposed to treat such diseases involves transplantation of fetal xenogeneic lymphoid/hematopietic organs/tissues which would have the great advantages of providing a essentially unlimited source of transplantable tissues, and of obviating the requirement for enzyme replacement therapy, the state-of-the-art treatment method for such diseases. However, to date, it is unknown whether and how it may be possible to optimally achieve such therapeutic transplantation in the absence of teratoma formation.

While conceiving the present invention, the present inventors discovered that lymphoid/hematopietic organ/tissue grafts at the appropriate gestational stage has the capacity to generate growing, normally differentiated splenic organs with no/minimal risk of teratoma formation and minimal immunosuppression following transplantation into a xenogeneic host.

The present inventors have unexpectedly determined that the optimal time window for transplantation of porcine fetal spleen tissue, when considering all the factors i.e. functionality, organogenesis, risk of teratoma formation and immunosuppression, is about E42 to about E56

Materials and Methods:

Real-time PCR: Graft-derived tissues were carefully dissected from the subcapsular implantation site, and total RNA was isolated therefrom using the Tri-Reagent® method (Molecular research center, Inc., Cincinnati, Ohio), according to the manufacturer's instructions, and treated with RQ1 RNase-Free DNase (Promega Corp. Madison, Wis.). The purified RNA was reverse-transcribed into cDNA, and the cDNA was used as template for quantitative PCR analysis of mRNA transcripts in the grafts using a Light Cycler instrument (Roche Diagnostics Gmbh, Mannheim, Germany), according to the manufacturer instructions, using primers specific for porcine factor VIII [forward primer, 5'-CATG-GACCTGCTTCAC-3' (SEQ ID NO: 1); reverse primer, 5'-TGACACATGATTTAATCCCG-3' (SEQ ID NO: 2)]; and for the housekeeping genes: porcine transferrin receptor [forward primer, 5'-TGTGGCAGCTCAGAAT-3' (SEQ ID NO: 3); reverse primer, ACCGATGTGGTTACTCC-3' (SEQ ID NO: 4)], and mouse GAPDH [forward primer, 5'-CTGC-GACTTCAACAGC-3' (SEQ ID NO: 5); reverse primer, 5'-GGTGCAGCGAACTTTAT-3' (SEQ ID NO: 6)]. Quantitative PCR reactions were carried out in triplicate for each sample, and relative quantities of transcripts for each transplant were calculated on the basis of the corresponding amount of porcine transferrin receptor.

Experimental Results:

Porcine 28- to 80-day gestational stage splenic grafts exhibit extensive growth and development of splenic structures in the absence of teratomas following transplantation into immunodeficient xenogeneic recipients: Porcine splenic grafts at different gestational stages were transplanted into NOD/SCID or CB 17/ICR SCID mice to test the capacity of such grafts to generate splenic organs and teratomas following transplantation into immunodeficient xenogeneic recipients. A summary of the results obtained in these experiments, describing development of the implanted gestational stage splenic grafts obtained at different gestational stages, is given in Table 7

As can be seen in Table 7, impressive growth was achieved by 28-, 42-, 56- and 80-day gestational stage grafts 6 weeks posttransplantation, with the 42- and 56-day gestational stage grafts growing to more than twice the size of 28- and 80-day gestational stage grafts. No teratoma growth was observed following transplantation of 28- to 80-day gestational stage porcine spleen precursors. The 28-day gestational stage grafts displayed splenic development characterized by organization of blood vessels and encapsulation of the graft-derived organ. Splenic organs derived from 42- and 56-day gestational stage implants were associated with a more heterogeneic structure comprising loose and condensed mesenchymal components, with the former exhibiting splenic vascularization, encapsulation, and a trabecular-like structure with lacunae likely corresponding to a sinus system lacking a lymphoid component which cannot be provided by the SCID hosts. Following transplantation of 80-day gestational stage grafts, a different phenotype appears characterized by well vascularized homogeneic stroma with emphasized zones of extracellular matrix, and by diffusion of inflammatory granulocytes and macrophages throughout the graft-derived splenic organ. FIGS. 10a-b show immunochemical staining with H&E and anti-vimentin (v9), respectively, of E42 transplanted porcine splenic tissue 6 weeks after transplantation.

Therefore, in agreement with the above-described findings in the syngeneic mouse model in which lymphocytes that inhabit the graft-derived splenic organ are essentially exclusively of host origin, the splenic grafts following transplantation into SCID recipients represent mostly stromal structures essentially lacking a lymphoid component. The porcine origin of the stromal elements in the graft-derived splenic organ was demonstrated by immunostaining with an antibody against porcine vimentin, which is specific for porcine mesenchyme, and colonization of the porcine graft-derived splenic stroma by xenogeneic host mouse macrophages was demonstrated by immunostaining with an antibody for the macrophage marker F4/80 which is mouse specific and non-cross-reactive with the porcine antigen.

Splenic organs derived from gestational stage porcine splenic grafts transplanted into xenogeneic recipients produce porcine factor VIII: Considering that there are several indications in the literature that factor VIII, which participates in the clotting cascade, is produced in the spleen tissue, the present inventors hypothesized that the presently described gestational stage porcine splenic grafts would be capable of producing useful substances, such as factor VIII, following transplantation into xenogeneic recipients. This would specifically demonstrate that the presently described transplantation method could be used to produce therapeutic levels of such a substance in a graft recipient having a disease, such as hemophilia A, which is associated with deficiency of a substance such as factor VIII. However, it was unknown whether the presently described grafts would indeed be capable of secreting factor VIII following xenotransplantation.

In order to more precisely quantitate levels of porcine factor VIII expression, precursors of porcine tissues and graft-derived tissues were analyzed via real-time RT-PCR assay. As can be seen in FIG. 11, expression of porcine factor VIII mRNA in the liver and spleen increases during gestation. Moreover, porcine spleens derived from adult or from embryonic E80 or E100 express high levels of porcine factor VIII mRNA, although slightly lower than the levels expressed by porcine liver derived from the same gestational stages, respectively. FIG. 11 shows the relative amounts of porcine factor VIII mRNA in different tissues before and after transplantation were evaluated by Real-time PCR using primers specific for porcine factor VIII. The results were divided by the expression of the house-keeping gene Beta-actin, using primers specific for the porcine Beta-actin. Total mRNA that was purified either from adult tissue or from E80 or E100 precursor tissue from porcine liver and porcine spleen served as positive control. Total mRNA that was purified from the mouse kidney, from an area distant from the embryonic implant, served as negative control.

Six weeks after transplantation of embryonic spleen tissue from E28, E42, E56 into immunodeficient mice, the spleen grafts exhibited significant levels of porcine factor VIII mRNA expression. In contrast, control gestational stage pancreatic and pulmonary grafts generated tissues which either did not express or exhibited markedly reduced levels of factor VIII mRNA, respectively. Such low levels of porcine factor VIII mRNA expression observed in tissues derived from the pulmonary grafts is likely due to the dense blood vessel network which was formed in such tissues.

Summary:

In agreement with the results in the allogeneic mouse transplantation model described above, porcine gestational stage splenic grafts implanted in SCID mice generated splenic organs characterized by mesenchymal growth and development in the absence of a lymphoid component. Transplantation of porcine 28- to 80-day gestational stage splenic grafts generated graft-derived splenic organs exhibiting similar histological organization in the absence of teratomas, with optimal growth and development and low host immune response being achieved using 42 and 56-day gestational stage implants. The splenic organs derived from gestational stage porcine splenic grafts exhibited significant levels of factor VIII mRNA expression, as defined by RT-PCR analysis.

Conclusion:

The above-described results demonstrate for the first time that gestational stage porcine lymphoid/hematopoietic organ/tissue grafts, such as porcine fetal splenic grafts, have the capacity to generate growing, normally differentiated lymphoid/hematopoietic organs/tissues in the absence of teratoma formation following transplantation into xenogeneic recipients. The above-described results furthermore identify for the first time gestational stages during which such grafts optimally have such capacity. As such, since such porcine grafts are available in essentially unlimited quantities, and since lymphoid/hematopoietic organs/tissues have the capacity to produce substances whose deficiency is associated with a disease, such as factor VIII or glucocerebrosidase deficiency in hemophilia A or Gaucher disease, respectively, the above-described transplantation methods are clearly superior to known methods of treating such a disease in a subject.

TABLE 7

Porcine E28- to E80-day gestational stage splenic grafts have the capacity to generate, with no/minimal risk of teratoma formation, extensively growing, normally differentiated splenic organs following transplantation into immunodeficient xenogeneic recipients

| Gestational stage of grafts (days) | Fraction of grafts displaying splenic differentiation* | Graft growth (square millimeters, average ± standard deviation) |
| --- | --- | --- |
| 28 | 14/17 | 30.6 ± 10.5 |
| 42 | 6/10 | 76 ± 9.9 |
| 56 | 4/5 | 70.6 ± 9 |
| 80 | 4/5 | 27 ± 19 |

*None of the grafts were observed to generate teratomas following transplantation. Grafts were analyzed 6 weeks posttransplantation.

Example 10

Hemophilia A Treatment Via Transplantation of Developing Xenogeneic Spleen

Abstract:

Previous clinical attempts to correct genetic deficiencies such as hemophilia A or Gaucher by transplantation of allogeneic spleen were unsuccessful, and were associated with aggressive graft versus host disease (GVHD), mediated by mature T cells in the donor spleen. In the present studies it is disclosed that fetal pig spleen harvested at the E42 stage, prior to appearance of T cells, exhibited optimal growth potential upon implantation into SCID mice, and the growing mesenchymal tissue expressed factor VIII mRNA. Implantation of E42 spleen precursor tissue into hemophilic SCID mice led to complete alleviation of hemophilia A within 3 months post-transplant, as demonstrated by tail bleeding, and by assays for Factor VIII blood levels. These results provide a proof of principle for the concept that implantation of embryonic spleen precursor tissue obtained prior to the appearance of T cells, could provide a novel treatment modality in hemophilia A and in other genetic deficiencies of an enzyme or a factor that can be produced by the growing spleen tissue.

Introduction:

Inherited genetic diseases represent natural targets for gene therapy, but considerable difficulties arise in targeting gene delivery to specific cell types in vivo, regulating the expression of recombinant genes, and controlling vector immunogenicity (1).

Inherited hemophilia A is thought to be a particularly promising gene therapy target, because the deficient protein (factor VIII) circulates systemically and can be synthesized, in theory, by various cell types. Indeed, preliminary trials have demonstrated expression of human factor VIII in animals and in patients following gene transfer (2-4). In parallel, progress in transplantation over the past decade, encouraged the consideration of cell or organ transplantation as a potential treatment for genetic diseases, such as hemophilia A.

The liver is considered to be the primary source of factor VIII protein. Hepatocytes and liver sinusoidal endothelial cells, but not Kupffer cells, produce factor VIII in the mouse liver (5). The role of the liver in factor VIII synthesis has been supported by liver transplantation studies in both hemophilic animals and humans, following which, increasing factor VIII levels were detected (6-8). Transplantation studies in hemophilic animals showed that organs such as spleen and lung also contribute to the presence of circulating factor VIII (9, 10).

The feasibility of spleen transplantation in the treatment of hemophilia A in humans was first documented in 1969 by Hathaway, who transplanted a spleen donated by a family member (11). The recipient displayed a marked rise in factor VIII shortly after the transplant, but the spleen graft had to be removed 4 days later due to severe rejection.

Subsequently, a number of spleen transplants (living donor or cadaveric) in hemophilic patients have been reported. At least one resulted in sustained, normalized levels of factor VIII with stable factor VIII production for 5 months after operation (12, 13). Little data are available regarding spleen transplantation in the treatment of other genetic diseases but there are several case reports in the literature suggesting the potential of spleen transplantation as a treatment for Gauche disease and hypogammaglobulinemia (13-15).

A major obstacle in spleen transplantation is associated with graft versus host disease (GVHD) mediated by donor T cells present in the spleen graft. In principle, this potentially lethal complication may be prevented if it were possible to use embryonic precursor spleen tissue obtained prior to the appearance of mature T cells in the spleen.

Considering the recent interest in fetal tissue as a source for transplantation, it is surprising that the role of embryonic spleen tissue as a source for secreted proteins has never been studied. Clearly, if early embryonic spleen tissue will prove feasible, it could be of particular importance, as this precursor tissue is devoid of T cells which are known to mediate GVHD typical of adult spleen transplantation.

In the present study, the potential of pig embryonic spleen tissue as a novel tissue source for transplantation was examined for the first time, with emphasis on relatively early gestational time points at which mature T cells are not found in the implant. The proof of concept, namely the ability to correct hemophilia A using early embryonic spleen tissue, was then demonstrated in factor VIII knock-out hemophilic SCID mice.

Materials and Methods:
Animals:

Animals were maintained under conditions approved by the Institutional Animal Care and Use Committee at the Weizmann Institute. A breeding pair of factor VIII KO mice was purchased from Jackson laboratory (strain name: B6; 129S4-F8tm1Kaz/J, stock number: 004424)

To obtain immunodeficient hemophilic mice (designated as factor VIII KO-SCID), FVIII-deficient mice were crossed with SCID mice. Genotyping and phenotypic characterization of the FVIIIKO and factor VIII KO-SCID offspring were performed confirming that all FVIII-deficient mice used in this study are factor VIII KO-SCID mice.

Immune deficient NOD-SCID or factor VIII KO-SCID mice (Weizmann Institute Animal Breeding Center, Rehovot, Israel) were used as hosts for the transplantation studies at the age of 8-10 weeks. All mice were kept in small cages (up to five animals in each cage) and fed sterile food and acid water containing ciprofloxacin (20 mg/ml).

Pig embryos were obtained from the Lahav Institute of Animal Research, Kibbutz Lahav, Israel. Pregnant sows were operated on at specific stages of the pregnancy (E24, E28, E42, E56, E80, and E100) under general anesthesia. Warm ischemia time was less than 10 minutes and the embryos were transferred to cold PBS. Spleen precursors for transplantation were extracted under a light microscope and were kept in sterile conditions at 40 degrees centigrade in RPMI 1640 (Biological Industries, Beit HaEmek, Israel) before transplantation. Cold ischemia time until transplantation was less than 2 hours. The study protocol was approved by the ethics committees at Kibbutz Lahav and the Weizmann Institute.

Transplantation Procedure:

Transplantations of the embryonic precursors were performed under general anesthesia (2.5 percent 2,2,2-Tribromoethanol, 97 percent in PBS, 10 ml/kg intraperitoneally). Host kidney was exposed through a left lateral incision. A 1.5-mm incision was made at the caudal end of the kidney capsule and donor precursors were grafted under the kidney capsule in fragments 1-2 mm in diameter.

Morphometric Analysis:

Specimens of pig embryo spleen, 6 weeks following transplantation, at different gestational ages (from E-28 to E-100) were formalin fixed and embedded in paraffin. Consecutive sections were cut and stained. The distance between sections was 40 microns. The areas of interest were quantified using the Image Pro program (Media Cybernetics).

Immunohistochemistry:

For immunohistochemical labeling, the following antibodies were used: mouse anti vimentin (clone V9) (Dako, Dako-Cytomation Denmark), mouse anti-human Ki67 (clone MIB-1) (Dako), rabbit anti human CD3 (Dako), mouse anti porcine CD31 (Serotec, Enco Scientific Services Ltd Israel), rabbit anti-Laminin (SIGMA-ALDRICH, Israel), rat anti mouse CD11b (Mac-1 antigen, clone M1/70) (BD Pharmingen, BD biosciences) and rat anti mouse TER-119 (BD Pharmingen).

Paraffin sections (4 microns) were xylene deparaffinized and rehydrated. Endogenous peroxidase was blocked with 0.3 percent hydrogen peroxide in 70 percent methanol for 10 minutes. Antigen retrieval procedures were performed by micro gal coking at pH 6 or enzymatic pretreatment according to the manufacturer's instructions.

After blocking, both paraffin sections and 6 micron cryosections were incubated with specific first antibody for 60 minutes. Detection of antibody binding was performed using Dako peroxidase Envision System for detection of mouse and rabbit antibodies. In both cases, diaminobenzidine (DAP) was used as a chromogen.

Real-Time PCR:

Grafts were dissected carefully from the subcapsular site and homogenized in Tri-reagent. Total RNA was isolated using the Tri-reagent method according to the manufacturer's instructions (Molecular Research Center, Inc., Cincinnati, Ohio). Purified RNA was treated with RQ1 RNase-Free DNase (Promega Corp. Madison, Wis.), then reverse transcribed into cDNA, and amplified using the Light Cycler quantitative PCR using primers specific for pig factor VIII and the housekeeping genes, pig transferrin receptor and mouse GAPDH.

Quantitative PCR reactions were carried out using triplicates of each sample using the Light Cycler reaction as instructed by the manufacturer (Roche Diagnostics Gmbh, Mannheim, Germany). The relative amount of product in each transplant was normalized to the level of pig transferrin receptor.

Primers used for pig factor VIII were: forward-CATGGACCTGCTTCAC; reverse-TGACACATGATTTAATC-CCG (SEQ ID NO: 2). Primers used for pig transferrin receptor were: forward-TGTGGCAGCTCAGAAT (SEQ ID NO: 3); reverse-ACCGATGTGGTTACTCC (SEQ ID NO: 4). To show specificity of these primers, primers specific for mouse GAPDH were also used: forward-CTGCGACTTCAACAGC (SEQ ID NO: 5); reverse-GGTGCAGCGAACTTTAT (SEQ ID NO: 6).

Plasma Factor VIII Assays:

Factor VIII activity was assayed in citrated plasma collected from recipients. PTT was determined with a coagulometer Sysmex CA-6000 (Assays were performed in the clinical hematology lab; Kaplan Medical Center, Rehovot). The chromogenic activity assay, which measures the FVIII dependent generation of FXa from FX (COATEST FVIII: Chromogenix, Molndal, Sweden), was performed.

Tail Clipping:

Tail clipping (approximately 1.5 cm from tip) was performed without subsequent cauterization to measure bleeding propensity. After the procedure, mice were checked every 4 hours. The proportion of surviving mice at 24 hours after the procedure was recorded.

Statistical Analysis:

Comparisons between groups were evaluated by the Student's t-test. Data were expressed as mean±SD, and were considered statistically significant at p values of 0.05 or less.

Experimental Results:

The gestational time window enabling the harvest of human and pig embryonic kidney precursor tissue for growing functional small kidneys in SCID mice has previously been established (16). More recently, similar 'windows' for pig embryonic pancreas, liver and lung were defined (17). In the present study, spleen embryonic tissue was harvested at different gestational time points and stained for CD3 positive cells to determine the precise period of time in pig ontogeny at which mature T cells are first present in these tissues. As can be seen in FIGS. 12a-e, T cells were initially detectable in the tissue obtained at the E56 gestational age.

Thus, in order to avoid GVHD, harvest of pig spleen tissue for transplant should be limited to E42 or earlier time points. To define the earliest gestational time point at which the maximal growth potential of transplanted tissue is exhibited, pig embryonic spleen tissues obtained at different stages, ranging from E28 to E100, were implanted into NOD/SCID mice, and 6 weeks later the implant's size, as well as its differentiation, were evaluated by computerized morphometric analysis. Consecutive sections were cut at 40 micron intervals and stained for vimentin (clone V9, which decorates pig but not mouse mesenchymal tissue), Ki67 (proliferation marker), and pig CD31 (endothelial cell marker); thereafter, using the Image Pro program, the total graft volume and fraction volumes of mesenchymal compartments were determined. As can be seen in Table 8, summarizing the results of the morphometric analysis, the largest implant volume was found following transplantation of tissue obtained at E42. The growth was significantly accelerated compared with implants obtained at earlier (E28) or later (E56, E80 and E100) gestational time points, suggesting unique growth potential of spleen precursors at particular time points during gestation.

TABLE 8

Morphometric analysis of pig splenic precursors

| Gestational age | Implant volume (mm3) | Vimentin volume (mm3) | Vimentin (percent of volume) |
|---|---|---|---|
| E28 | 4.9 ± 0.99 | 2.34 ± 0.454 | 47.8 |
| E42 | 21.94 ± 4.95 | 10.275 ± 2.736 | 46.8 |
| E56 | 10.49 ± 5.01 | 3.146 ± 1.419 | 30.0 |
| E80 | 5.82 ± 5.92 | 1.131 ± 0.063 | 19.4 |
| E100 | 0.088 ± 0.01 | 0.011 ± 0.006 | 12.2 |

A macroscopic image of the implant growing 6 weeks after transplantation of E42 pig spleen tissue is shown in FIG. 13a.

Figure 13D:
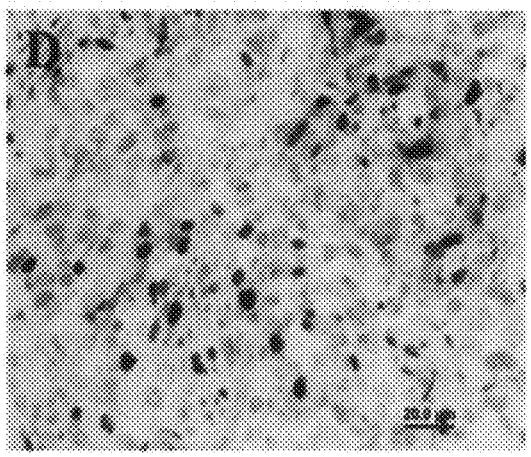

The pig origin of the stromal component was demonstrated by vimentin immunolabeling (FIG. 13b). These stromal cells are supported by pig blood vessels stained by anti-CD31 (FIG. 13c) (non-cross reactive with mouse CD31) and are highly proliferative, as demonstrated by high levels of Ki67 labeling (FIG. 13d).

Histological evaluation of the growing E42 spleen tissue at different time points revealed unorganized early stage in the formation of the hematopoietic compartment at 2 months posttransplant. Gradually, nests of hematopoietic red pulp-like splenic tissue are formed at month 3 (FIG. 14).

Immunostaining of Mac1 antigen expressed on mouse myeloid cells and with anti-Terr1 specific for the mouse erythroid cells, demonstrate that the pig stroma is gradually populated with host type myelopoiesis and erythropoiesis, as is typically found in the adult mouse spleen. However, mouse lymphopoiesis is not observed due to the SCID mutation of the implant recipients.

Similar patterns of hematopoietic nests, separated by connective tissue septa, were observed 5 months after transplantation. In these nests, hematopoietic cells were observed adjacent to loosely distributed mesenchymal stromal elements (data not shown). Thus, the E42 spleen tissue gradually assumes its hematopoietic character without any signs of aberrant differentiation typical of tumors and, in particular, of teratomas.

Taken together, these results suggest that of the early gestational stages devoid of T cells, E42 exhibits optimal growth potential and could, therefore, afford a suitable source for transplantation to correct hemophilia A or other genetic deficiencies.

Correction of Hemophilia A by E42 Pig Spleen Tissue:

Based on several indications in the literature that factor VIII is produced in the spleen of adult tissue (11-13), attempts were made to measure the expression of pig factor VIII in the implants growing from embryonic spleen tissue obtained at different time points. Since no porcine specific anti-factor VIII antibodies are available, tissue mRNA expression in the growing embryonic spleen mesenchyme in comparison to implants of pig embryonic pancreas was initially evaluated. Pig specific primers for factor VIII were developed and used to screen the growing implants. This analysis confirmed pig factor VIII mRNA expression in the spleen stroma derived from embryonic porcine E28 to E56 gestational age tissue, implanted into SCID mice (data not shown).

In order to more precisely determine the levels of porcine factor VIII expression in implants of pig embryonic spleen, graft-derived tissues were analyzed by RT-PCR. As can be seen in FIG. 15, 6 weeks after transplantation of E28, E42 or E56 spleen tissue, the grafts exhibited marked levels of porcine factor VIII mRNA expression, while pancreatic tissue growing out of embryonic pancreas precursor tissue did not exhibit an appreciable expression of factor VIII mRNA.

To ascertain the functionality of the transplanted tissue in factor VIII production, attempts were made to treat factor VIII KO mice (B6-129 background) by implantation of E42 pig spleen tissue. However, as the recipient KO mice have a relatively normal immune system, the implantation of pig tissue required continuous immune suppression involving intra-peritoneal injection of immunosuppressive drugs, a procedure that caused marked bleeding and high death rate due to the hemophilic status of the recipients (not shown). (Immunosuppression is anticipated to be technically easier in humans, as described below). Therefore, in order to circumvent the need for continuous injection of immune suppressive agents, a strain of VIII KO-SCID mice (18) was used to further analyze the potential of E42 spleen tissue to correct hemophilia A. Indeed, implantation in these mice, performed under short term treatment with soluble factor VIII to enable the animals to tolerate the surgical procedure, was not associated with high mortality, and the mice were able to withstand repeated testing for factor VIII activity.

Traditionally, a clotting assay measuring partial thromboplastin time (PTT) is used for testing factor VIII activity. In addition, the indirect Coatest chromogenic assay offers a more sensitive determination of the presence of factor VIII by measuring its activity on cleavage of Factor X.

As can be seen in FIG. 16, recipients of E42 spleen tissue exhibited normalized PTT levels by 3-4 months posttransplant. Thus, while untreated factor VIII KO-SCID mice or those at 2 weeks posttransplant exhibited PTT levels of 43.06±1.07 sec and 39.63±5.12 sec, respectively, the mice implanted with E42 spleen exhibited at 12 weeks posttransplantation markedly reduced PTT values (23.8±3.94 sec, P=0.001), comparable to the levels found in control, non-hemophilic SCID mice (22.12±1.14 sec, P=0.001).

Likewise, factor VIII blood level determined by the Coatest assay (FIG. 17*a-b*) revealed significantly elevated levels in the blood of transplanted mice at 14 weeks posttransplantation (63.4±49.6 percent of normal levels) compared to the levels found in factor VIII KO-SCID mice (zero values) and in non-hemophilic SCID mice (102±31.2 percent). Considering that severe, moderate and mild hemophilic states, defined by percentage of factor VIII are below 1, 4 and 6 percent, respectively, it is significant that the levels in the entire group of transplanted mice ranged above these amounts (between 7 to 100 percent of factor VIII activity)

Finally, when exposed to tail clipping, 7 out of 7 implanted mice survived, while almost all the non-implanted control mice died of bleeding within 24 hours (Table 9).

TABLE 9

Survival following tail clipping.

| Mouse strain | Treatment | Survival frequency |
| --- | --- | --- |
| SCID | None | 5/5 |
| SCID | E42 spleen transplantation | 3/3 |
| Factor VIII KO-SCID | None | 1/13 |
| Factor VIII KO-SCID | E42 spleen transplantation | 7/7 |

Discussion:

Taken together, the presently disclosed results show for the first time the feasibility of using embryonic spleen tissue, prior to the appearance of T cells in the tissue, for the correction of a genetic deficiency.

Hemophilia A is a bleeding disease caused by factor VIII deficiency. Factor VIII replacement therapy can reduce bleeding but is expensive, inconvenient, and often complicated by development of antibodies that inhibit factor VIII activity in 30 percent of patients. Clearly, a novel alternative source of factor VIII, such as embryonic spleen tissue, might open new treatment modalities which could provide long term benefit to hemophilia A patients.

A major obstacle to the implementation of embryonic allo- or xeno-transplantation in patients is related to its potential immunogenicity. Thus, the issue of immune suppression is critical, and further studies in large animal models are required to define whether long term immune tolerance towards the implanted embryonic spleen can be induced with minimal toxicity. Numerous studies over the past four decades have suggested that embryonic tissues are less prone to immune rejection (19-22). Nevertheless, exactly how much and for how long, immune suppression will be required to allow engraftment of fetal spleen tissue will determine its applicability to treating monogenic inherited diseases. Preliminary results suggest that E42 pig spleen is far less immunogenic compared to fetal spleen tissue obtained at later time points or compared to adult spleen (not shown), and furthermore, implantation in immunocompetent mice suggests that rejection can be prevented by co-stimulatory blockade, known to also effectively inhibit antibody production. Thus, it might be possible, in the future to address the issue of anti-factor VIII inhibitory antibodies by strategies combining neonatal transplantation of fetal spleen with short term co-stimulatory blockade or other mild tolerance-inducing modalities. However, considering that such approaches will be associated with some risks, it is envisioned that fetal spleen transplantation will be most suitable in diseases for which no therapy is currently available. Although it is presently demonstrated as proof of principle that transplantation of fetal spleen can ameliorate genetic deficiencies in hemophilic mice, the clinical evaluation of this approach will be initially justified in other diseases such as phenylketonuria (PKU) or ornithine transcarbamylase (OTC) deficiency, for which replacement therapy with an exogenous enzyme or factor is not available.

A second major issue that must be addressed in further studies is related to the choice of fetal tissue. As a proof of principle, the potential of pig embryonic tissue was evaluated. Several safety concerns, in particular the potential hazards associated with endogenous retroviruses (PERV), have presented major obstacles for this application (23-25). However, it is important to note that previous pig-to-human xenotransplantations have failed to reveal even a single instance of PERV transmission to a human subject (26). Moreover, a recent study has suggested that PERV could be eradicated from pig herds bred for xenotransplantation (27). Thus, as suggested recently by Ogata and Platt (28), although the potential danger of PERV to public health cannot be entirely dismissed, it should be approached with careful attention to the xenograft recipients, rather than necessitating that xenotransplantation studies be abandoned. However, pig embryonic tissue, while circumventing ethical issues associated with human embryonic stem cells or tissues might be more prone to rejection compared to human fetal spleen tissue.

Thus, the use of human fetal spleen tissue from early abortions, if deemed ethically acceptable, represents a potentially superior tissue source. Optimal gestational time for harvesting human spleen tissue is currently under investigation in SCID mice.

In conclusion, regardless of the immune suppression modalities which will be required and must be defined in large animal models, the presently disclosed data provide a proof of concept for the curative potential of T cell free, embryonic spleen tissue as a novel source for transplantation in patients with genetic deficiencies.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. G. J. Nabel, Nat Med 10, 135 (February, 2004).
2. S. Connelly et al., Blood 91, 3273 (May 1, 1998).
3. A. Tiede et al., Gene Ther 10, 1917 (October, 2003).
4. A. e. a. Van Damme, Haemophilia 9 (2003).
5. H. Do, J. F. Healey, E. K. Waller, P. Lollar, J Biol Chem 274, 19587 (Jul. 9, 1999).
6. A. A. Ashrani et al., Haemophilia 10, 735 (November, 2004).
7. J. H. Lewis, F. A. Bontempo, J. A. Spero, M. V. Ragni, T. E. Starzl, N Engl J Med 312, 1189 (May 2, 1985).
8. T. L. Marchloro, C. Hougie, H. Ragde, R. B. Epstein, E. D. Thomas, Science 163, 188 (Jan. 10, 1969).
9. C. G. Groth et al., Surgery 75, 725 (May, 1974).
10. J. J. Veltkamp et al., Transplantation 18, 56 (July, 1974).
11. W. E. Hathaway et al., Transplantation 7, 73 (January, 1969).
12. W. Z. Xiang, Z. W. Jie, X. S. Sheng, Transplant Proc 34, 1929 (August, 2002).
13. F. J. Dor, B. Gollackner, D. K. Cooper, Transpl Int 16, 451 (July, 2003).
14. C. G. Groth et al., Lancet 1, 1260 (Jun. 19, 1971).
15. M. H. Pappworth, Lancet 2, 220 (Jul. 24, 1971).
16. B. e. a. Dekel, Nat Med 9, 53 (2003).
17. S. Eventov-Friedman et al., Proc Natl Acad Sci USA 102, 2928 (Feb. 22, 2005).
18. M. K. Chuah et al., Blood 101, 1734 (Mar. 1, 2003).
19. P. B. Medawar, Symp. Soc. Exp. Biol. 7, 320 (1953).
20. G. Erdag, J. R. Morgan, Transplantation 73, 519 (Feb. 27, 2002).
21. R. P. Foglia, M. LaQuaglia, J. DiPreta, P. K. Donahoe, J Pediatr Surg 21, 608 (July, 1986).
22. R. P. Foglia, J. DiPreta, M. B. Statter, P. K. Donahoe, Ann Surg 204, 402 (October, 1986).
23. G. A. e. a. Langford, Transplantation 72, 1996 (2001).
24. S. J. Tacke, K. Bodusch, A. Berg, J. Denner, Xenotransplantation 8, 125 (May, 2001).
25. R. B. e. a. Elliott, Cell Transplant 9, 895 (2000).
26. K. Paradis et al., Science 285, 1236 (Aug. 20, 1999).
27. D. A. e. a. Clark, Xenotransplantation 10, 142 (2003).
28. K. Ogata, J. L. Platt, J Heart Lung Transplant 23, 515 (May, 2004).

What is claimed is:

1. A method of providing a pancreatic function to a human subject, the method comprising transplanting into the subject a porcine pancreatic vascularized organ/tissue graft, wherein said porcine pancreatic vascularized organ/tissue graft is at a gestational stage of about 42 to about 56 days of gestation, thereby generating a functional porcine pancreatic organ/tissue for providing the pancreatic function to the subject.

2. The method of claim 1, wherein the subject has an abnormal activity of a biomolecule naturally produced by a mammalian pancreas.

3. The method of claim 2, wherein said biomolecule is insulin.

4. The method of claim 1, wherein the subject has an abnormal activity of a biomolecule naturally produced by a mammalian pancreatic islet.

5. The method of claim 1, further comprising transiently administering to the subject at least one T-cell costimulation inhibitor and at least one CD40 ligand inhibitor.

6. The method of claim 1, wherein said transplanting said graft into the subject is effected by transplanting said graft under at least one renal capsule of the subject.

7. The method of claim 1, wherein said transplanting said graft into the subject is effected into the pancreas.

* * * * *